(12) United States Patent
Bellin

(10) Patent No.: US 8,596,124 B2
(45) Date of Patent: *Dec. 3, 2013

(54) ACOUSTIC EMISSION TOUGHNESS TESTING HAVING SMALLER NOISE RATIO

(75) Inventor: Federico Bellin, The Woodlands, TX (US)

(73) Assignee: Varel International Ind., L.P., Carrollton, TX (US)

(*) Notice: Subject to any disclaimer, the term of this patent is extended or adjusted under 35 U.S.C. 154(b) by 230 days.

This patent is subject to a terminal disclaimer.

(21) Appl. No.: 13/152,126

(22) Filed: Jun. 2, 2011

(65) Prior Publication Data

US 2011/0239767 A1    Oct. 6, 2011

Related U.S. Application Data

(63) Continuation-in-part of application No. 12/963,913, filed on Dec. 9, 2010, now Pat. No. 8,365,599, which is a continuation-in-part of application No. 12/769,221, filed on Apr. 28, 2010, now Pat. No. 8,397,572, which is a continuation-in-part of application No. 12/754,784, filed on Apr. 6, 2010, now Pat. No. 8,322,217.

(51) Int. Cl.
*G01N 29/14* (2006.01)
*G01N 3/48* (2006.01)

(52) U.S. Cl.
USPC .................................. 73/587; 73/81

(58) Field of Classification Search
USPC ........ 73/587, 81, 573, 578, 821, 827; 702/41, 702/56
See application file for complete search history.

(56) References Cited

U.S. PATENT DOCUMENTS 3,822,586 A    7/1974    Pollock
3,865,291 A    2/1975    Haden
(Continued)

FOREIGN PATENT DOCUMENTS

DE    4340669    6/1995
EP    1189051    3/2002
(Continued)

OTHER PUBLICATIONS

Kazuhisa Miyoshi, Structures and Mechanical Properties of Natural and Synthetic Diamonds, Lewis Research Centr, Ohio, NASA TM-1998-107249, Chapter 8, pp. 1-26, Jun. 1998.

(Continued)

*Primary Examiner* — Helen Kwok
(74) *Attorney, Agent, or Firm* — King & Spalding LLP

(57) ABSTRACT

A method, system and apparatus for testing properties of a hard component. The apparatus includes a holder, a component, an indenter, a sensor holder, and an acoustic sensor. The holder includes a first end and a second end opposite the first end. The first end defines a first cavity extending towards the second end. The component is positioned in the first cavity. The indenter is positioned adjacent to a portion of the component and applies a load onto the component. The sensor holder includes an upper portion, a lower portion, and a second cavity therein. The upper portion is coupled to the second end. The sensor is positioned within the second cavity. In some embodiments, the apparatus includes a rod coupled to the lower portion. The rod has a lower acoustic impedance than the sensor holder, thereby allowing sound waves to pass through the sensor holder and not be reflected back into the sensor.

24 Claims, 21 Drawing Sheets

(56) References Cited

U.S. PATENT DOCUMENTS

| | | | |
|---|---|---|---|
| 4,036,057 | A | 7/1977 | Morais |
| 4,354,558 | A | 10/1982 | Jageler et al. |
| 4,529,184 | A | 7/1985 | Vandermeerssche |
| 4,609,994 | A | 9/1986 | Bassim et al. |
| 4,629,011 | A | 12/1986 | Reinhardt |
| 4,686,653 | A | 8/1987 | Staron et al. |
| 4,714,119 | A | 12/1987 | Hebert et al. |
| 4,858,462 | A | 8/1989 | Coulter et al. |
| 4,987,969 | A | 1/1991 | Boyle et al. |
| 5,000,045 | A | 3/1991 | Secoy |
| 5,025,669 | A | 6/1991 | Sarda et al. |
| 5,318,123 | A | 6/1994 | Venditto et al. |
| 5,370,195 | A | 12/1994 | Keshavan et al. |
| 5,433,207 | A | 7/1995 | Pretlow, III |
| 5,438,169 | A | 8/1995 | Kennedy et al. |
| 5,517,854 | A | 5/1996 | Plumb et al. |
| 5,587,532 | A | 12/1996 | Rose |
| 5,617,927 | A | 4/1997 | Maissa |
| 5,631,423 | A | 5/1997 | Rhodes |
| 5,776,615 | A | 7/1998 | Wong et al. |
| 5,969,241 | A | 10/1999 | Auzerais |
| 6,003,599 | A | 12/1999 | Huber et al. |
| 6,041,020 | A | 3/2000 | Caron et al. |
| 6,181,642 | B1 | 1/2001 | Coates et al. |
| 6,349,595 | B1 | 2/2002 | Civolani et al. |
| 6,494,765 | B2 | 12/2002 | Gitis et al. |
| 6,502,455 | B1 | 1/2003 | Gitis et al. |
| 6,536,553 | B1 | 3/2003 | Scanlon |
| 6,595,290 | B2 | 7/2003 | George et al. |
| 6,612,382 | B2 | 9/2003 | King |
| 6,788,054 | B2 | 9/2004 | Collins et al. |
| 6,795,773 | B2 | 9/2004 | Soliman et al. |
| 6,799,472 | B2 | 10/2004 | Nakayama et al. |
| 6,938,465 | B2 | 9/2005 | Goto |
| 6,981,549 | B2 | 1/2006 | Morales et al. |
| 7,040,170 | B2 | 5/2006 | Tokunaga et al. |
| 7,258,833 | B2 | 8/2007 | Rainey et al. |
| 7,493,971 | B2 | 2/2009 | Nevlud et al. |
| 7,552,648 | B2 | 6/2009 | McMechan et al. |
| 7,558,369 | B1 | 7/2009 | Mourik et al. |
| 7,900,717 | B2 | 3/2011 | Radford et al. |
| 8,322,217 | B2 * | 12/2012 | Bellin ............................. 73/587 |
| 8,365,599 | B2 * | 2/2013 | Bellin ............................. 73/587 |
| 8,397,572 | B2 * | 3/2013 | Bellin ............................. 73/578 |
| 2002/0116980 | A1 | 8/2002 | Kerr et al. |
| 2003/0094034 | A1 | 5/2003 | Feng et al. |
| 2005/0172702 | A1 | 8/2005 | Gitis et al. |
| 2006/0185430 | A1 | 8/2006 | Yogeswaren |
| 2011/0239764 | A1 | 10/2011 | Bellin |
| 2011/0239765 | A1 | 10/2011 | Bellin |
| 2011/0246096 | A1 | 10/2011 | Bellin |
| 2011/0246102 | A1 * | 10/2011 | Bellin ............................. 702/56 |
| 2011/0286304 | A1 * | 11/2011 | Thigpen et al. ................. 367/25 |

FOREIGN PATENT DOCUMENTS

| | | |
|---|---|---|
| JP | 11352043 | 12/1999 |
| RU | 2147737 | 4/2000 |
| SU | 1670591 | 8/1991 |
| SU | 1760433 | 9/1992 |
| WO | 0125597 | 4/2001 |
| WO | 2011022408 | 2/2011 |

OTHER PUBLICATIONS

M.K. Keshavan, M.A. Siracki, and M.E. Russell, Smith International Inc., Diamond-Enhanced Insert: New Compositions and Shapes for Drilling Soft-to-Hard Formations, Society of Petroleum Engineers/International Association of Drilling Contractors, SPE/IADC 25737, pp. 577-591, Feb. 1993.

R.L. Mehan and L.E. Hibbs, Thermal Degradation of Sintered Diamond Compacts, General Electric Research and Development Center, General Electric Company, New York, Journal of Materials Science 24, pp. 942-950, 1989.

M.H.B Nasserl, B.Schubnel A. Thompson, and R. P. Young, Acoustic Emission Monitoring of Mode I Fracture Toughness (CCNBD) Test in Lac du Bonnet Granite, ARMA, American Rock Mechanics Association, Jun. 2005, Anchorage, Alaska.

Michael J. Little et al., "Evaluation of Acoustic Emission as a means for cabonate determination", Analytica Chimica Acta, Jun. 1, 1995, pp. 283-292, vol. 309, No. 1-3, Elsevier Science B.V.

Granger et al., "Experimental Characterization of the Self-Healing of Cracks in an Ultra High Performance Cementitious Material: Mechanical Tests and Acoustic Emission Analysis", Cement and Concrete Research, Pergamon Press, Mar. 29, 2007, pp. 519-527, vol. 37, No. 4, Elsevier Ltd.

A. Guarino et al., "Failure Time and Critical Behaviour of Fracture Precursors in Heterogeneous Materials", The European Physical Journal B, Mar. 1, 2002, pp. 141-151, vol. 25, No. 2, EDP Sciences, Societa Italiana di Fisica, Springr-Verlag 2002.

B.V. Tanikella et al., "Fracture Damage in Borosilicate Glass During Microcutting Tests", Scripta Materialia, Jan. 15, 1996, pp. 207-213, vol. 34, No. 2, Acta Metallurgica Inc., USA.

B.V. Tanikella et al., "Indentation and Microcutting Fracture Damage in a Silicone Carbide Coating on an Incoloy Substrate", Surface and Coatings Technology, Jan. 1, 1997, pp. 119-126, vol. 88, No. 1-3, Elsevier Sciences S.A.

R. Ikeda et al., "Fracture Observation of Polycrystalline Diamond Film Under Indentation Test", Diamond and Related Materials, Nov. 1, 2004, pp. 2024-2030, vol. 13, No. 11-12, Elsevier B.V.

P. Dyjak et al., "Acoustic Emission Analysis of Nanoindentation-Induced Fracture Events", Experimental Mechanics, Mar. 27, 2006, pp. 333-345, vol. 46, No. 3, Society for Experimental Mechanics P.S. From et al.,"Indentation and Acoustic Emission in Filtration Processed Platelet Reinforced Ceramics", Materials Science & Engineering A, Jul. 1, 1995, pp. 231-236, vol. A197, No. 2, Elsevier Science S.A.

Wang et al., "Failure Mode of Dental Restorative Materials Under Hertzian Indentation", Dental Materials, Aug. 11, 2007, pp. 1236-1244, vol. 23, No. 10, Elsevier Ltd.

S. J. Jung et al., "Prediction of Rock Hardness and Drillability Using Acoustic Emission Signatures During Indentation", International Journal of Rock Mechanics and Mining Sciences & Geomechanics Abstract, Oct. 1994, pp. 561-567, vol. 31, No. 5, Elsevier Science Ltd.

Energy American Petroleum Institute, "Hydraulic Fracturing Operations- Well Construction and Integrity Guidelines", API Guidance Document HF1, First Edition, Oct. 2009, pp. 1-35, Energy American Petroleum Institute.

B.A. Eaton et al., Manufactured Diamond Cutters Used in Drilling Bits, Journal of Petroleum Technology, May 1975, pp. 543-551.

Ken Bertagnolli and Roger Vale, Understanding and Controlling Residual Stresses in Thick Polycrystalline Diamond Cutters for Enhanced Durability,9 pages, US Synthetic Corporation, 2000.

Maurer, William C., Advanced Drilling Techniques, Chapter 22 Stratapax Bits, The Petroleum Publishing Company, pp. 541-591, 1980.

J. L. Knill et al., A Study of Acoustic Emission from Stressed Rock Mechanics and Mining Sciences & Geomechanics Abstracts, vol. 5., No. 1, Jan. 1, 1968, pp. 87-121.

* cited by examiner

ACOUSTIC EMISSION TOUGHNESS TESTING HAVING SMALLER NOISE RATIO

RELATED APPLICATIONS

The present application is a continuation-in-part of U.S. patent application Ser. No. 12/963,913, entitled "Acoustic Emission Toughness Testing For PDC, PCBN, Or Other Hard Or Superhard Materials" and filed on Dec. 9, 2010, which is a continuation-in-part of U.S. patent application Ser. No. 12/769,221, entitled "Acoustic Emission Toughness Testing For PDC, PCBN, Or Other Hard Or Superhard Materials" and filed on Apr. 28, 2010, which is a continuation-in-part of U.S. patent application Ser. No. 12/754,784, entitled "Acoustic Emission Toughness Testing For PDC, PCBN, Or Other Hard Or Superhard Material Inserts" and filed on Apr. 6, 2010, which are all hereby incorporated by reference.

The present application also is related to U.S. patent application Ser. No. 12/754,738, entitled "Acoustic Emission Toughness Testing For PDC, PCBN, Or Other Hard Or Superhard Material Inserts" and filed on Apr. 6, 2010, which also is hereby incorporated by reference.

TECHNICAL FIELD

The present invention relates generally to a method, apparatus, and software for testing the intrinsic strength, or toughness, of hard or superhard materials; and more particularly, to a method, apparatus, and software for testing the intrinsic strength, or toughness, of hard or superhard materials, such as rock samples and inserts for downhole tools, using acoustic emissions.

BACKGROUND

FIG. 1 shows a superhard material 100 that is insertable within a downhole tool (not shown), such as a drill bit or a reamer, in accordance with an exemplary embodiment of the invention. One example of a superhard material 100 is a cutting element 100, or cutter or insert, for rock bits, as shown in FIG. 1. However, the superhard material 100 can be formed into other structures based upon the application that it is to be used in. In other examples, the superhard material 100 is a rock sample, which can be obtained from within a wellbore or from other sources. The cutting element 100 typically includes a substrate 110 having a contact face 115 and a cutting table 120. The cutting table 120 is fabricated using an ultra hard layer which is bonded to the contact face 115 by a sintering process according to one example. According to some examples, the substrate 110 is generally made from tungsten carbide-cobalt, or tungsten carbide, while the cutting table 120 is formed using a polycrystalline ultra hard material layer, such as polycrystalline diamond ("PCD") or polycrystalline cubic boron nitride ("PCBN"). These cutting elements 100 are fabricated according to processes and materials known to persons having ordinary skill in the art. Although the cutting table 120 is shown having a substantially planar outer surface, the cutting table 120 can have alternative shaped outer surfaces, such as dome-shaped, concave-shaped, or other non-planar shaped outer surfaces, in other embodiments. Although some exemplary formulations for the cutting element 100 have been provided, other formulations and structures known to people having ordinary skill in the art can be used depending upon the application. Although rock drilling is one application that the superhard material 100 can be used in or obtained from and which is described hereinbelow, the superhard material 100 can be used in or obtained from various other applications including, but not limited to, machining, woodworking, and quarrying.

Different PCD, PCBN, hard, and superhard material grades are available for the cutters 100 to be used in various applications, such as drilling different rock formations using different drill bit designs or machining different metals or materials. Common problems associated with these cutters 100 include chipping, spalling, partial fracturing, cracking, and/or flaking of the cutting table 120 during use. These problems result in the early failure of the cutting table 120 and/or the substrate 110. Typically, high magnitude stresses generated on the cutting table 120 at the region where the cutting table 120 makes contact with earthen formations during drilling can cause these problems. These problems increase the cost of drilling due to costs associated with repair, production downtime, and labor costs. Thus, an end-user, such as a bit designer or a field application engineer, chooses the best performing grade of the cutter 100 for any given drilling or machining task to reduce these common problems from occurring. For example, the end-user selects an appropriate cutter 100 by balancing the wear resistance and the impact resistance of the cutter 100, as determined using conventional methods. Typically, the information available to the end-user for selecting the appropriate grade cutter 100 for a particular application is derived from historical data records that show performance of different grades of PCD, PCBN, hard, or superhard material in specific areas and/or from laboratory functional tests which attempt to mimic various drilling or machining conditions while testing different cutters 100. There are currently two main categories of laboratory functional testing that are used in the drilling industry. These tests are the wear abrasion test and the impact test.

Superhard materials 100, which include polycrystalline diamond compact ("PDC") cutters 100, have been tested for abrasive wear resistance through the use of two conventional testing methods. The PDC cutter 100 includes the cutting table 120 fabricated from PCD. FIG. 2 shows a lathe 200 for testing abrasive wear resistance using a conventional granite log test. Although one exemplary apparatus configuration for the lathe 200 is provided, other apparatus configurations known to people having ordinary skill in the art can be used without departing from the scope and spirit of the exemplary embodiment.

Referring to FIG. 2, the lathe 200 includes a chuck 210, a tailstock 220, and a tool post 230 positioned between the chuck 210 and the tailstock 220. A target cylinder 250 has a first end 252, a second end 254, and a sidewall 258 extending from the first end 252 to the second end 254. According to the conventional granite log test, sidewall 258 is an exposed surface 259 which makes contact with the superhard component 100 during the test. The first end 252 is coupled to the chuck 210, while the second end 254 is coupled to the tailstock 220. The chuck 210 is configured to rotate, thereby causing the target cylinder 250 to also rotate along a central axis 256 of the target cylinder 250. The tailstock 220 is configured to hold the second end 254 in place while the target cylinder 250 rotates. The target cylinder 250 is fabricated from a single uniform material, which is typically granite. However, other rock types have been used for the target cylinder 250, which includes, but is not limited to, Jackforck sandstone, Indiana limestone, Berea sandstone, Carthage marble, Champlain black marble, Berkley granite, Sierra white granite, Texas pink granite, and Georgia gray granite.

The PDC cutter 100 is fitted to the lathe's tool post 230 so that the PDC cutter 100 makes contact with the target cylinder's 250 exposed surface 259. The lathe's tool post 230 draws the PDC cutter 100 back and forth across the exposed surface 259. The tool post 230 has an inward feed rate on the target cylinder 250. The abrasive wear resistance for the PDC cutter 100 is determined as a wear ratio, which is defined as the volume of target cylinder 250 that is removed to the volume of the PDC cutter 100 that is removed. Alternatively, instead of measuring volume, the distance that the PDC cutter 100 travels across the target cylinder 250 can be measured and used to quantify the abrasive wear resistance for the PDC cutter 100. Alternatively, other methods known to persons having ordinary skill in the art can be used to determine the wear resistance using the granite log test. Operation and construction of the lathe 200 is known to people having ordinary skill in the art. Descriptions of this type of test is found in the Eaton, B. A., Bower, Jr., A. B., and Martis, J. A. "Manufactured Diamond Cutters Used In Drilling Bits." *Journal of Petroleum Technology*, May 1975, 543-551. Society of Petroleum Engineers paper 5074-PA, which was published in the Journal of Petroleum Technology in May 1975, and also found in Maurer, William C., *Advanced Drilling Techniques*, Chapter 22, The Petroleum Publishing Company, 1980, pp. 541-591, which is incorporated by reference herein.

FIG. 3 shows a vertical boring mill 300 for testing abrasive wear resistance using a vertical boring mill ("VBM") test or vertical turret lathe ("VTL") test. Although one exemplary apparatus configuration for the VBM 300 is provided, other apparatus configurations can be used without departing from the scope and spirit of the exemplary embodiment. The vertical boring mill 300 includes a rotating table 310 and a tool holder 320 positioned above the rotating table 310. A target cylinder 350 has a first end 352, a second end 354, and a sidewall 358 extending from the first end 352 to the second end 354. According to the conventional VBM test, second end 354 is an exposed surface 359 which makes contact with a superhard material 100 during the test. The target cylinder 350 is typically about thirty inches to about sixty inches in diameter; however, this diameter can be greater or smaller.

The first end 352 is mounted on the lower rotating table 310 of the VBM 300, thereby having the exposed surface 359 face the tool holder 320. The PDC cutter 100 is mounted in the tool holder 320 above the target cylinder's exposed surface 359 and makes contact with the exposed surface 359. The target cylinder 350 is rotated as the tool holder 320 cycles the PDC cutter 100 from about the center of the target cylinder's exposed surface 359 out to about its edge and back again to about the center of the target cylinder's exposed surface 359. The tool holder 320 has a predetermined downward feed rate. The VBM method allows for higher loads to be placed on the PDC cutter 100 and the larger target cylinder 350 provides for a greater rock volume for the PDC cutter 100 to act on. The target cylinder 350 is typically fabricated from granite; however, the target cylinder can be fabricated from other materials that include, but is not limited to, Jackforck sandstone, Indiana limestone, Berea sandstone, Carthage marble, Champlain black marble, Berkley granite, Sierra white granite, Texas pink granite, and Georgia gray granite.

The abrasive wear resistance for the PDC cutter 100 is determined as a wear ratio, which is defined as the volume of target cylinder 350 that is removed to the volume of the PDC cutter 100 that is removed. Alternatively, instead of measuring volume, the distance that the PDC cutter 100 travels across the target cylinder 350 can be measured and used to quantify the abrasive wear resistance for the PDC cutter 100. Alternatively, other methods known to persons having ordinary skill in the art can be used to determine the wear resistance using the VBM test. Operation and construction of the VBM 300 is known to people having ordinary skill in the art. A description for this type of testing can be found in Bertagnolli, Ken and Vale, Roger, "Understanding and Controlling Residual Stresses in Thick Polycrystalline Diamond Cutters for Enhanced Durability," US Synthetic Corporation, 2000, which is incorporated by reference in its entirety herein.

In addition to testing for abrasive wear resistance, PDC cutters 100 also can be tested for resistance to impact loading. FIG. 4 shows a drop tower apparatus 400 for testing impact resistance of superhard components using a "drop hammer" test where a metal weight 450 is suspended above and dropped onto the cutter 100. The "drop hammer" test attempts to emulate the type of loading that can be encountered when the PDC cutter 100 transitions from one formation to another or experiences lateral and axial vibrations. Results from the impact testing allows for ranking different cutters based upon their impact strength; however, these ranking do not allow for predictions to be made according to how the cutters 100 will perform in the actual field.

Referring to FIG. 4, the drop tower apparatus 400 includes a superhard material 100, such as a PDC cutter, a target fixture 420, and a strike plate 450 positioned above the superhard material 100. The PDC cutter 100 is locked into the target fixture 420. The strike plate 450, or weight, is typically fabricated from steel and is positioned above the PDC cutter 100. However, the strike plate 450 can be fabricated from alternative materials known to persons having ordinary skill in the art. The PDC cutter 100 is typically held at a backrake angle 415 with the diamond table 120 of the PDC cutter 100 angled upward towards the strike plate 450. The range for the backrake angle 415 is known to people having ordinary skill in the art.

The strike plate 450 is repeatedly dropped down on the edge of the PDC cutter 100 until the edge of the PDC cutter 100 breaks away or spalls off. These tests are also referred to as "side impact" tests because the strike plate 450 impacts an exposed edge of the diamond table 120. Failures typically appear in either the diamond table 120 or at the contact face 115 between the diamond table 120 and the carbide substrate 110. The "drop hammer" test is very sensitive to the edge geometry of the diamond table 120. If the table 120 is slightly chamfered, the test results can be altered considerably. The total energy, expressed in Joules, expended to make the initial fracture in the diamond table 120 is recorded. For more highly impact resistant cutters 100, the strike plate 450 can be dropped according to a preset plan from increasing heights to impart greater impact energy on the cutter 100 to achieve failure. However, this "drop hammer" test embodies drawbacks in that this method requires that many cutters 100 be tested to achieve a valid statistical sampling that can compare the relative impact resistance of one cutter type to another cutter type. The test is inadequate in providing results that reflect the true impact resistance of the entire cutter 100 as it would see impact loads in a downhole environment. The test exhibits a static impact effect whereas the true impact is dynamic. The number of impacts per second can be as high as 100 hertz ("Hz"). Also, the amount of damage to the cutter 100 is subjectively evaluated by someone with a trained eye and is compared to damages incurred by other cutters.

While the results for different wear tests available in the market have generally a reasonable degree of agreement with the actual field performance, the same is not the case for the results of conventional impact tests. Although there is some degree of correlation between the results of conventional impact tests and actual field performance, the scattering of the data is usually very large, thereby causing predictions on how cutters will behave in actual field performance to be difficult and/or inaccurate. Also, many fractures occurring within the cutter are not detected using these conventional tests and therefore go undetected when evaluating the toughness of the cutter.

Additionally, since the bit selection is a critical process, it is important to know the mechanical properties of the different rocks the bit is to drill through. One of the most important parameters currently used for the bit selection is the unconfined compressive strength ("UCS") of the rock, which can be measured directly on core samples or evaluated indirectly from log data. However, the UCS of the rock should not be solely relied on when selecting the bit because the UCS can be misleading, especially when the rock UCS is greater than 15000 psi and is brittle, thereby having a low fracture toughness $K_{1C}$. Thus, fracture toughness of the rock should also be considered when selecting the proper drill bit.

BRIEF DESCRIPTION OF THE DRAWINGS

The foregoing and other features and aspects of the invention are best understood with reference to the following description of certain exemplary embodiments, when read in conjunction with the accompanying drawings, wherein.

The drawings illustrate only exemplary embodiments of the invention and are therefore not to be considered limiting of its scope, as the invention may admit to other equally effective embodiments.

BRIEF DESCRIPTION OF EXEMPLARY EMBODIMENTS

The present invention is directed to a method, apparatus, and software for testing the intrinsic strength, or toughness, of hard or superhard materials, such as inserts and rock samples obtained from a down hole formation, using acoustic emissions. Although the description of exemplary embodiments is provided below in conjunction with a PDC cutter, alternate embodiments of the invention may be applicable to other types of hard or superhard materials including, but not limited to, PCBN cutters, rock samples, or other hard or superhard materials known or not yet known to persons having ordinary skill in the art. For example, the hard or superhard materials include cemented tungsten carbide, silicon carbide, tungsten carbide matrix coupons, ceramics, or chemical vapor deposition ("CVD") coated inserts. The hard or superhard materials also include rock samples that include, but are not limited to, hard rock samples and/or cemented rock samples obtained from a down hole formation or drill hole. According to some exemplary embodiments of the present invention, one or more properties of a rock sample is determined by measuring the fracture events occurring within the rock sample when subjected to fracture-causing pressures. In certain exemplary embodiments, the fracture events are measured over time and space. Measuring at least the intensity and/or the locations of the fractures within the rock sample facilitate in selecting the appropriate cutter types to be used for the drilling application according to some exemplary embodiments. In some exemplary embodiments, measuring at least the intensity and/or the locations of the fractures within the rock sample facilitate in selecting at least one parameter of a high pressure down hole fracturing program or at least one parameter of a down hole drilling program targeted to the down hole formation or similar down hole formations from which the rock sample was obtained.

Figure 5:
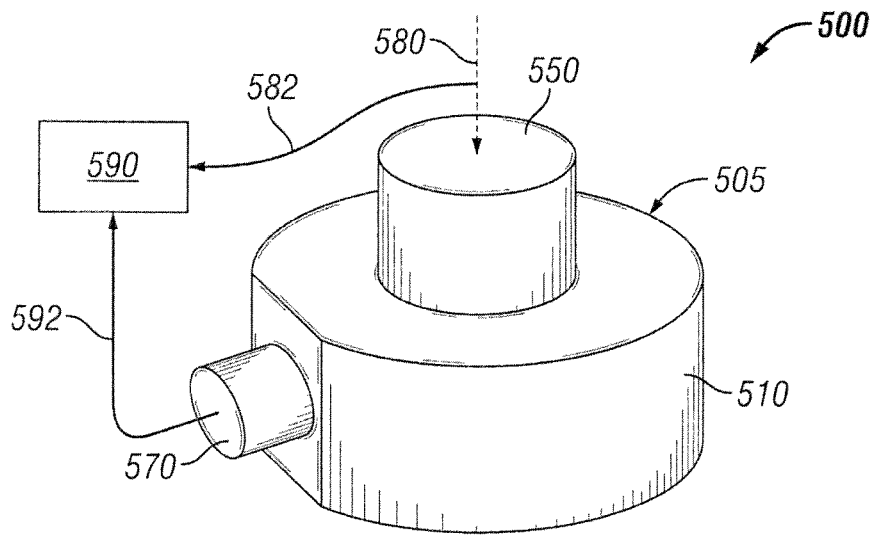
FIG. 5 shows a perspective view of an acoustic emission testing system in accordance with an exemplary embodiment of the present invention.
Figure 6:
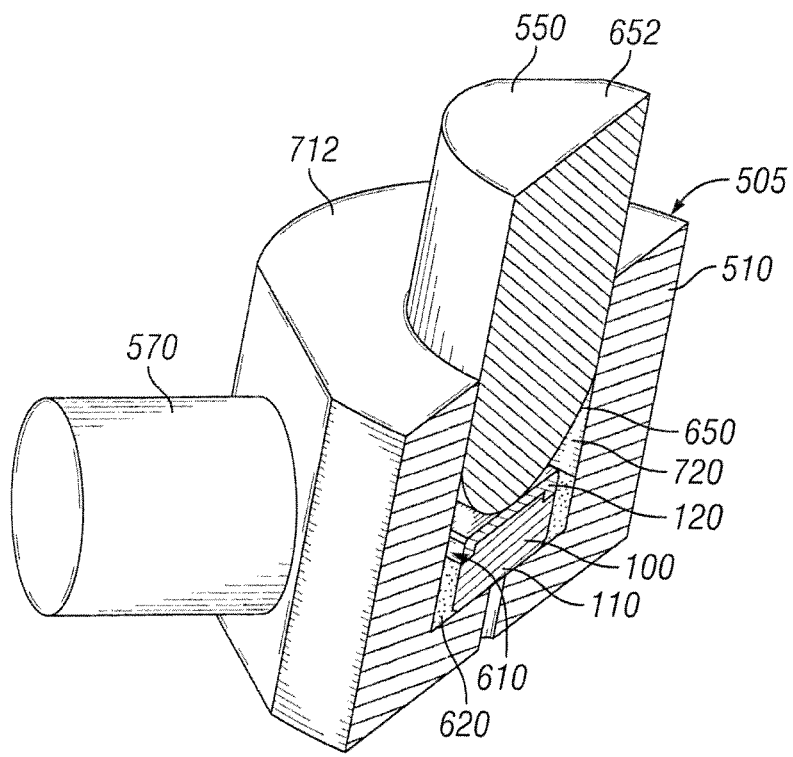
FIG. 6 shows a cross-sectional view of the acoustic emission testing device of FIG. 5 in accordance with an exemplary embodiment of the present invention.

The invention is better understood by reading the following description of non-limiting, exemplary embodiments with reference to the attached drawings, wherein like parts of each of the figures are identified by like reference characters, and which are briefly described as follows. FIG. 5 shows a perspective view of an acoustic emission testing system 500 in accordance with an exemplary embodiment of the present invention. FIG. 6 shows a cross-sectional view of the acoustic emission testing device 505 of FIG. 5 in accordance with an exemplary embodiment of the present invention. Referring to FIGS. 5 and 6, the acoustic emission testing system 500 includes an acoustic emission testing device 505 communicably coupled to a data recorder 590. The acoustic emission testing device 505 includes a cutter holder 510, the cutter 100, an indenter 550, and an acoustic sensor 570. In certain embodiments, however, the cutter holder 510 is optional. Although the cutter 100 is depicted in the exemplary embodiment, a rock sample 2300 (FIG. 23) replaces the cutter 100 in alternative exemplary embodiments.

Figure 7:
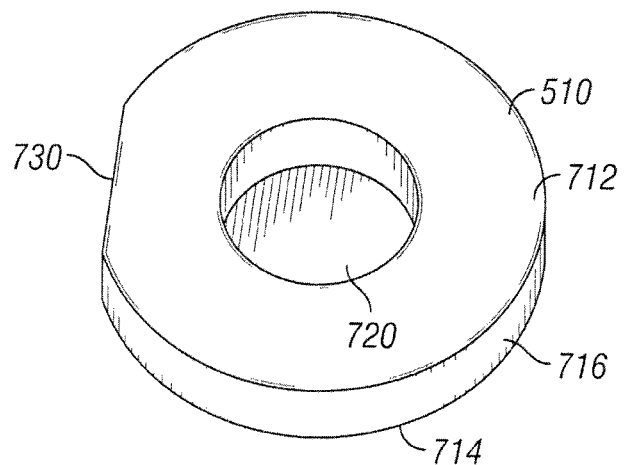
FIG. 7 shows a perspective view of a cutter holder, as shown in FIG. 5, in accordance with an exemplary embodiment of the present invention.

FIG. 7 shows a perspective view of the cutter holder 510 in accordance with an exemplary embodiment of the present invention. Referring to FIGS. 5, 6, and 7, the cutter holder 510 includes first surface 712, a second surface 714, and a side surface 716. The first surface 712 is disposed in a plane that is substantially parallel to the plane that the second surface 714 is disposed. The side surface 716 extends from the first surface 712 to the second surface 714. According to some exemplary embodiments, the side surface 716 is substantially perpendicular to at least one of the first surface 712 and the second surface 714. According to alternative exemplary embodiments, the side surface 716 is not substantially perpendicular to either the first surface 712 or the second surface 714. The cutter holder 510 is fabricated from steel; however, according to other exemplary embodiments, the cutter holder 510 is fabricated from any metal, wood, or other suitable material known to people having ordinary skill in the art that is capable of withstanding a load 580, which is described in further detail below, that is to be applied. The load 580 can range from about zero kilonewtons to about seventy kilonewtons. In certain exemplary embodiments, the suitable material is capable of being machined or molded and is capable of propagating sound. In certain exemplary embodiments, the suitable material is capable of propagating sound at a speed of about 1 kilometers per second or higher.

The cutter holder 510 is shaped in a substantially cylindrical shape, wherein the first surface 712 is substantially circular shaped, the second surface is substantially circular shaped, and the side surface 716 is substantially arcuate shaped. However, the side surface 716 includes a coupling portion 730, which is substantially planar, or flat-surfaced, and extends from the first surface 712 to the second surface 714. The coupling portion 730 provides a surface for coupling the acoustic sensor 570 to the cutter holder 510. In certain exemplary embodiments, the coupling portion 730 does not extend the entire length from the first surface 712 to the second surface 714. In some exemplary embodiments, the acoustic sensor 570 is sized such that the acoustic sensor 570 is able to be coupled to the side surface 716 that is arcuate shaped. Thus, the coupling portion 730 is optional in those exemplary embodiments. Although one exemplary shape is provided for the cutter holder 510, the cutter holder 510 can be shaped into any other geometric or non-geometric shape, such as square shaped cylinder or triangular shaped cylinder, without departing from the scope and spirit of the exemplary embodiment.

A cavity 720 is formed within the cutter holder 510 and is sized to receive the cutter 100, or some other hard or superhard material such as a rock sample 2300 (FIG. 23), which is further described below. The cavity 720 is sized slightly larger in diameter than the diameter of the cutter 100, thereby allowing the cutter 100 to easily and freely fit within the cavity 720. The cavity 720 extends from the first surface 712 towards the second surface 714, but does not reach the second surface 714. In other exemplary embodiments, the cavity 720 extends from the first surface 712 to the second surface 714 and proceeds through the cutter holder 510, thereby forming a hole within the cutter holder 510. The cavity 720 is circular in shape, but is any other geometric or non-geometric shape in other exemplary embodiments. The cavity 720 is formed by machining the cutter holder 510 or molding the cutter holder 510 to have the cavity 720 formed therein. Alternatively, the cavity 720 is formed using other methods known to people having ordinary skill in the art. In certain exemplary embodiments, the cavity 720 is formed in a manner to ensure that the cutter 100 is properly aligned in the same manner each time the cutter 100 is inserted within the cavity 720.

Figure 1:
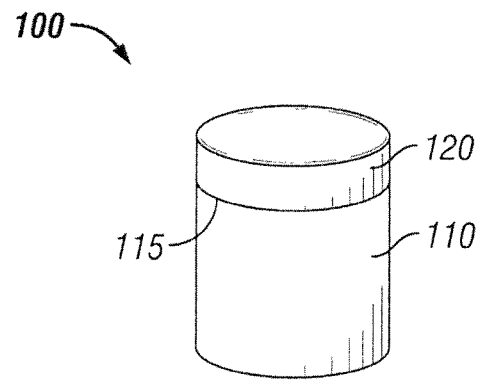
FIG. 1 shows a superhard material that is insertable within a downhole tool in accordance with an exemplary embodiment of the invention.
Figure 2:
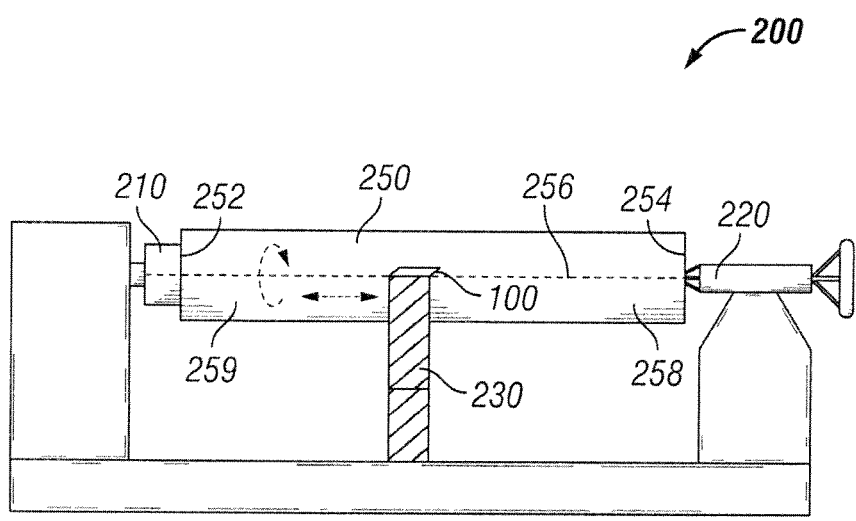
FIG. 2 shows a lathe for testing abrasive wear resistance using a conventional granite log test.
Figure 3:
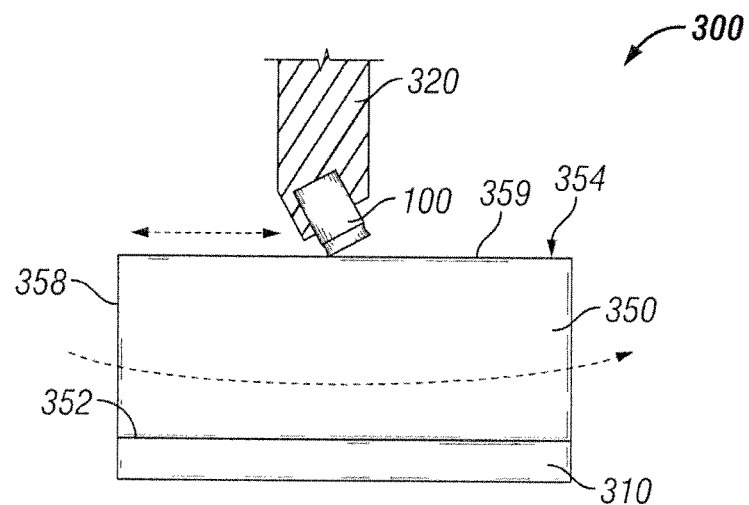
FIG. 3 shows a vertical boring mill for testing abrasive wear resistance using a vertical boring mill test or vertical turret lathe test.
Figure 4:
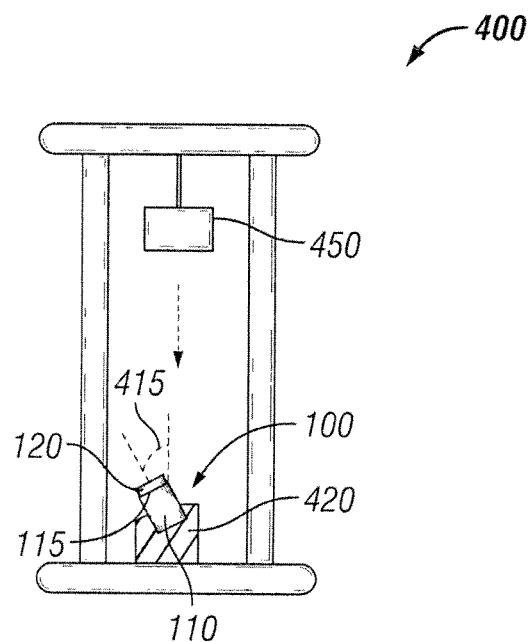
FIG. 4 shows a drop tower apparatus for testing impact resistance of superhard components using a "drop hammer" test.

The cutter 100 has been previously described with respect to FIG. 1 and is applicable to the exemplary embodiments. Briefly, the cutter 100 includes the substrate 110 and the cutter table 120, which is formed or coupled to the top of the substrate 110. In the exemplary embodiment, the cutter table 120 is formed from PCD, but alternative exemplary embodiments have the cutter table 120 fabricated from other materials, such as PCBN, without departing from the scope and spirit of the exemplary embodiment. Although cutter 100 has a planar cutter table 120, or is flat-faced, the cutter table 120 can be dome shaped, concave shaped, or any other shape known to people having ordinary skill in the art.

The cutter 100 includes finished and/or grounded cutters as well as "raw" cutters. "Raw" cutters are unfinished and are cutters that are typically available right out of a pressing cell. Embodiments of the present invention allow testing of both these cutter types. Since cutter manufacturers are able to test "raw" cutters in accordance with embodiments of the present invention, cutter manufacturers are able to insure that they are meeting specification early in a cutter production run. If cutter manufacturers determine that the "raw" cutters 100 are not meeting appropriate specifications, they are able to make the necessary changes in their operating parameters to get "good" cutters before continuing on with the cutter production run. Additionally, "raw" cutters are capable of being tested at a lower kilonewton level, or load, to insure that the "raw" cutters are not cracking under the given load. If cracks are occurring during the testing of the "raw" cutters, cutter manufacturers can forgo the additional expenses associated with finishing and grinding these "raw" cutters; thereby saving unnecessary cost expenditures. Hence, each "raw" cutter is capable of being tested through the acoustic emission testing system 500 using lower load levels to insure that the cutters 100 are "good" cutters.

Referring to FIG. 6, the cutter 100 is inserted within the cavity 720 of the cutter holder 510. The cutter 100 is oriented within the cavity 720 so that the cutter table 120 is facing towards the first surface 712, or away from the second surface 714. According to this exemplary embodiment, the entire cutter 100 is inserted within the cavity 720. However, in alternative exemplary embodiments, a portion of the cutter 100, which includes the entire substrate 110, is completely inserted within the cavity 720. Thus, in these alternative exemplary embodiments, at least a portion of the cutter table 120 is not inserted within the cavity 720. Once the cutter 100 has been inserted within the cavity 720, an air gap 610 is formed between the outer perimeter of the cutter 100 and the outer surface of the cavity 720. According to certain exemplary embodiments, a lubricant 620 is applied to the outer perimeter of the cutter 100 or placed within the cavity 720. In these exemplary embodiments, once the cutter 100 is placed within the cavity 720, the lubricant 620 fills at least a portion of the air gap 610 such that the lubricant 620 adheres to both the outer surface of the cavity 720 and the outer perimeter of the cutter 100 and occupies the portion of the air gap 610 therebetween. In other exemplary embodiments, the lubricant 620 is placed at least between the bottom surface of the cavity 720 and the base of the cutter 100. The lubricant 620 improves acoustic transmission between the cutter 100 and the acoustic sensor 570. The lubricant 620 is a gel, such as an ultrasound gel, according to some exemplary embodiments. However, in alternative exemplary embodiments, other materials can be used as the lubricant 620, which includes, but is not limited to, oils, greases, and lotions. These materials are capable of being spread, adhering to surfaces, and not rapidly drying out. Although the cutter 100 is described as being used in this exemplary embodiment, other hard or superhard materials that desire a toughness testing can be used in lieu of the cutter 100.

Referring back to FIGS. 5 and 6, the indenter 550 is dome shaped at a first end 650 and has a planar surface at a second end 652. The indenter 550 is fabricated to be tougher than the cutter 100 so that once load 580 is applied to the indenter 550, it is the cutter 100 that is damaged and not the indenter 550. For example, the indenter 550 is fabricated from tungsten carbide-cobalt; however, other materials known to those having ordinary skill in the art can be used to fabricate the indenter 550. In certain exemplary embodiments, the cobalt content of the indenter 550 ranges from about six percent to about twenty percent. In certain exemplary embodiments, the cobalt content of the indenter 550 is greater than the cobalt content of the cutter table 120 of the cutter 100. Additionally, in certain exemplary embodiments, a PCD layer is formed or mounted onto the first end 650 of the indenter 550. In these embodiments, the cobalt content of the PCD layer of the indenter 550 is greater than the cobalt content of the cutter table 120 of the cutter 100. Also, in these exemplary embodiments, the cobalt content of the PCD layer of the indenter 550 ranges from about six percent to about twenty percent. Although cobalt is used in these exemplary embodiments to make the indenter tougher than the cutter 100, other components known to people having ordinary skill in the art can be used in alternative exemplary embodiments.

The indenter 550 is sized to fit within the cavity 720 so that it makes contact with the cutter 100. In certain exemplary embodiments, the perimeter of the indenter 550 is sized substantially similar to the perimeter of the cavity 720. However, in the exemplary embodiments where at least a portion of the cutter table 120 is not within the cavity 720, the indenter 550 can be dimensioned such that the perimeter of the indenter 550 is greater than the perimeter of the cavity 720. The indenter 550 is oriented so that the first end 650 makes contact with the cutter 100. Thus, in this embodiment, the PDC layer of the indenter 550 makes contact with the PDC layer, or cutter table 120, of the cutter 100. The load 580 is applied to the second end 652, which transmits the load 580 onto the cutter 100. Although a dome shaped indenter 550 is used in these exemplary embodiments, other exemplary embodiments can use indenters having other shapes, such as a cylindrical shape having a substantially planar surface at both the first end 650 and the second end 652. Also, the second end 652 can be formed into other non-planar shapes without departing from the scope and spirit of the exemplary embodiments.

The acoustic sensor 570 is a piezoelectric sensor that is positioned along the coupling portion 730 of the cutter holder 510. However, the acoustic sensor 570 can be any other device type known to people having ordinary skill in the art, wherein the device is capable of detecting acoustic transmissions. The acoustic sensor 570 detects elastic wave signals formed in the cutter 100, which then converts the elastic waves signal to a voltage signal so that the data can be recorded and subsequently analyzed. In certain exemplary embodiments, the lubricant 620 is placed at the contact area between the coupling portion 730 and the acoustic sensor 570. As previously mentioned, the lubricant 620 improves detection of elastic wave transmission from the cutter 100 to the acoustic sensor 570. According to some alternative exemplary embodiments, the acoustic sensor 570 is sized so that it is capable of being placed on the arcuate portion of the side surface 716. The acoustic sensor 570 is communicably coupled to the data recorder 590 so that the voltage signal derived from the elastic waves occurring within the cutter 100 can be stored and subsequently analyzed. The acoustic sensor 570 is coupled to the data recorder 590 using a cable 592; however, according to other exemplary embodiments, the acoustic sensor 570 can be communicably coupled to the data recorder 590 wirelessly using wireless technology including, but not limited to, infrared and radio frequency.

The data recorder 590 records the data sent from the acoustic sensor 570 and stores the data therein. In certain exemplary embodiments, the apparatus (not shown), or machine, delivering the load 580 also is coupled to the data recorder 590 using a cable 582; however, according to other exemplary embodiments, the apparatus delivering the load 580 can be communicably coupled to the data recorder 590 wirelessly using wireless technology including, but not limited to, infrared and radio frequency. The data recorder 590 also processes and analyzes the data that it receives. Although the data recorder 590 records, stores, processes, and analyzes the data, the data recorder 590 can receive the data, process the data, and analyze the data without storing the data according to some exemplary embodiments. Alternatively, in other exemplary embodiments, the data recorder 590 can store the data but not process or analyze the data. In some exemplary embodiments, an additional device (not shown) is used to process and analyze the data.

Figure 10:
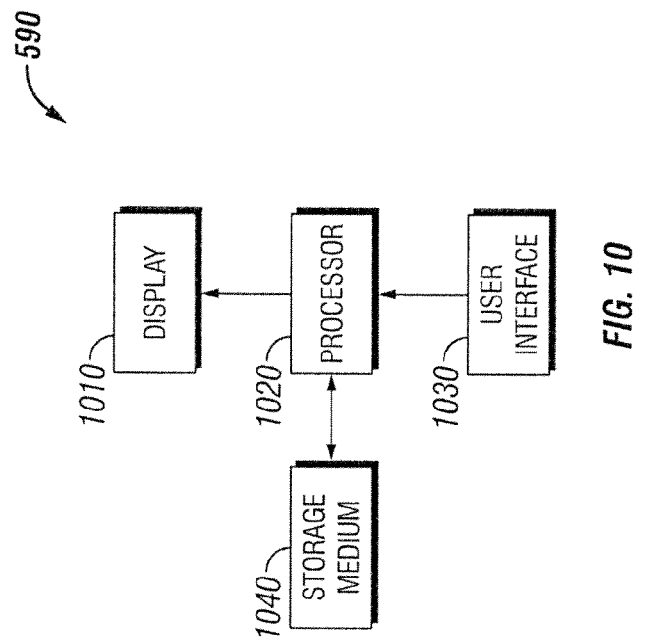
FIG. 10 shows a schematic block diagram of a data recorder of FIG. 5 in accordance with an exemplary embodiment.

FIG. 10 shows a schematic block diagram of a data recorder 590 of FIG. 5 in accordance with an exemplary embodiment. Referring to FIGS. 5 and 10, the data recorder 590 is a computer system. The data recorder 590 includes a storage medium 1040, a user interface 1030, a processor 1020, and a display 1010.

The storage medium 1040 receives information from the acoustic sensor 570 (FIG. 5) and records the information therein. The storage medium 1040 is a hard drive according to one exemplary embodiment. However, according to other exemplary embodiments, the storage medium 1040 includes at least one of a hard drive, a portable hard drive, a USB drive, a DVD, a CD, or any other device capable of storing data and/or software. In some exemplary embodiments, the storage medium 1040 also includes a software for providing instructions on how to process the information, or data, received from the acoustic sensor 570 (FIG. 5).

The user interface 1030 allows a user to interface with the data recorder 590 and provide instructions for operating the data recorder 590. According to some exemplary embodiments, the user interface includes a keyboard. However, according to other exemplary embodiments, the user interface includes at least one of a keyboard, a mouse, a touch screen which can be part of the display 1010, or any other user interface known to people having ordinary skill in the art.

The processor 1020 is capable of receiving instructions from the user interface 1030, accessing information stored within the storage medium 1040, sending information to the storage medium 1040, and sending information to the display 1010. In some exemplary embodiments, the processor 1020 accesses the software that resides within the storage medium 1040 and executes the set of instructions provided by the software. A more detailed description of these instructions are provided further below. In some exemplary embodiments, the processor 1020 includes processor engines 2200, which are described in further detail below in conjunction with FIGS. 16, 17, 18, and 22.

The display 1010 receives information from the processor and communicates this information to the user. According to one exemplary embodiment, the display 1010 includes a monitor, or screen. However, according to other exemplary embodiments, the display 1010 includes at least one of a screen, a touch screen, a printer, or any other device capable of communicating information to the user.

Although not illustrated in FIG. 10, the data recorder 590 can be communicably coupled, either wired or wirelessly, to an internal network, wherein the software and/or data from the acoustic sensor 570 (FIG. 5) is stored in a central server (not shown). Additionally, according to some alternative exemplary embodiments, the data recorder 590 can be communicably coupled, either wired or wirelessly, to a modem (not shown), wherein the modem is communicably coupled to the world wide web. In certain alternative exemplary embodiments, the software and/or data from the acoustic sensor 570 (FIG. 5) is stored in a remote location that is accessible via the world wide web.

Figure 8:
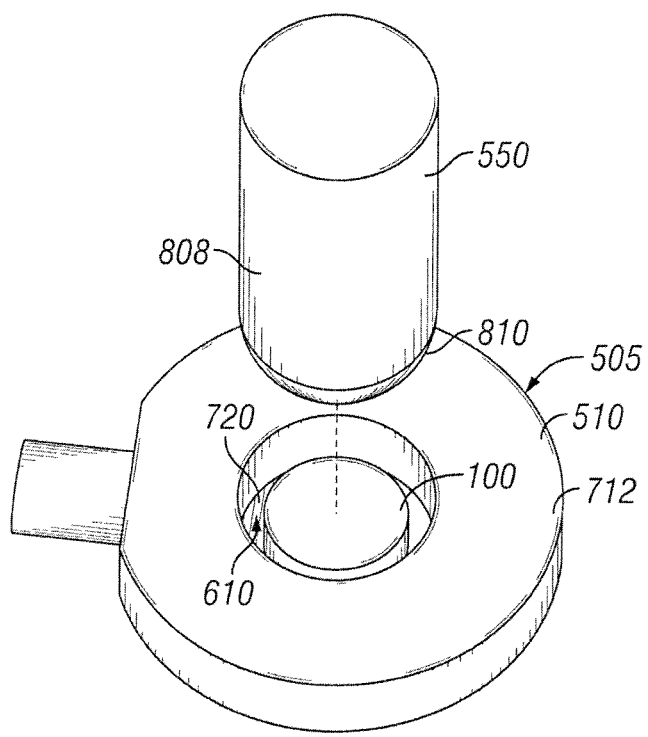
FIG. 8 shows a perspective view of the acoustic emission testing device of FIG. 5 with the indenter being removed from the cutter holder in accordance with an exemplary embodiment of the present invention.

FIG. 8 shows a perspective view of the acoustic emission testing device 505 of FIG. 5 with the indenter 550 being removed from the cutter holder 510 in accordance with an exemplary embodiment of the present invention. Referring to FIG. 8, the cutter 100 is fully inserted within the cavity 720 of the cutter holder 510. As shown, the diameter of the cutter 100 is less than the diameter of the cavity 720, thereby forming the air gaps 610. Also, the PDC layer, or the cutter table 120, is oriented within the cavity 720 so that the PCD layer faces towards the first surface 712. The indenter 550 is removed from the cavity 720 to further illustrate some features of the indenter 550. According to this exemplary embodiment, the indenter 550 includes a substrate 808 and a hard surface 810, which is formed or coupled to the top of the substrate 808. In the exemplary embodiment, the hard surface 810 is formed from PCD, but alternative exemplary embodiments can have the hard surface 810 fabricated from other hard or superhard materials, such as PCBN, without departing from the scope and spirit of the exemplary embodiment. Although indenter 550 has a dome shaped hard surface 810, the hard surface 810 can be planar or any other shape known to people having ordinary skill in the art. As seen, the indenter 550 has a diameter substantially similar to the diameter of the cavity 720, according to this exemplary embodiment.

In an alternative embodiment, the indenter 550 is positioned within the cavity 720 having the hard surface 810 facing towards the first surface 712. The cutter 100 to be tested is positioned on top of the indenter 550 with the cutter table 120 contacting the hard surface 810. The load 580 is applied downward on the back face of the substrate 110 of the test cutter 100. Acoustic emissions of cracks initiated and/or propagated in the test cutter 100 is transmitted through the indenter 550 and to the acoustic sensor 570. In this alternative exemplary embodiment, the cutter holder 510 is optional.

Figure 9:
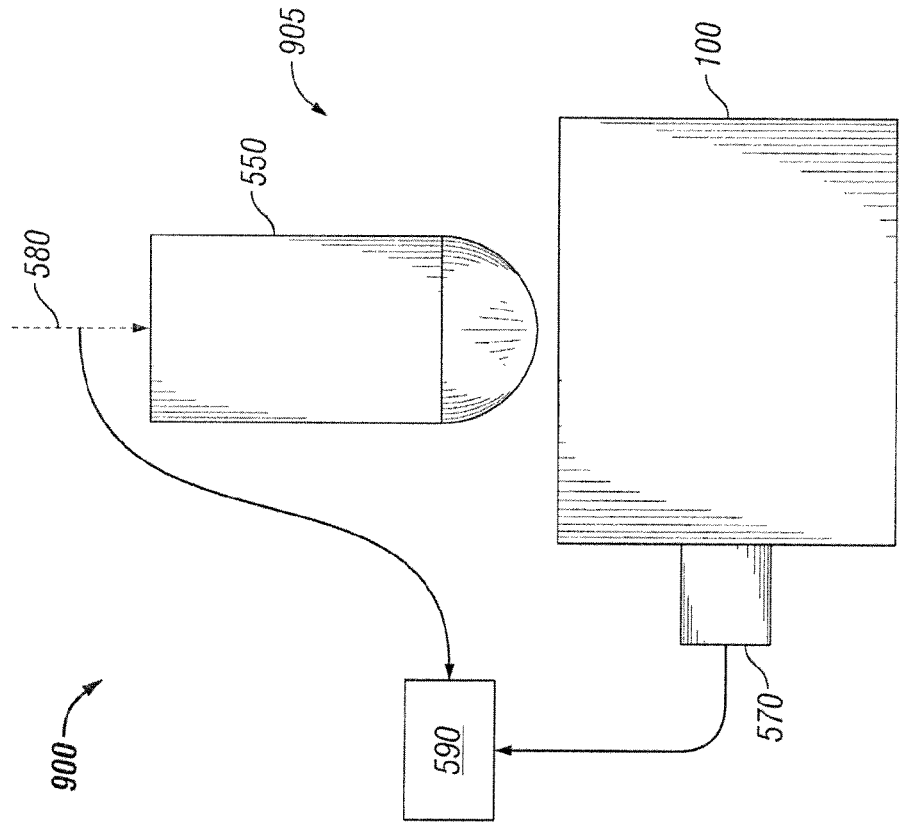
FIG. 9 shows a perspective view of an acoustic emission testing system in accordance with an alternative exemplary embodiment of the present invention.

FIG. 9 shows a perspective view of an acoustic emission testing system 900 in accordance with an alternative exemplary embodiment of the present invention. Referring to FIG. 9, the acoustic emission testing system 900 includes an acoustic emission testing device 905 communicably coupled to the data recorder 507. The acoustic emission testing device 905 is similar to the acoustic emission testing device 505 of FIG. 5, except that the acoustic sensor 570 is directly coupled to the cutter 100 and the cutter holder 510 of FIG. 5 is removed. The cutter 100, the indenter 550, the load 580, the acoustic sensor 570, and the data recorder 590 have been previously described with respect to FIGS. 5, 6, 7, 8, and 10. Also, the lubricant 620 (FIG. 6) is placed between the acoustic sensor 570 and the cutter 100 according to some exemplary embodiments.

The operation of the acoustic emission testing system 500 is described while referring to FIGS. 5-8. The cutter 100, or hard or superhard material, to be tested is placed within the cavity 720 of the cutter holder 510. To improve the elastic wave transmission across the contacting surfaces between the base, or bottom surface, of the cutter 100 and the base of the cavity 720, a mineral oil based gel 620 is used between the bottom surface of the cutter 100 and the base of the cavity 720. The acoustic sensor 570 is positioned against the coupling portion 730 of the cutter holder 510 to detect the elastic waves generated within the cutter 100. To improve the elastic wave transmission across the contacting surfaces between the acoustic sensor 570 and the coupling portion 730, the mineral oil based gel 620 also is used between the acoustic sensor 570 and the coupling portion 730. The indenter 550 is placed on top of the PCD layer 120 of the cutter 100 and is pushed against this PCD layer 120 using the load 580. The load 580 is provided on the indenter 550 using a 100 kilonewton 8500 series Instron machine. This machine (not shown) is capable of controlling the amount of load that is exerted on the indenter 550. The machine is hooked up to the data recorder 590 so that load versus time is measured. Although one example of a machine capable of providing the load 580 is disclosed, any system capable of providing a measurable load to the indenter 550 is in the scope of exemplary embodiments for this invention. For example, the machine or apparatus for delivering the measurable load 580 can range from a handheld hammer to a fully instrumented impact machine or to a load controlled hydraulic machine for steady ramp or cyclic loading histories.

The load 580 is applied onto the indenter 550 and increased at a constant rate to a desired load level. Once reaching the desired load level, the load level is maintained for a desired period of time, which can range from a few seconds to several minutes, and then ramped down at a faster rate than the ramp up rate. Each time a new crack forms or an existing crack grows within the top diamond layer 130, a certain amount of elastic energy is released almost instantaneously in the form of a train of elastic waves travelling through the PCD layer 120, the substrate 110, and the cutter holder 510. The acoustic sensor 570 detects these elastic waves and converts the received signals into a voltage signal. The acoustic sensor 570 is communicably coupled to the data recorder 590 so that acoustic emissions, or data, are recorded against time. These acoustic emissions include background noise and acoustic events. Hence, since the acoustic emissions history and the loading history is recorded onto the data recorder 590, one can determine at what load 580 certain acoustic events occurred. An acoustic event is an event where a new crack forms or when an existing crack grows in the PDC layer 120. According to one exemplary embodiment, the acoustic sensor 570 provides data to the data recorder 590 at about 5,000 data points per second; however, the data points per second can be increased or decreased without departing from the scope and spirit of the exemplary embodiment.

Figure 11:
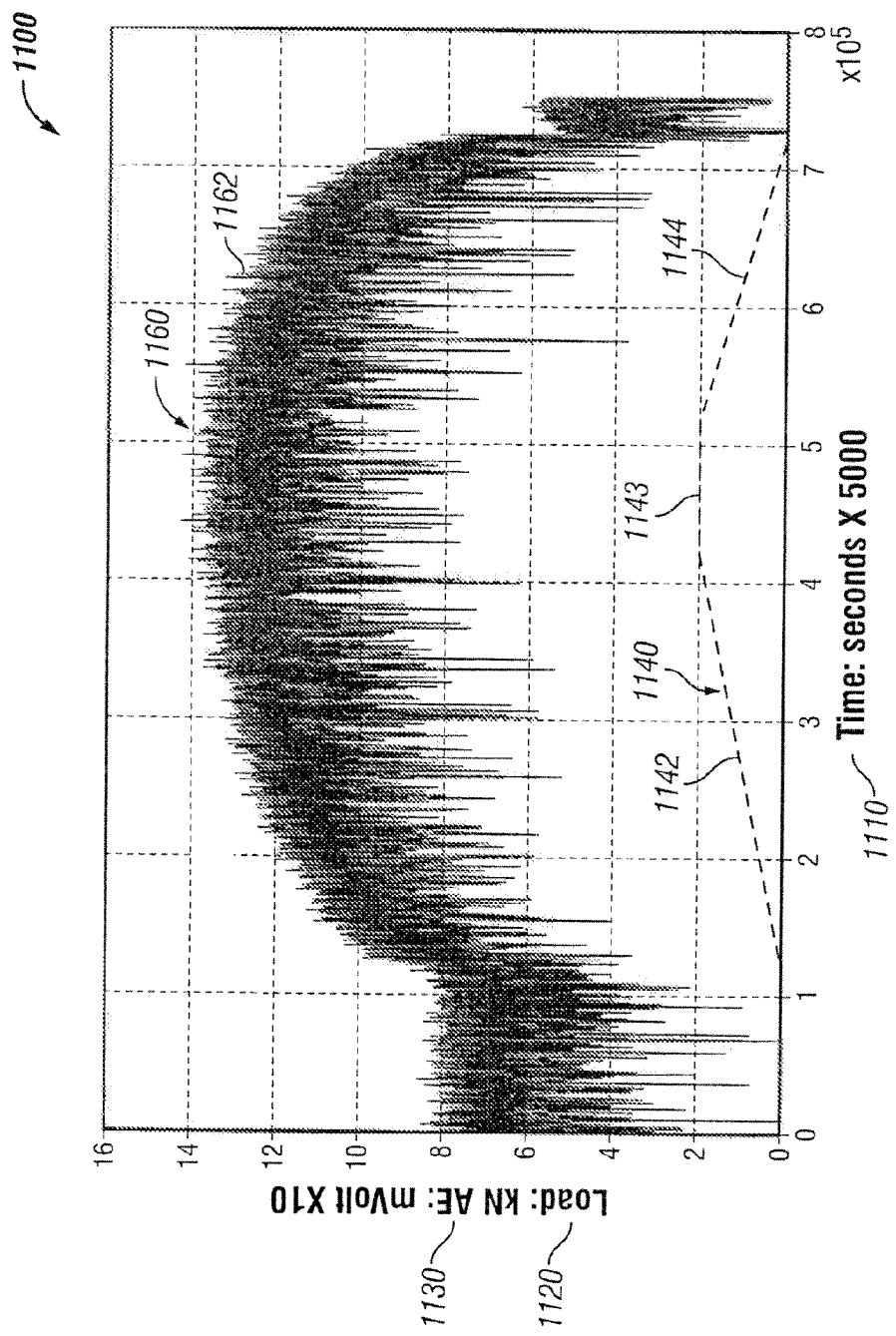
FIG. 11 shows a graphical cutter acoustic emission and loading representation for a cutter experiencing a load of up to about two kilonewtons in accordance with an exemplary embodiment of the present invention.

FIG. 11 shows a graphical cutter acoustic emission and loading representation 1100 for a cutter experiencing a load of up to about two kilonewtons in accordance with an exemplary embodiment of the present invention. Referring to FIG. 11, the cutter acoustic emission and loading representation 1100 includes a time axis 1110, a load axis 1120, and an acoustic emissions axis 1130. The time axis 1110 is represented by an x-axis and is provided with units in the seconds times 5,000. Thus, to obtain the time period in seconds, the numerical value in the time axis 1110 is to be divided by 5,000. The time axis 1110 can also be read as energy being delivered to the sample. In other words, as more time passes, more total energy is exerted on the cutter or test sample. The load axis 1120 is represented by a y-axis and is provided with units in the kilonewtons. The acoustic emissions axis 1130 also is represented by the y-axis and is provided with units in the millivolts times ten. Thus, to obtain the voltage in millivolts, the numerical value in the acoustic emissions axis 1130 is to be divided by ten. A load curve 1140 and an acoustic emissions curve 1160 are both illustrated on the cutter acoustic emission and loading representation 1100. According to the load curve 1140, the load was increased from zero kilonewtons to two kilonewtons at a constant rate 1142, or ramp up rate. The load was held at a peak load level 1143, or two kilonewtons in this example, for a period of time and then ramped down at a ramp down rate 1144, which is faster than the ramp up rate 1142. The acoustic emissions curve 1160 represents the recorded signal from the acoustic sensor. According to the acoustic emissions curve 1160, the only acoustic emissions recorded is a background noise 1162. There were no acoustic events that were detected. Also, as the load increases, the background noise 1162 also increases.

Figure 12:
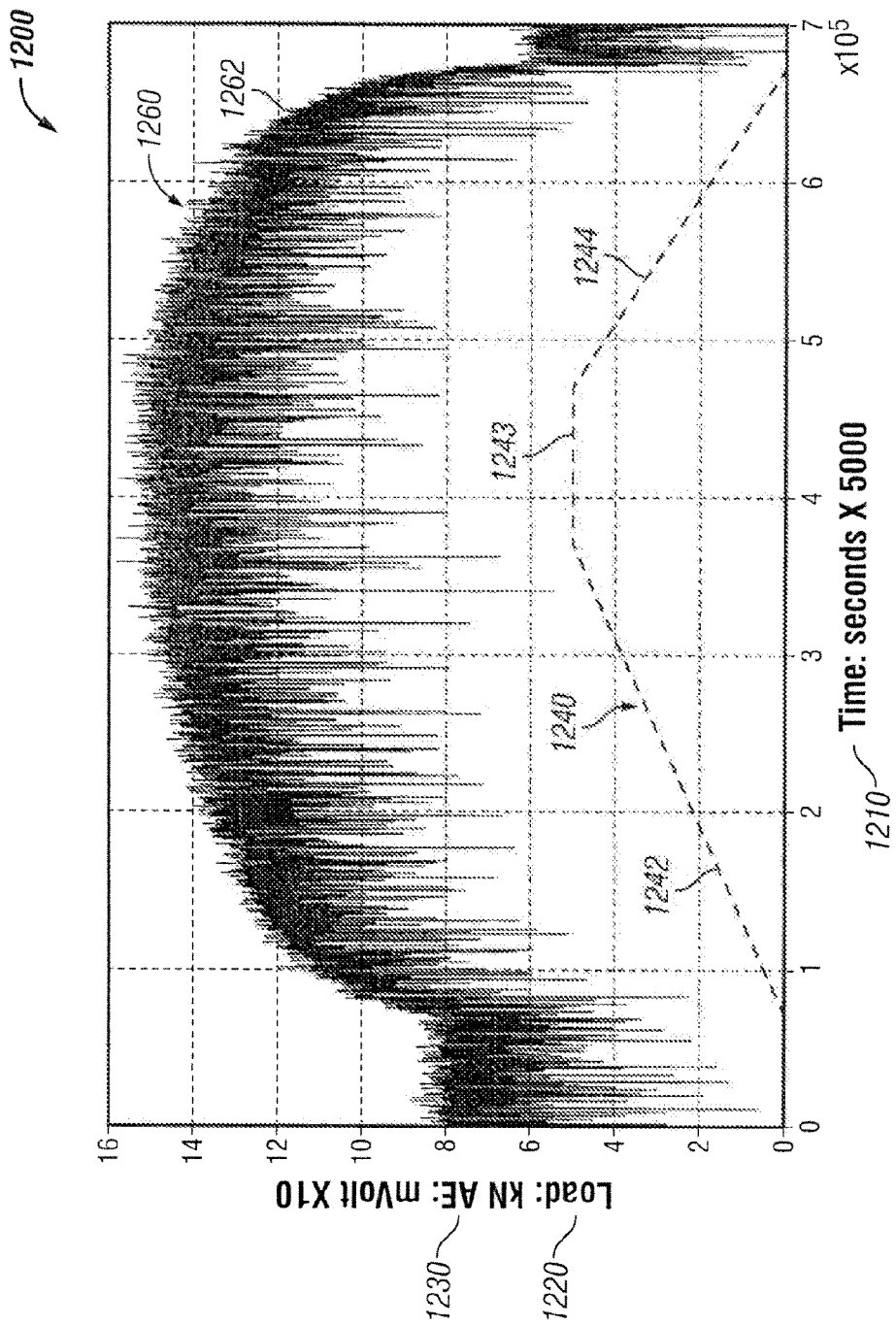
FIG. 12 shows a graphical cutter acoustic emission and loading representation for a cutter experiencing a load of up to about five kilonewtons in accordance with an exemplary embodiment of the present invention.

FIG. 12 shows a graphical cutter acoustic emission and loading representation 1200 for a cutter experiencing a load of up to about five kilonewtons in accordance with an exemplary embodiment of the present invention. Referring to FIG. 12, the cutter acoustic emission and loading representation 1200 includes a time axis 1210, a load axis 1220, and an acoustic emissions axis 1230. The time axis 1210 is represented by an x-axis and is provided with units in the seconds times 5,000. Thus, to obtain the time period in seconds, the numerical value in the time axis 1210 is to be divided by 5,000. The time axis 1210 can also be read as energy being delivered to the sample. In other words, as more time passes, more total energy is exerted on the cutter or test sample. The load axis 1220 is represented by a y-axis and is provided with units in the kilonewtons. The acoustic emissions axis 1230 also is represented by the y-axis and is provided with units in the millivolts times ten. Thus, to obtain the voltage in millivolts, the numerical value in the acoustic emissions axis 1230 is to be divided by ten. A load curve 1240 and an acoustic emissions curve 1260 are both illustrated on the cutter acoustic emission and loading representation 1200. According to the load curve 1240, the load was increased from zero kilonewtons to five kilonewtons at a constant rate 1242, or ramp up rate. The load was held at a peak load level 1243, or five kilonewtons in this example, for a period of time and then ramped down at a ramp down rate 1244, which is faster than the ramp up rate 1242. The acoustic emissions curve 1260 represents the recorded signal from the acoustic sensor. According to the acoustic emissions curve 1260, the only acoustic emissions recorded is a background noise 1262. There were no acoustic events that were detected. Also, as the load increases, the background noise 1262 also increases.

Figure 13:
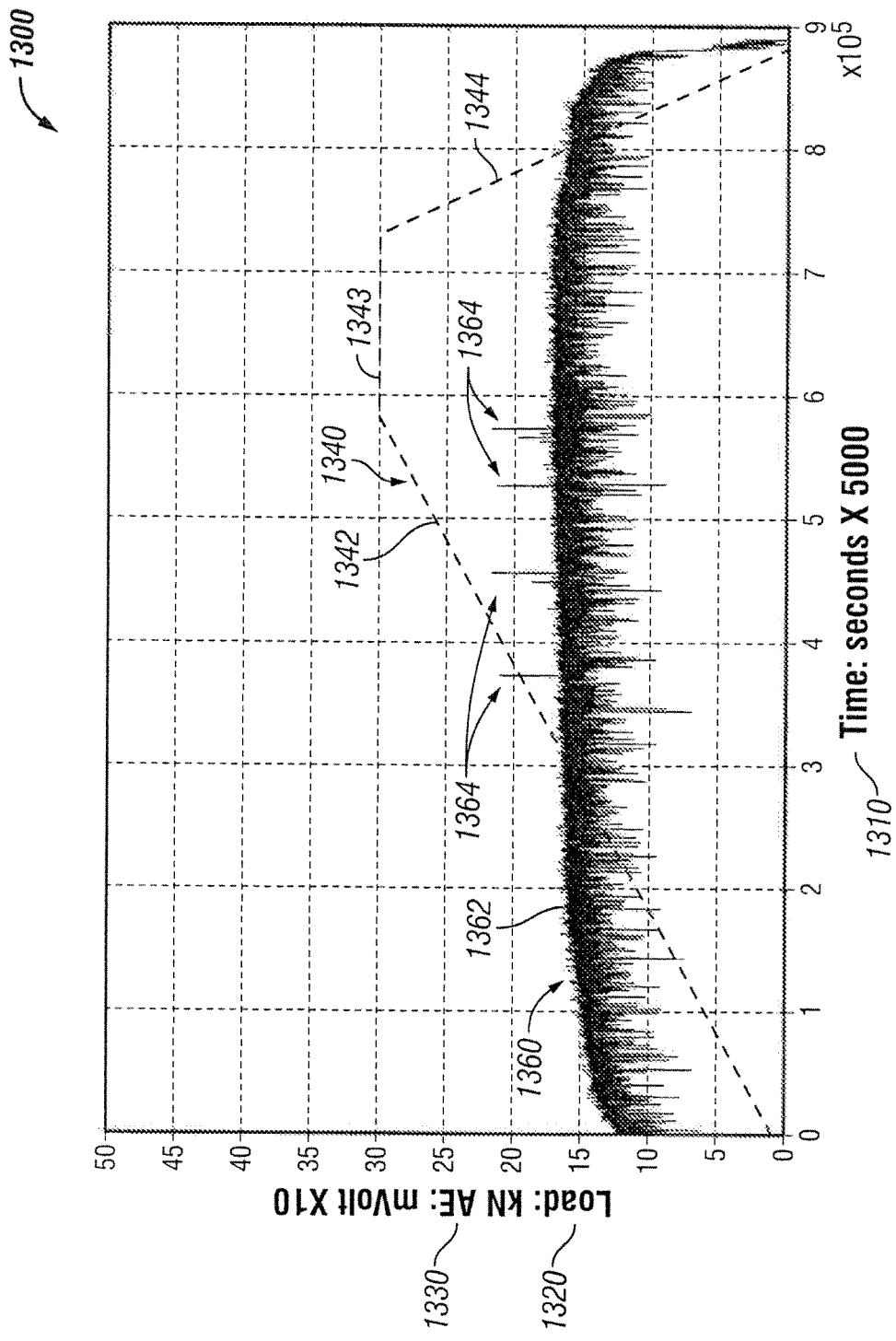
FIG. 13 shows a graphical cutter acoustic emission and loading representation for a cutter experiencing a load of up to about thirty kilonewtons in accordance with an exemplary embodiment of the present invention.

FIG. 13 shows a graphical cutter acoustic emission and loading representation 1300 for a cutter experiencing a load of up to about thirty kilonewtons in accordance with an exemplary embodiment of the present invention. Referring to FIG. 13, the cutter acoustic emission and loading representation 1300 includes a time axis 1310, a load axis 1320, and an acoustic emissions axis 1330. The time axis 1310 is represented by an x-axis and is provided with units in the seconds times 5,000. Thus, to obtain the time period in seconds, the numerical value in the time axis 1310 is to be divided by 5,000. The time axis 1310 can also be read as energy being delivered to the sample. In other words, as more time passes, more total energy is exerted on the sample. The load axis 1320 is represented by a y-axis and is provided with units in the kilonewtons. The acoustic emissions axis 1330 also is represented by the y-axis and is provided with units in the millivolts times ten. Thus, to obtain the voltage in millivolts, the numerical value in the acoustic emissions axis 1330 is to be divided by ten. A load curve 1340 and an acoustic emissions curve 1360 are both illustrated on the cutter acoustic emission and loading representation 1300. According to the load curve 1340, the load was increased from zero kilonewtons to thirty kilonewtons at a constant rate 1342, or ramp up rate. The load was held at a peak load level 1343, or thirty kilonewtons in this example, for a period of time and then ramped down at a ramp down rate 1344, which is faster than the ramp up rate 1342. The acoustic emissions curve 1360 represents the recorded signal from the acoustic sensor. According to the acoustic emissions curve 1360, the acoustic emissions recorded includes a background noise 1362 and one or more acoustic events 1364. The background noise 1362 makes up the bulk of the data recorded during the test. The acoustic events 1364 are shown as thin vertical lines that significantly extend upwards from the background noise 1362. The height of each acoustic event 1364 above the background noise 1362 is proportional to the amount of elastic energy released by each cracking formation and/or propagation event by means of a calibration constant. Every single acoustic event 1364 lasts on average about fifty milliseconds. According to this exemplary embodiment, the acoustic sensor samples about 5,000 data points per second, which allows detection of these acoustic events 1364. Also, as the load increases, the background noise 1362 also increases. After completing this test, the cutter was visually examined. Although there were no visual signs of any damage on the top PCD surface of the cutter, the acoustic sensor did detect acoustic events occurring within the cutter. Thus, the acoustic sensor is able to detect minimal damage occurring to the cutters once exposed to a load even though the damage is not visible.

Figure 14:
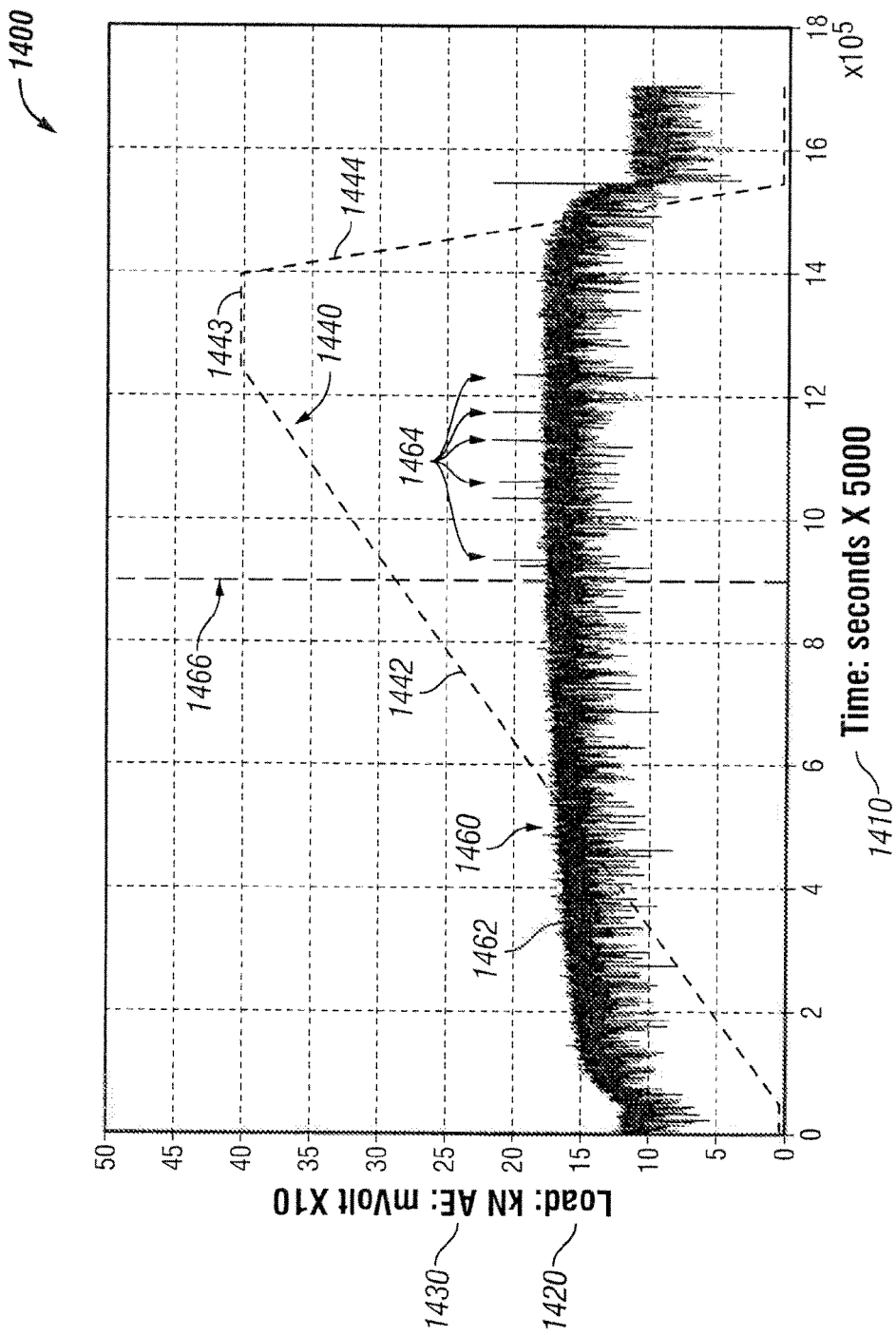
FIG. 14 shows a graphical cutter acoustic emission and loading representation for a cutter experiencing a load of up to about forty kilonewtons in accordance with an exemplary embodiment of the present invention.

FIG. 14 shows a graphical cutter acoustic emission and loading representation for a cutter experiencing a load of up to about forty kilonewtons in accordance with an exemplary embodiment of the present invention. The same cutter sample used in the tests represented in FIG. 13 was used in the test represented in FIG. 14. Referring to FIG. 14, the cutter acoustic emission and loading representation 1400 includes a time axis 1410, a load axis 1420, and an acoustic emissions axis 1430. The time axis 1410 is represented by an x-axis and is provided with units in the seconds times 5,000. Thus, to obtain the time period in seconds, the numerical value in the time axis 1410 is to be divided by 5,000. The time axis 1410 can also be read as energy being delivered to the sample. In other words, as more time passes, more total energy is exerted on the sample. The load axis 1420 is represented by a y-axis and is provided with units in the kilonewtons. The acoustic emissions axis 1430 also is represented by the y-axis and is provided with units in the millivolts times ten. Thus, to obtain the voltage in millivolts, the numerical value in the acoustic emissions axis 1430 is to be divided by ten. A load curve 1440 and an acoustic emissions curve 1460 are both illustrated on the cutter acoustic emission and loading representation 1400. According to the load curve 1440, the load was increased from zero kilonewtons to forty kilonewtons at a constant rate 1442, or ramp up rate. The load was held at a peak load level 1443, or forty kilonewtons in this example, for a period of time and then ramped down at a ramp down rate 1444, which is faster than the ramp up rate 1442. The acoustic emissions curve 1460 represents the recorded signal from the acoustic sensor. According to the acoustic emissions curve 1460, the acoustic emissions recorded includes a background noise 1462 and one or more acoustic events 1464. The acoustic events 1464 are shown as vertical lines that significantly extend upwards from the background noise 1462. The height of each acoustic event 1464 above the background noise 1462 is proportional to the amount of elastic energy released by each cracking formation and/or propagation event by means of a calibration constant. As seen in FIG. 14, acoustic events 1464 did not occur within the cutter until the load reached or exceeded the previous load that was exposed to this cutter. For example, this cutter previously experienced loads up to thirty kilonewtons as described in FIG. 13. Thus, new acoustic events 1464 did not arise until the load reached and/or exceeded a threshold 1466, which was about thirty kilonewtons in this example, that was previously applied on to the cutter. Based upon the experiments, it seems that to generate new cracks or to grow existing cracks in the cutter that were formed in a previous test run, a load level equal to or higher than the previous peak load level 1343 is to be applied.

Figure 15A:
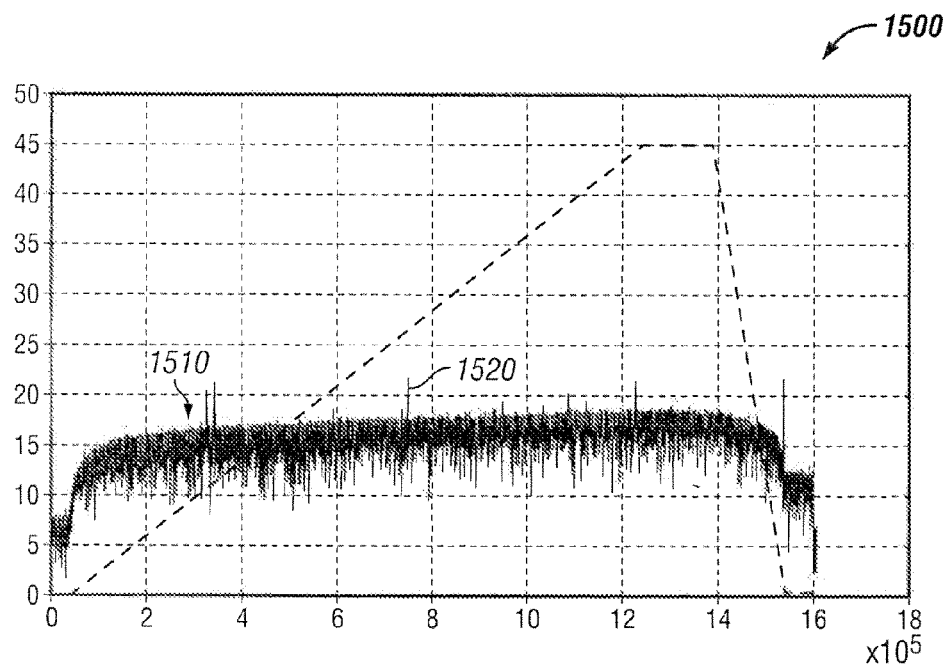
FIG. 15A shows a graphical cutter acoustic emission and loading representation for a cutter manufacturer #1 cutter sample #1 cutter type experiencing a load of up to about forty-five kilonewtons in accordance with an exemplary embodiment of the present invention.
Figure 15B:
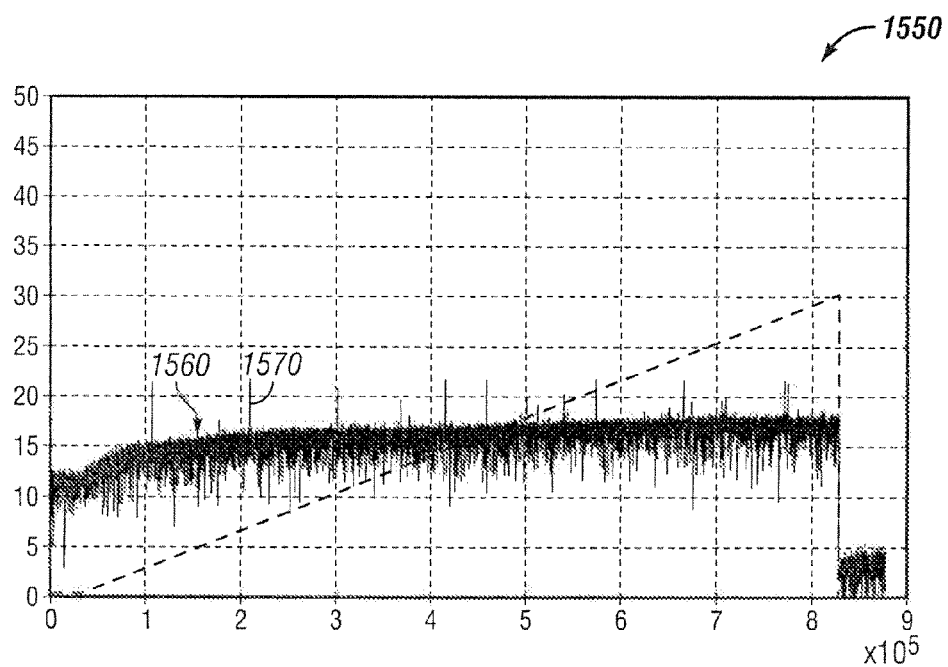
FIG. 15B shows a graphical cutter acoustic emission and loading representation for a cutter manufacturer #2 cutter sample #2 cutter type experiencing a load of up to about thirty kilonewtons in accordance with an exemplary embodiment of the present invention.

FIG. 15A shows a graphical cutter acoustic emission and loading representation 1500 for a cutter manufacturer #1 cutter sample #1 cutter type experiencing a load of up to about forty-five kilonewtons in accordance with an exemplary embodiment of the present invention. FIG. 15B shows a graphical cutter acoustic emission and loading representation 1550 for a cutter manufacturer #2 cutter sample #2 cutter type experiencing a load of up to about thirty kilonewtons in accordance with an exemplary embodiment of the present invention. Referring to FIGS. 15A and 15B, the cutter acoustic emission and loading representation 1500 includes an acoustic emission curve 1510 showing one or more acoustic events 1520 occurring within the cutter manufacturer #1 cutter sample #1 cutter type, while the cutter acoustic emission and loading representation 1550 includes an acoustic emission curve 1560 showing one or more acoustic events 1570 occurring within the cutter manufacturer #2 cutter sample #2 cutter type. There are significantly more acoustics events 1520 and 1570 occurring within the cutter manufacturer #2 cutter sample #2 cutter type than in the cutter manufacturer #1 cutter sample #1 cutter type. Thus, different cutter types show different acoustic patterns within their respective acoustic emissions curve. Based upon these results, a user can determine which cutter type is tougher than another cutter type and can thereby rank cutters according to their toughness. In this case, the cutter manufacturer #1 cutter sample #1 cutter type is tougher than the cutter manufacturer #2 cutter sample #2 cutter type.

Based upon the experimental results shown in FIGS. 11-15, there are at least several observations that can be made. First, the acoustic sensor is able to detect crack formation and crack growth within the diamond table of the cutter as the indenter is being loaded and is able to send signals that are subsequently analyzable. Second, different cutter types show different acoustic event patterns and allow a user to rank the toughness of the cutter when compared to another cutter. Third, although there can be no visible damage that is detectable on the surface of the PDC table of the cutter after the test, the acoustic sensor is able to detect any non-visible damage occurring to the cutter.

Figure 16:
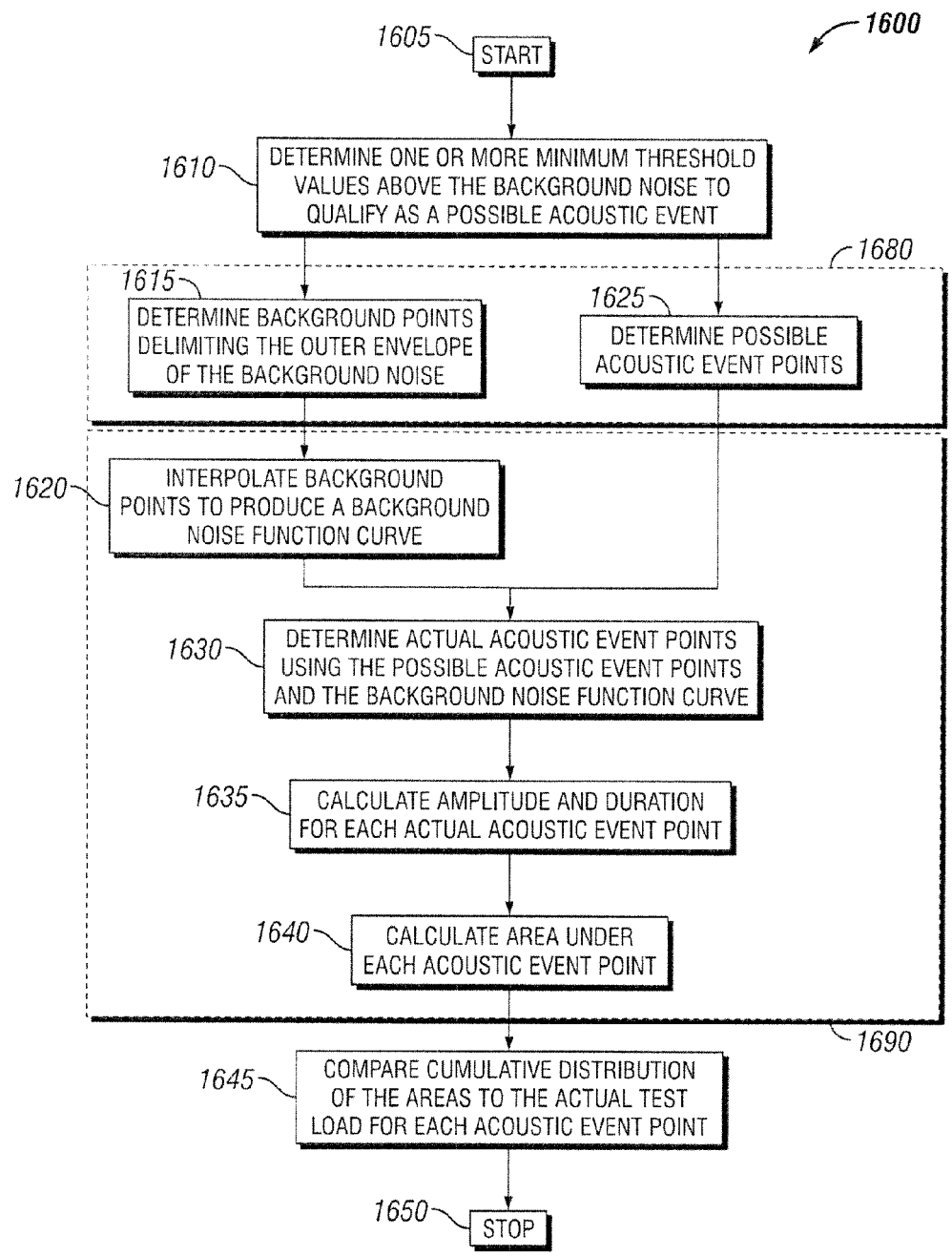
FIG. 16 illustrates a flowchart of a method for analyzing data points received from the acoustic sensor, wherein the method includes a loop one method and a loop two method in accordance with an exemplary embodiment of the present invention.

FIG. 16 illustrates a flowchart of a method 1600 for analyzing data points received from the acoustic sensor, wherein the method includes a loop one method 1680 and a loop two method 1690 in accordance with an exemplary embodiment of the present invention. Although certain steps are shown as proceeding in a particular order, the sequence of steps can be varied without departing from the scope and spirit of the exemplary embodiment. Also, although certain functions are performed in one or more steps, the number of steps for performing that function can be increased or decreased without departing from the scope and spirit of the exemplary embodiment.

Referring to FIG. 16, at step 1605, the method 1600 starts. From step 1605, method 1600 proceed to step 1610. At step 1610, one or more minimum threshold values above the background noise to qualify a data point as a possible acoustic event is determined. Upon completion of step 1610, method 1600 proceeds to step 1615 and step 1625, which can occur simultaneously in certain exemplary embodiments. At step 1615, the background points delimiting the outer envelop of the background noise is determined. At step 1625, the possible acoustic event points is determined based upon the one or more threshold values determined at step 1610. Step 1615 and step 1625 are included in the loop one method 1680, which is described in further detail below in conjunction with FIG. 17.

From step 1615, method 1600 proceeds to step 1620. At step 1620, the background points determined at step 1615 are interpolated to produce a background noise function curve. From steps 1620 and 1625, method 1600 proceeds to step 1630. At step 1630, actual acoustic event points are determined using the possible acoustic event points determined at step 1680 and the background noise function curve determined at step 1620. From step 1630, method 1600 proceeds to step 1635. At step 1635, the amplitude and duration of each actual acoustic event point is determined. From step 1635, method 1600 proceeds to step 1640. At step 1640, the area under each acoustic event point is calculated. From step 1640, method 1600 proceeds to step 1645. At step 1645, the cumulative distribution of the areas is compared to the actual test load for each acoustic event point. A user can use this comparison to make a determination as to the relative toughness of one cutter to another cutter. This comparison allows the determination to be made using a quantitative and objective methods. The duration, amplitude, and frequency of the acoustic event points and the corresponding level of energy, or load, delivered to the sample can be correlated directly with the field impact performance of the PCD, or other hard or superhard material, being tested. Method 1600 allows measurement of not only the smallest amount of external work, or load, required to initiate some damage but also allows measurement of the amount of additional work, or load, that has to be done to increase the damage level. After step 1645, method 1600 proceed to step 1650 where method 1600 is stopped.

Figure 19:
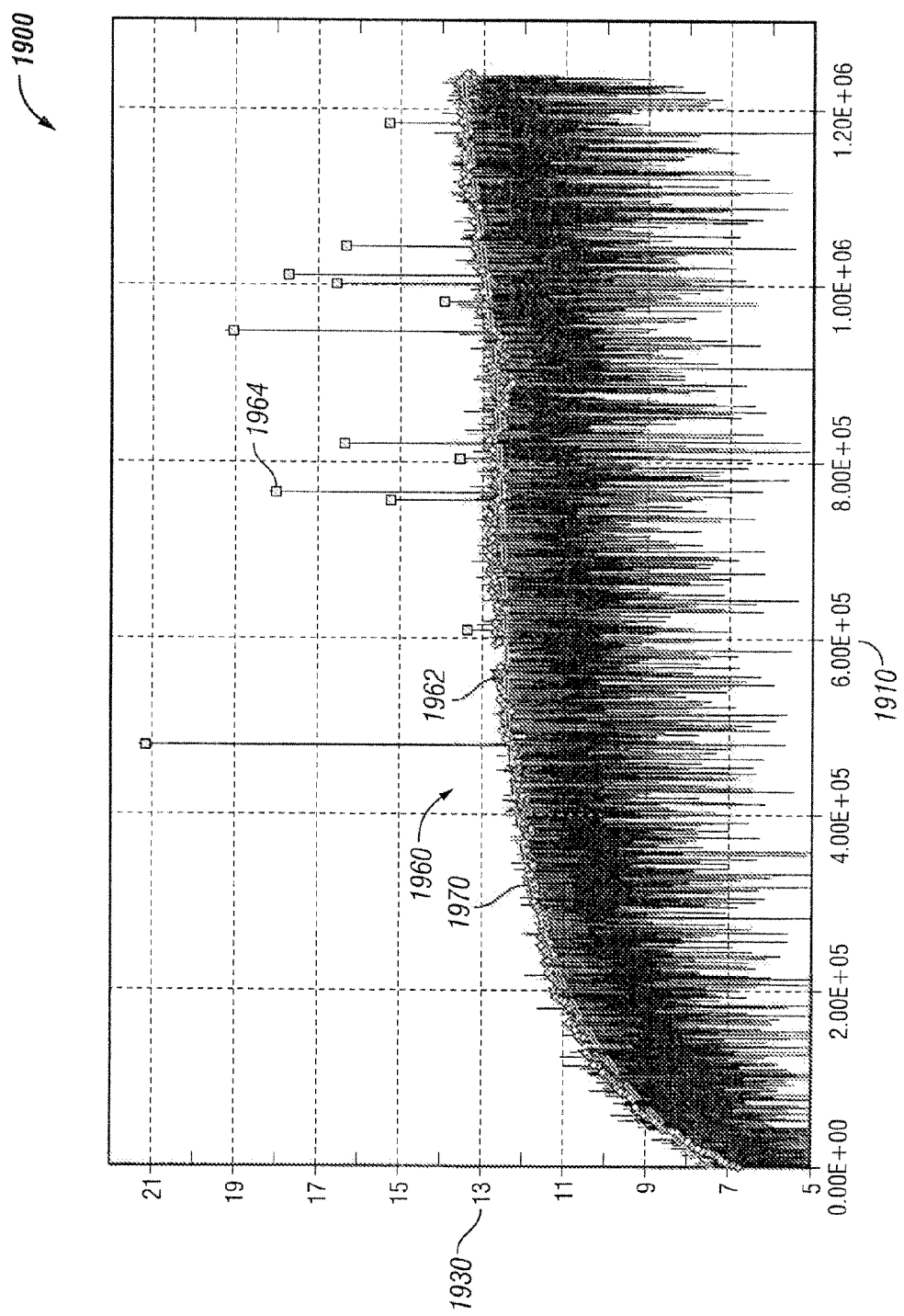
FIG. 19 shows a graphical cutter acoustic emission representation for a cutter experiencing a load in accordance with an exemplary embodiment of the present invention.
Figure 20:
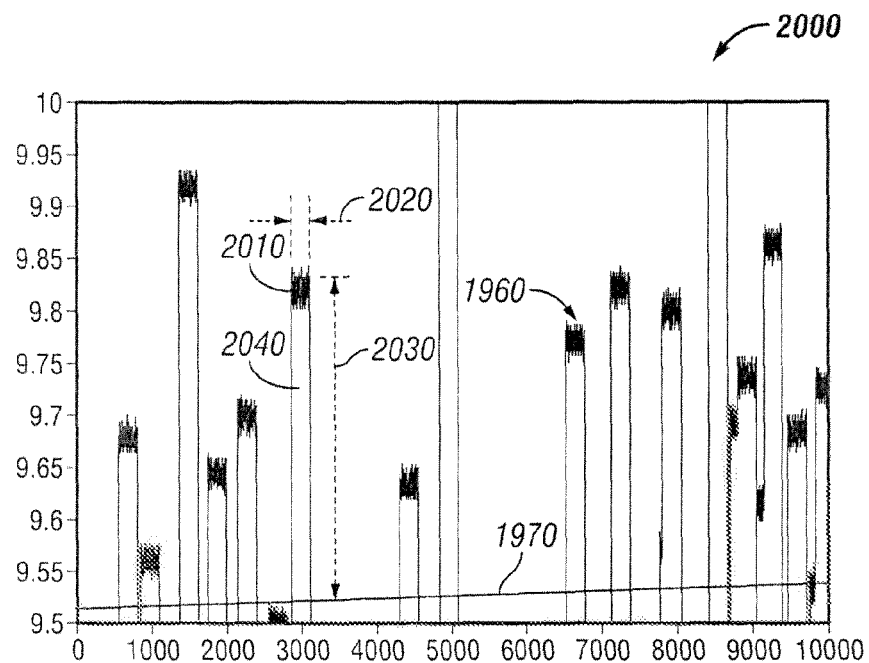
FIG. 20 shows a magnified view of a portion of a graphical cutter acoustic emission representation for a cutter experiencing a load in accordance with an exemplary embodiment of the present invention.
Figure 21:
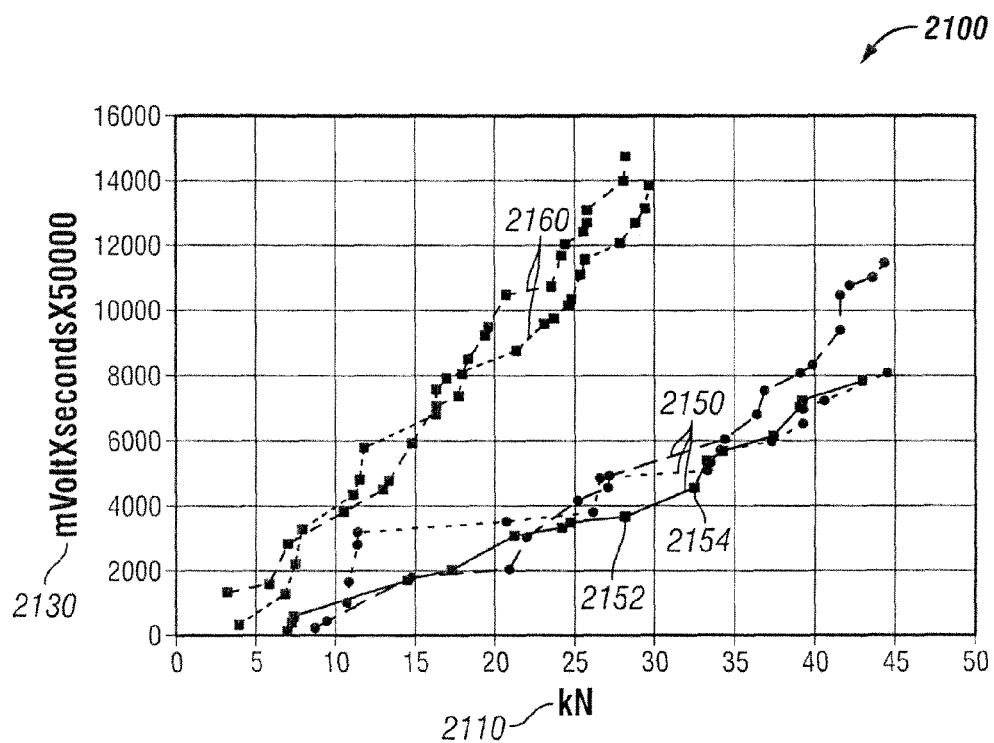
FIG. 21 shows a cumulative distribution representation for each actual acoustic event in accordance with an exemplary embodiment of the present invention.

FIG. 19 shows a graphical cutter acoustic emission representation 1900 for a cutter experiencing a load in accordance with an exemplary embodiment of the present invention. FIG. 20 shows a magnified view of a portion of a graphical cutter acoustic emission representation 2000 for a cutter experiencing a load in accordance with an exemplary embodiment of the present invention. FIG. 21 shows a cumulative distribution representation 2100 for each actual acoustic event in accordance with an exemplary embodiment of the present invention. FIGS. 19-21 depict a majority of the steps illustrated in method 1600 of FIG. 16.

Referring to FIG. 19, the cutter acoustic emission representation 1900 includes a time axis 1910 and an acoustic emissions axis 1930. The time axis 1910 is represented by an x-axis and is provided with units in the seconds times 5,000. Thus, to obtain the time period in seconds, the numerical value in the time axis 1910 is to be divided by 5,000. The acoustic emissions axis 1930 is represented by a y-axis and is provided with units in the millivolts time ten. Thus, to obtain the voltage in millivolts, the numerical value in the acoustic emissions axis 1930 is to be divided by ten. An acoustic emissions data 1960 is illustrated on the cutter acoustic emission representation 1900. The acoustic emissions data 1960 represents the recorded signal from the acoustic sensor. According to the acoustic emissions data 1960, the acoustic emissions data recorded includes one or more background points 1962 and one or more possible acoustic event points 1964. Referring to FIGS. 16 and 19 and according to step 1615 and step 1625 of FIG. 16, the acoustic emissions data 1960 is sorted to include background points 1962 and possible acoustic event points 1964. The sorting of the acoustic emissions data 1960 is performed using an algorithm that resides within data recorder 590 (FIG. 5) according to one exemplary embodiment. However, the algorithm can be stored in another device in alternative exemplary embodiments or is performed manually. Alternatively, other methods known to people having ordinary skill in the art and having the benefit of the present disclosure can be used to categorize the acoustic emissions data 1960. As shown in FIG. 19, each background point 1962 is marked with a circle and each possible acoustic event point 1964 is marked with a square. There are some points that are not defined as either a background point 1962 or a possible acoustic event point 1964. These markings are for illustrative purposes and is not meant to limit the scope of exemplary embodiments of the present invention.

Referring to FIGS. 16 and 19 and according to step 1620 of FIG. 16, a background noise function curve 1970 is interpolated using the determined background points 1962. According to one exemplary embodiment, the background noise function curve 1970 is interpolated using a fourth degree polynomial; however, other degrees of polynomial can be used to interpolate the background points 1962 without departing from the scope and spirit of the exemplary embodiment.

Referring to FIG. 20, a magnified portion of the graphical cutter acoustic emission representation 2000 is presented. According to this figure, each acoustic emissions data 1960, which includes the actual acoustic event points 2010, has a time duration 2020 that it occurs in. Additionally, each actual acoustic event point 2010, has an amplitude 2030 that is measured vertically from the background noise function curve 1970 to the position where the actual acoustic event point 2010 lies. Referring to FIGS. 16 and 20 and according to step 1635 of FIG. 16, the amplitude 2030 and the time duration 2020 of the actual acoustic event point 2010 is calculated. Once the amplitude 2030 and the time duration 2020 is determined, the area 2040 under each actual acoustic event point 2010 is calculated by multiplying the amplitude 2030 to the time duration 2020. This step is accomplished in step 1640 of FIG. 16. According to some of the exemplary embodiments, the units for the area 2040 is millivolt times seconds times 5,000; however, other units can be used without departing from the scope and spirit of the exemplary embodiment.

Referring to FIG. 21, a cumulative distribution representation 2100 for each actual acoustic event is presented. According to this figure, the cumulative distribution representation 2100 includes a load axis 2110 and an acoustic emissions area axis 2130. The load axis 2110 is represented by an x-axis and is provided with units in the kilonewtons. The acoustic emissions area axis 2130 is represented by a y-axis and is provided with units in the millivolts times seconds times fifty thousand. This is the area that is determined that lies under an actual acoustic event point. Thus, to obtain the area in millivolts times seconds, the numerical value in the acoustic emissions area axis 2130 is to be divided by fifty thousand. Referring to FIGS. 16 and 21 and according to step 1645 of FIG. 16, the cumulative distribution of the areas, which is plotted along the acoustic emissions area axis 2130, is compared to the actual test load, which is plotted along the load axis 2110, for each actual acoustic event. The cumulative distribution representation 2100 provides these comparisons for a cutter manufacturer #1 cutter sample #1 cutter plot 2150 and a cutter manufacturer #2 cutter sample #2 cutter plot 2160.

For example, in one of the three cutter manufacturer #1 cutter sample #1 cutter plots 2150, there is an actual acoustic event point at about twenty-eight kilonewtons and at about 3550 millivolt times seconds times 50,000, which is labeled as a Point A 2152. This means that there has been a cumulative area of 3550 millivolt times seconds times 50,000 which has occurred under all previous actual acoustic event points, including the area for the actual acoustic event point that occurred at about a load of about twenty-eight kilonewtons. The next actual acoustic event point, Point B 2154, on that same curve occurs at about 32.5 kilonewtons. The area under that actual acoustic event point is about 650 millivolt times seconds times 50,000, which is not directly shown on the cumulative distribution representation 2100. However, at about 32.5 kilonewtons, there has been a cumulative area of about 4200 millivolt times seconds times 50,000. Thus, about 4200 millivolt times seconds times 50,000 minus about 3550 millivolt times seconds times 50,000 is equal to about 650 millivolt times seconds times 50,000. The harder cutter, or the one that is more intrinsically tougher, provides a curve that has a less cumulative area for a given load. A cutter with a steep curve with a lot of high amplitude actual acoustic event points is less intrinsically tougher than a cutter with a less steep curve and fewer high amplitudes actual acoustic event points. Thus, according to the cumulative distribution representation 2100, a comparison between the cutter manufacturer #1 cutter sample #1 cutter plot 2150 and the cutter manufacturer #2 cutter sample #2 cutter plot 2160 indicates that the cutter manufacturer #1 cutter sample #1 cutter is intrinsically tougher than the cutter manufacturer #2 cutter sample #2 cutter. Also, according to FIG. 21, there are three curves that represent the cutter manufacturer #1 cutter sample #1 cutter plot 2150 and two curves that represent the cutter manufacturer #2 cutter sample #2 cutter plot 2160. These plots 2150 and 2160 illustrate that method 1600 (FIG. 16) has a high resolution so that variabilities within samples of the same group are detectable. The method provided in FIG. 16 provides information to a user for ranking cutter toughnesses amongst other cutters in an objective manner.

Figure 17:
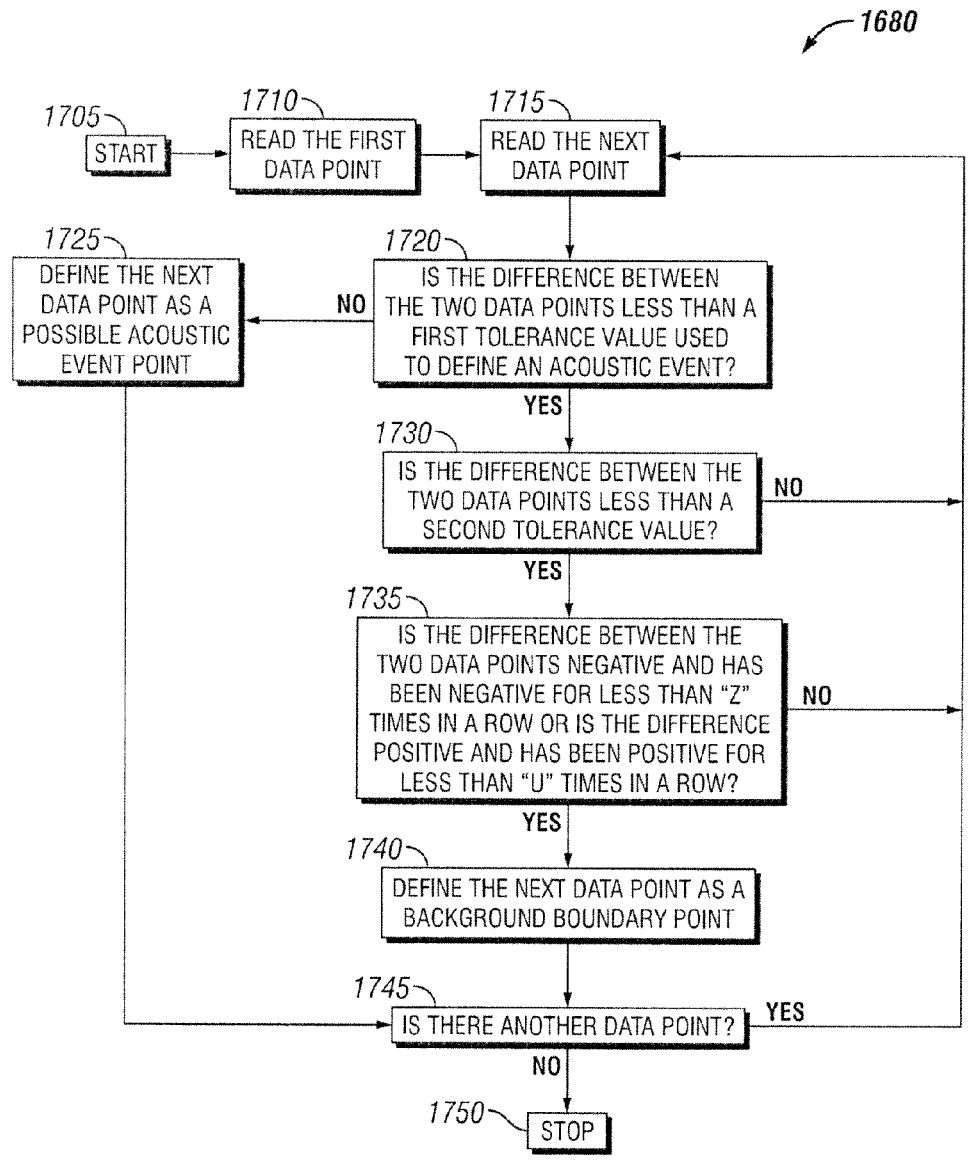
FIG. 17 illustrates a detailed flowchart of the loop one method of FIG. 16 in accordance with an exemplary embodiment of the present invention.

FIG. 17 illustrates a detailed flowchart of the loop one method 1680 of FIG. 16 in accordance with an exemplary embodiment of the present invention. Referring to FIG. 17, at step 1705, the loop one method 1680 starts. From step 1705, loop one method 1680 proceeds to step 1710. At step 1710, the first data point is read. Upon completion of step 1710, loop one method 1680 proceeds to step 1715, where the next data point is read. After step 1715, loop one method 1680 proceeds to step 1720. At step 1720, the difference between the two data points is calculated and compared to a first tolerance value that is used to define an acoustic event. According to one exemplary embodiment, the first tolerance value is about 0.5 millivolts. However, the first tolerance value can be higher or lower in other exemplary embodiments. If the difference between the two data points is not less than the first tolerance value, loop one method 1680 proceeds to step 1725. At step 1725, the second of the two data points is defined as a possible acoustic event point. From step 1725, loop one method 1680 proceeds to step 1745, where loop one method 1680 determines whether there is another data point. If at step 1745, it is determined that there is not another data point, loop one method 1680 proceeds to step 1750, where the loop one method 1680 stops. However, if at step 1745, it is determined that there is another data point, the loop one method 1680 proceeds back to step 1715.

If at step 1720, it is determined that the difference between the two data points is less than the first tolerance value, the loop one method 1680 proceeds to step 1730. At step 1730, the difference between the two data points is compared to a second tolerance value. According to one exemplary embodiment, the second tolerance value is about 0.01 millivolts. However, the second tolerance value can be higher or lower in other exemplary embodiments. If the difference between the two data points is not less than the second tolerance value, loop one method 1680 proceeds back to step 1715 and the second data point is not defined. However, if the difference between the two data points is less than the second tolerance value, loop one method 1680 proceeds to step 1735.

At step 1735, it is determined whether the difference between the two data points is negative and has been negative for less than "z" times in a row or whether the difference is positive and has been positive for less than "u" times in a row. According to one exemplary embodiment, the "z" is two and the "u" is three. However, either or both the "u" value and the "z" value can be higher or lower in other exemplary embodiments. If it is not true that the difference between the two data points is negative and has been negative for less than "z" times in a row or is positive and has been positive for less than "u" times in a row, then the loop one method 1680 proceeds back to step 1715 and the second data point is not defined. However, if the difference between the two data points is negative and has been negative for less than "z" times in a row or is positive and has been positive for less than "u" times in a row, then the loop one method 1680 proceeds to step 1740.

At step 1740, the second of the two data points is defined as a background boundary point. From step 1740, the loop one method 1680 proceeds to step 1745, where it is determined whether there is another data point. The loop one method 1680 continues until step 1750 is reached pursuant to the steps described above. Thus, the loop one method 1680 provides a method for determining which data points should be defined as a possible acoustic event point, a background boundary point, or not defined as either type of point.

Figure 18:
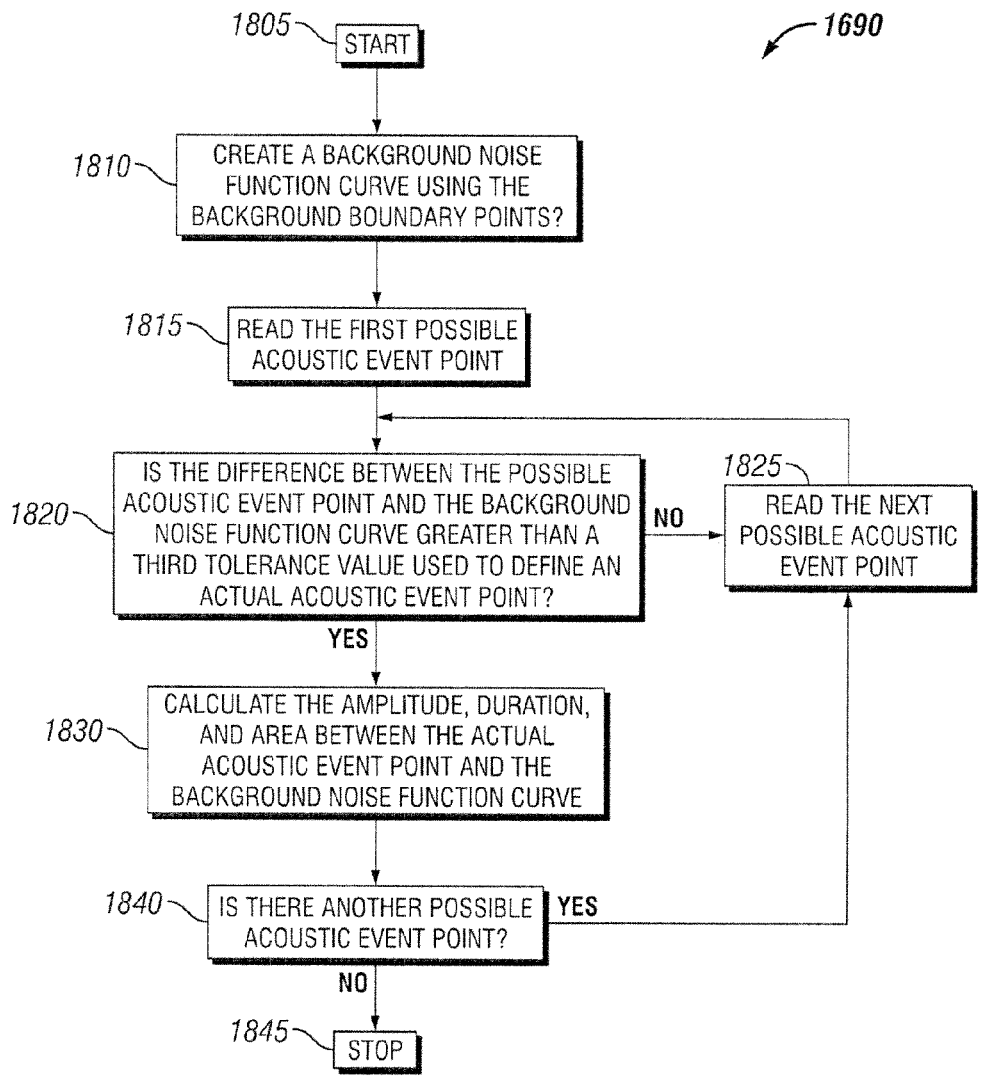
FIG. 18 illustrates a detailed flowchart of the loop two method of FIG. 16 in accordance with an exemplary embodiment of the present invention.

FIG. 18 illustrates a detailed flowchart of the loop two method 1690 of FIG. 16 in accordance with an exemplary embodiment of the present invention. Referring to FIG. 18, at step 1805, the loop two method 1690 starts. From step 1805, loop two method 1690 proceeds to step 1810. At step 1810, a background noise function curve is created using the background boundary points. Upon completion of step 1810, loop two method 1690 proceeds to step 1815, where the first possible acoustic event point is read. After step 1815, loop two method 1690 proceeds to step 1820. At step 1820, the difference between the possible acoustic event point and the background noise function curve is calculated and determined whether this difference is greater than a third tolerance value that is used to define an actual acoustic event point. According to one exemplary embodiment, the third tolerance value is about 0.08 millivolts. However, the third tolerance value can be higher or lower in other exemplary embodiments. If the difference between the possible acoustic event point and the background noise function curve is not greater than the third tolerance value, loop two method 1690 proceeds to step 1825. At step 1825, the next possible acoustic event point is read and the loop two method 1690 proceeds back to step 1820. However, if the difference between the possible acoustic event point and the background noise function curve is greater than the third tolerance value, loop two method 1690 proceeds to step 1830.

At step 1830, the amplitude, the duration, and the area between the actual acoustic event point and the background noise function curve are calculated From step 1830, the loop two method 1690 proceeds to step 1840. At step 1840, it is determined whether there is another possible acoustic event point. If there is another possible acoustic event point, the loop two method 1690 proceeds back to step 1825, where the loop two method 1690 continues. However, at step 1840, if there is not another possible acoustic event point, the loop two method 1690 proceeds to step 1845, where the loop two method 1690 stops. Thus, the loop two method 1690 provides a method for determining which data points should be defined as an actual acoustic event point and then calculates the area for each defined acoustic event point.

Figure 22:
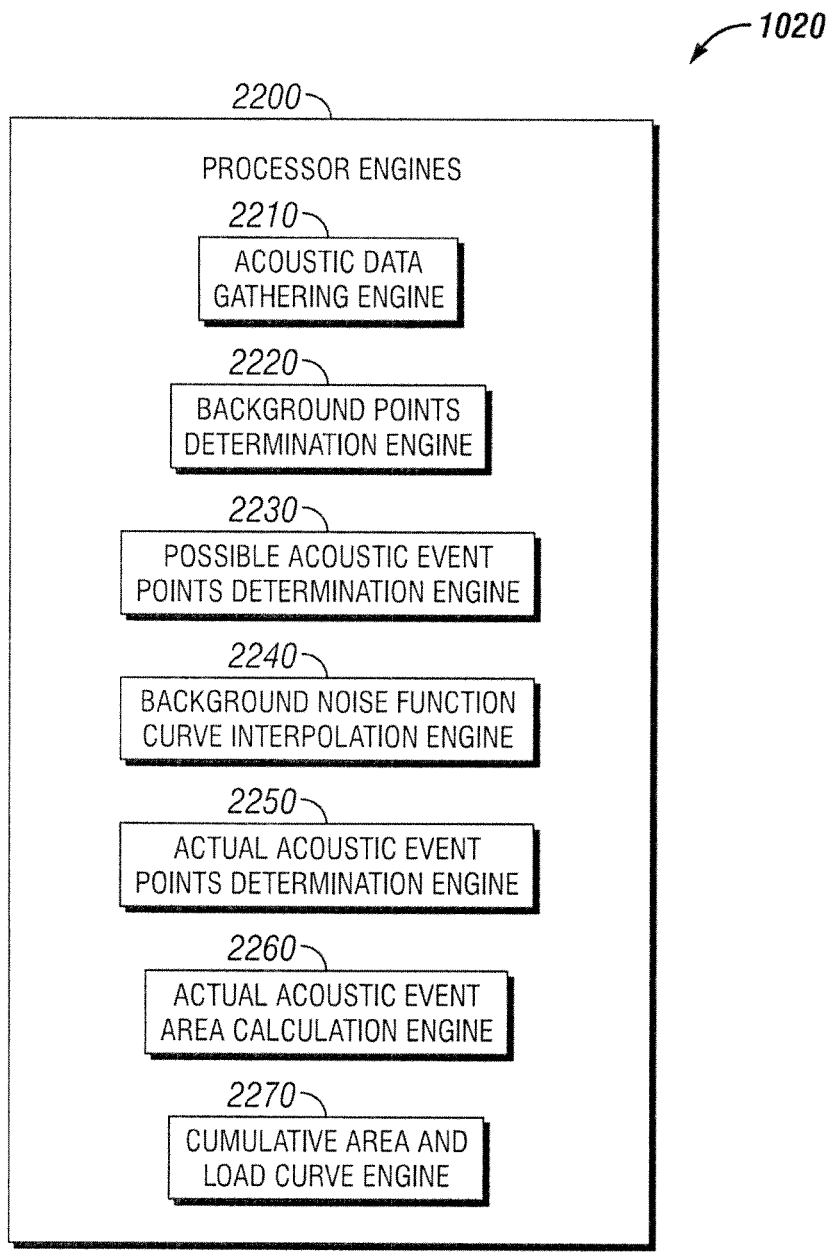
FIG. 22 shows a block diagram of the processor of FIG. 10 in accordance with an exemplary embodiment.

FIG. 22 illustrates a block diagram of the processor 1020 of FIG. 10 in accordance with an exemplary embodiment. As previously mentioned, the method for performing one or more steps illustrated in FIGS. 16-18 is performed within the processor 1020. However, in certain other exemplary embodiments, these methods are performed manually or a combination of manually and within a processor. The processor 1020 is located within the data recorder 590, or a computer system. Although one processor 1020 is shown, multiple processors can be used without departing from the scope and spirit of the exemplary embodiments. Processor 1020 includes one or more processor engines 2200.

The processor engines 2200 include an acoustic data gathering engine 2210, a background points determination engine 2220, a possible acoustic event points determination engine 2230, a background noise function curve interpolation engine 2240, an actual acoustic event points determination engine 2250, an actual acoustic event area calculation engine 2260, and a cumulative area and load curve engine 2270. Although seven engines are included within the processor engines 2200, the number of engines can be greater or fewer in other exemplary embodiments. Additionally, one or more of these previously mentioned processor engines 2200 can be combined into fewer processor engines 2200 or separated into additional processor engines 2200 without departing from the scope and spirit of the exemplary embodiments.

The acoustic data gathering engine 2210 gathers data from at least the acoustic sensor, which includes background points and possible acoustic event points. The acoustic data gathering engine 2210 also gathers data from the load, in some exemplary embodiments, so that corresponding background points and possible acoustic event points are related to a given load. The background points determination engine 2220 evaluates the data obtained from the acoustic sensor and determines whether the data point is a background point. The background points determination engine 2220 performs step 1615 of FIG. 16. The possible acoustic event points determination engine 2230 evaluates the data obtained from the acoustic sensor and determines whether the data point is a possible acoustic event point. The possible acoustic event points determination engine 2230 performs step 1625 of FIG. 16. The background points determination engine 2220 and the possible acoustic event points determination engine 2230 run simultaneously with one another, but can run independently from one another in some alternative exemplary embodiments.

The background noise function curve interpolation engine 2240 generates a background noise function curve using the background points that were previously determined. The background noise function curve interpolation engine 2240 performs step 1620 of FIG. 16. The actual acoustic event points determination engine 2250 determines actual acoustic event points using the possible acoustic event points that were previously determined and the background noise function curve. The actual acoustic event points determination engine 2250 performs step 1630 of FIG. 16. Once the actual acoustic event points are determined, the actual acoustic event area calculation engine 2260 determines the area formed between the actual acoustic event point and the background noise function curve. The actual acoustic event area calculation engine 2260 performs step 1635 and step 1640 of FIG. 16. The cumulative area and load curve engine 2270 compares the cumulative distribution of the areas to the actual test load for each actual acoustic event point. The cumulative area and load curve engine 2270 performs step 1645 of FIG. 16. Although the processor engines 2200 are located in the processor 1020 in some exemplary embodiments, the processor engines 2200 can reside in a storage medium including, but not limited to, one or more hard drives, a USB drive, a compact disc, a digital video disc, or any other storage device known or not yet known to people having ordinary skill in the art.

Although processor engines 2200 are described in the exemplary embodiments, the instructions for determining the toughness of the cutter can be provided in a software that resides within the storage medium 1040 (FIG. 10). The software includes modules and/or code that are similar to the processor engines 2200 described above.

Figure 23:
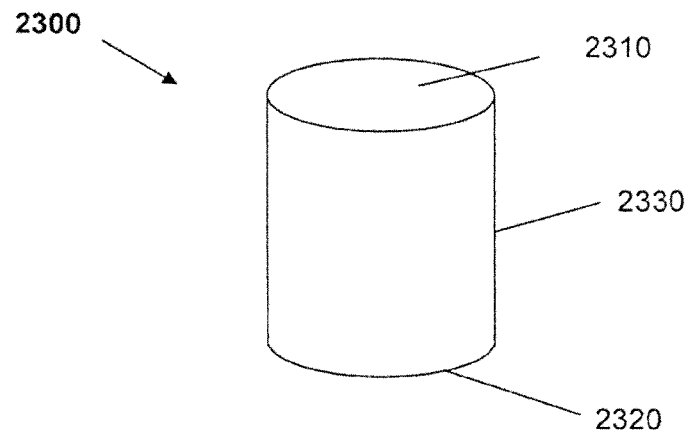
FIG. 23 shows a rock sample that is testable within the acoustic emission testing systems of FIGS. 5 and 9, respectively, in lieu of the cutter of FIG. 1 in accordance with an exemplary embodiment.

FIG. 23 shows a rock sample 2300 that is testable within the acoustic emission testing systems 500 and 900 of FIGS. 5 and 9, respectively, in lieu of the cutter 100 of FIG. 1 in accordance with an exemplary embodiment. Referring to FIGS. 5, 6, 9, and 23, the rock sample 2300 replaces the cutter 100 in the acoustic emission testing system 500 or the acoustic emission testing system 900. The testing method and analysis of the results are similar to those methods and analysis described above and provides information relating to the unconfined compressive strength and/or toughness of the rock sample 2300.

The rock sample 2300 is cylindrically shaped, which is similar to the cutter 100. The rock sample includes a first planar surface 2310 at one end of the rock sample 2300, a second planar surface 2320 at an opposing end of the rock sample, and a circumferential surface 2330 extending from the first surface 2310 to the second surface 2320. However, in alternative exemplary embodiments, the rock sample 2300 is shaped in other geometric or non-geometric shapes, such as cube-shaped. In certain exemplary embodiments, the shape of the rock sample 2300 is a repeatable shape such that multiple rock samples 2300 are formed with a substantially similar shape; thereby allowing the test results to be comparable.

Figure 24:
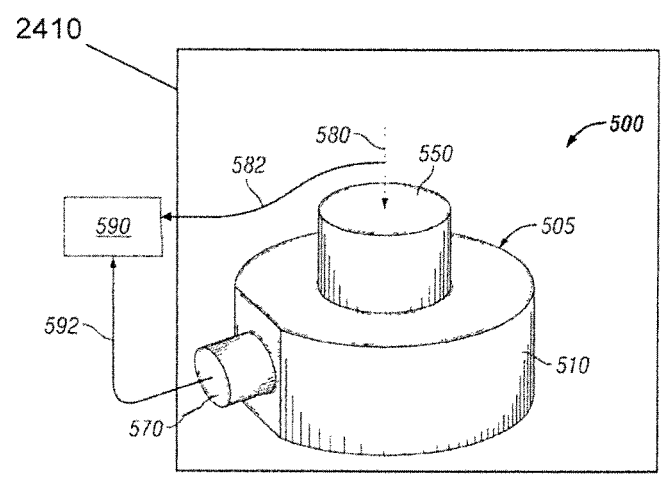
FIG. 24 shows the acoustic emission testing device of FIG. 5 inserted within a pressurizable chamber in accordance with an exemplary embodiment.

FIG. 24 shows the acoustic emission testing device 505 of FIG. 5 inserted within a pressurizable chamber 2410 in accordance with an exemplary embodiment. The pressure within the pressurizable chamber 2410 is variable in a controllable and measurable manner. The pressure within the pressurizable chamber 2410 is variable from zero psi to about 40000 psi in some exemplary embodiments; however, the range of pressures can be higher or lower in other exemplary embodiments. In this exemplary embodiments, other components, including the sensor 570 and the indenter 550, are capable of withstanding the pressures formed within the pressurizable chamber 2410. According to these exemplary embodiments, the rock confined compressive strength and toughness are measurable at different levels of hydrostatic pressures, thereby providing vital information of the rock properties at different depths below the earth surface. The information collected is usable to improve the knowledge of rock failing mechanisms and also lead to new theories and rock solid mechanic models. The information collected also is usable to confirm other known theories not yet proven. Although the pressurizable chamber 2410 is one method for testing the hard or superhard material 100, such as the rock sample 2300, under pressure, other mechanisms for providing pressures on the hard or superhard material 100 can be used, such as using high strength binding rings assembled together and around the hard or superhard material 100, in alternative exemplary embodiments.

The knowledge of the UCS and the toughness of the rock samples 2300 are usable by designers to create new and innovative bit designs having superior performance and/or to develop a new bit design procedure which incorporates the UCS value and the $K_{1C}$ value. The information obtained from the rock samples 2300 is usable to calibrate geoscience and/or geomechanics software and tools.

Although some exemplary embodiments of the invention have been described, alternative exemplary embodiments include the use of heating the hard or superhard material 100. This heating of the hard or superhard material 100 occurs at either or a combination of before, during, and/or after the application of the load onto the hard or superhard material 100. The heat is supplied in any one of a number of ways known to people having ordinary skill in the art, which include, but is not limited to, flame, laser, infrared, and/or heated liquid.

Figure 25:
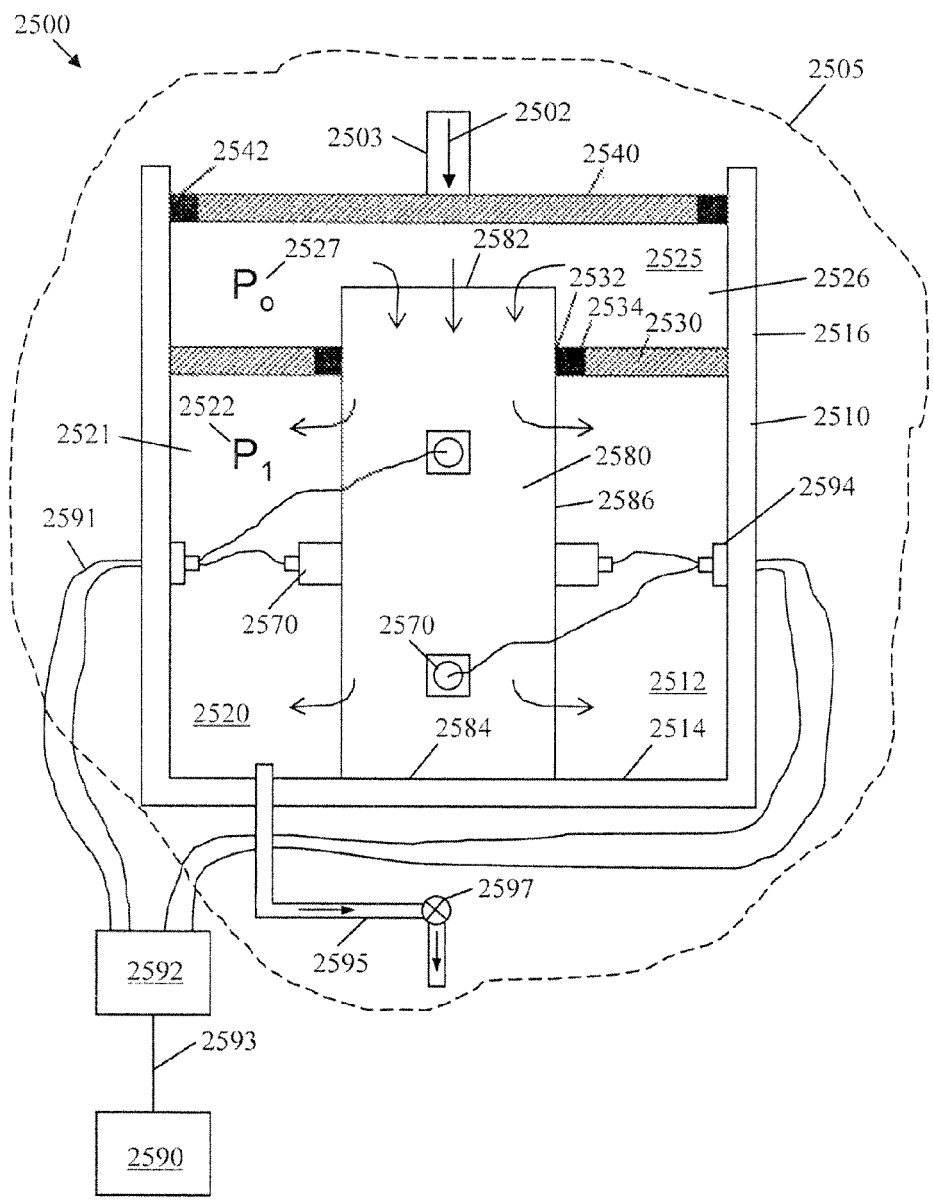
FIG. 25 shows a cross-sectional view of an acoustic emission testing system in accordance with an exemplary embodiment of the present invention.

FIG. 25 shows a cross-sectional view of an acoustic emission testing system 2500 in accordance with an exemplary embodiment of the present invention. Referring to FIG. 25, the acoustic emission testing system 2500 includes an acoustic emission testing device 2505 communicably coupled to an analog-to-digital converter 2592, which is communicably coupled to a data recorder 2590. According to some exemplary embodiments, the analog-to-digital converter 2592 is optional. The acoustic emission testing device 2505 includes a pressurizable chamber 2510, a rock sample 2580, one or more acoustic sensors 2570, a first barrier 2530, a second barrier 2540, and a drain pipe 2595. In some exemplary embodiments, the acoustic emission testing device 2505 also includes one or more couplings 2594 and a drain pipe pressure control valve 2597. Although the rock sample 2580 is depicted in the exemplary embodiment, other types of porous samples can be used in lieu of the rock sample 2580 according to other alternative exemplary embodiments.

The pressurizable chamber 2510 is cylindrically shaped and forms a cavity 2512 therein. However, according to other exemplary embodiments, the pressurizable chamber 2510 is shaped in some other geometric shape, such as a cube-shape, or non-geometric shape. The pressure within the pressurizable chamber 2510 is variable in a controllable and measurable manner. The pressure within the pressurizable chamber 2510 is variable from zero psi to about 40000 psi in some exemplary embodiments; however, the range of pressures can be higher or lower in other exemplary embodiments. The pressurizable chamber 2510 includes a base 2514 and a sidewall 2516 extending substantially perpendicular around the perimeter of the base 2514. In some alternative exemplary embodiments, the sidewall 2516 extends substantially perpendicular from the base 2514 at a position that is within the perimeter of the base 2514. The pressurizable chamber 2510 is fabricated from steel; however, according to other exemplary embodiments, the pressurizable chamber 2510 is fabricated from any metal, metal alloy, polymer, wood, or other suitable material known to people having ordinary skill in the art that is capable of withstanding at least a second pressure ($P_O$) 2527, which is described in further detail below. In certain exemplary embodiments, the suitable material is capable of being machined or molded and is capable of propagating sound. In certain exemplary embodiments, the suitable material is capable of propagating sound at a speed of about 1 kilometers per second or higher.

The cavity 2512 is formed within the pressurizable chamber 2510 and is sized to receive the entire rock sample 2580, or some other hard or superhard material. The cavity 2512 is sized larger in diameter than the diameter of the rock sample 2580, thereby allowing the rock sample 2580 to easily and freely fit within the cavity 2512. The cavity 2512 is circular in shape, but is any other geometric or non-geometric shape in other exemplary embodiments. The cavity 2512 is formed by machining the pressurizable chamber 2510 or molding the pressurizable chamber 2510 to have the cavity 2512 formed therein. Alternatively, the cavity 2512 is formed using other methods known to people having ordinary skill in the art. In certain exemplary embodiments, the cavity 2512 is formed in a manner to ensure that the rock sample 2580 is properly aligned in the same manner each time the rock sample 2580 is inserted within the cavity 2512. For example, the base 2514 can be keyed to receive the rock sample 2580 in a desired position. For example, the base 2514 includes one or more protrusions (not shown) and/or one or more indentations (not shown) in certain exemplary embodiments.

The rock sample 2580 is a porous material. According to some exemplary embodiments, the rock sample 2580 is formed from a sample of rock obtained from within a drill hole, or wellbore, located at some depth within the wellbore and at a confining pressure. Some examples of rock samples 2580 include, but are not limited to, coal, chalk, shale, limestone, sandstone, all geological formations that include gas or oil, and other known porous rocks. The rock sample 2580 is substantially cylindrical in shape, but can be shaped into other geometric shapes, such as substantially cube-shaped, or non-geometric shapes. The rock sample 2580 includes a top surface 2582, a bottom surface 2584, and a sidewall 2586 extending from the top surface 2582 to the bottom surface 2584. The top surface 2582 and the bottom surface 2584 are substantially parallel to one another; however, according to other exemplary embodiments, the top surface 2582 and the bottom surface 2584 are not parallel to one another. The sidewall 2586 extends substantially perpendicular to both the top surface 2582 and the bottom surface 2584; however, in certain exemplary embodiments, the sidewall 2586 is not perpendicular to at least one of the top surface 2582 and the bottom surface 2584. According to some exemplary embodiments, the sidewall 2586 is arcuate; however, according to some other exemplary embodiments, at least some portions of the sidewall 2586 includes one or more planar surfaces (not shown). In these exemplary embodiments, these planar surfaces facilitate acoustic sensors 2570 being coupled to the rock sample 2580. The rock sample 2580 is inserted within the cavity 2512 so that the bottom surface 2584 is adjacent to the base 2514. According to some exemplary embodiments, the rock sample 2580 is positioned substantially in the center of the cavity 2512; however, the rock sample 2580 can be positioned off-center of the cavity 2512 in other exemplary embodiments.

The acoustic sensor 2570 is a piezoelectric sensor that is positioned along the sidewall 2586 of the rock sample 2580. However, the acoustic sensor 2570 can be any other device type known to people having ordinary skill in the art, wherein the device is capable of detecting acoustic transmissions. Additionally, according to some exemplary embodiments, the acoustic sensor 2570 is positioned along the exterior portion of the sidewall 2516 of the pressurizable chamber 2510. According to some exemplary embodiments, the acoustic sensor 2570 is sized so that it is capable of being placed on the arcuate portion of the sidewall 2586, 2516. In other exemplary embodiments, the acoustic sensor 2570 is placed on a planar portion (not shown) of the sidewall 2586, 2516. The acoustic sensor 2570 detects elastic wave signals formed in the rock sample 2580, which then converts the elastic waves signal to a voltage signal so that the data can be recorded and subsequently analyzed.

The acoustic sensor 2570 is communicably coupled to the data recorder 2590, via the analog-to-digital converter 2592 in certain exemplary embodiments, so that the voltage signal derived from the elastic waves occurring within the rock sample 2580 can be stored and subsequently analyzed. The data recorder 2590 is similar to the data recorder 590 (FIG. 5) and will not be discussed in detail again. The data recorder 2590 also is set-up similarly to the set-up of data recorder 590 (FIG. 5). In some exemplary embodiments, the acoustic sensor 2570 is coupled to the analog-to-digital converter 2592 using a first cable 2591; however, according to other exemplary embodiments, the acoustic sensor 2570 can be communicably coupled to the analog-to-digital converter 2592 wirelessly using wireless technology including, but not limited to, infrared and radio frequency. In the example where the acoustic sensor 2570 is placed on the rock sample 2580, the first cable 2591 is routed from within the pressurizable chamber 2510 to an area outside the pressurizable chamber 2510 through the coupling 2594 which provides a communication pathway between the interior of the pressurizable chamber 2510 to the exterior of the pressurizable chamber 2510. Each coupling 2594 is able to accommodate communication from one or several acoustic sensors 2570. The analog-to-digital converter 2592 converts the voltage signal, which is in analog format, to a digital format and sends the digital signal to the data recorder 2590. The analog-to-digital converter 2592 is communicably coupled to the data recorder 2590 using a second cable 2593; however, according to other exemplary embodiments, the analog-to-digital converter 2592 can be communicably coupled to the data recorder 2590 wirelessly using wireless technology including, but not limited to, infrared and radio frequency. According to some exemplary embodiments, the analog-to-digital converter 2592 is incorporated into the data recorder 2590 as a single component and thus the acoustic sensor 2570 transmits signals directly to the data recorder 2590.

According to the exemplary embodiment illustrated in FIG. 25, there are four acoustic sensors 2570 coupled to the rock sample 2580. However, the number of acoustic sensors 2570 ranges from one acoustic sensor 2570 to any number of acoustic sensors 2570. The acoustic sensors 2570 are able to detect the intensity of acoustic events occurring on or within the rock sample 2580 with respect to time and space. Thus, the location of the acoustic events and the direction in which the cracks are propagating within the rock sample 2580 are determinable. According to some examples, at least one or more acoustic sensors 2570 are positioned at different elevational heights along the sidewall 2586. In one example, three acoustic sensors 2570 are coupled to the rock sample 2580 at different elevational heights along the sidewall 2586. A first acoustic sensor 2570 detects the intensity of the acoustic event occurring within the rock sample 2580 at a first time period and determines the location of the acoustic event occurring within the rock sample 2580 along a first axis, or x-axis. A second acoustic sensor 2570 detects the intensity of the acoustic event occurring within the rock sample 2580 at the first time period and determines the location of the acoustic event occurring within the rock sample 2580 along a second axis, or y-axis. A third acoustic sensor 2570 detects the intensity of the acoustic event occurring within the rock sample 2580 at the first time period and determines the location of the acoustic event occurring within the rock sample 2580 along a third axis, or z-axis. The acoustic sensors 2570 perform the same analysis at a second time period, a third time period, and so forth. Using the speed of sound known within the rock sample 2580, data from the three acoustic sensors 2570 provide information for determining the intensity of the acoustic event occurring within the rock sample 2580, the location of the acoustic event occurring within the rock sample 2580, and the direction in which the acoustic event is propagating within the rock sample 2580. In the embodiments where the acoustic sensors 2570 are positioned along the pressurizable chamber's sidewall 2516, the speed of sound through a first fluid 2521 and the distance between the respective acoustic sensor 2570 and the rock sample's sidewall 2586 also are used in the determinations. If fewer acoustic sensors 2570 are used, one or more axes are lost for determining where the acoustic event is occurring within the rock sample 2580 along those axes. Each acoustic sensor 2570 represents an axis. When greater than three acoustic sensors 2570 are used, the measurements provide more precise determinations for locating the acoustic events occurring within the rock sample 2580. The data from the three acoustic sensors 2570 are used to triangulate the location of the acoustic event.

The first barrier 2530 is substantially disc-shaped and includes an opening 2532 extending therethough. The opening 2532 is substantially positioned centrally within the first barrier 2530 and is sized for inserting at least the top surface 2582 within the opening 2532. In some exemplary embodiments, the opening 2532 is used to properly position the rock sample 2580 in the pressurizable chamber 2510. In some exemplary embodiments, the top surface 2582 and at least a portion of the rock sample's sidewall 2586 is inserted through the opening 2532. The opening 2532 is shaped similarly to the shape of at least a portion of a cross-sectional portion of the rock sample's sidewall 2586. Although the first barrier 2530 is substantially disc-shaped, the shape can be any other geometric shape or non-geometric shape that is substantially similar to at least a portion of the cross-sectional shape of the cavity 2512. The first barrier 2530 is fixedly coupled to the interior portion of the sidewall 2516 of the pressurizable chamber 2510, thereby dividing the cavity 2512 into a first chamber 2520 and a second chamber 2525. The first barrier 2530 is coupled to the sidewall 2516 using welding or any other methods known to people having ordinary skill in the art. The weld or any other device used for attaching the first barrier 2530 to the pressurizable chamber's sidewall 2516 is capable of withstanding pressures of at least the second pressure 2527. The first barrier 2530 is fabricated using a metal, metal alloy, polymer, or any other suitable material capable of withstanding pressures of up to at least the second pressure 2527. A first seal 2534 is positioned about the perimeter of the opening 2532 and provides a pressure seal with the rock sample's sidewall 2586. The first seal 2534 is a rubber gasket or any other suitable material known to people having ordinary skill in the art. The pressure within the first chamber 2520 is a first pressure ($P_1$) 2522 which can be different than the second pressure 2527 within the second chamber 2525 during testing, which is described in further detail below. Each of the first pressure 2522 and the second pressure 2527 is variable. Thus, a portion of the rock sample 2580 is exposed to the first pressure 2522 while another portion of the rock sample 2580 is exposed to the second pressure 2527 during testing.

Within the first chamber 2520, the first fluid 2521 is placed. The first fluid 2521 fills up the entire first chamber 2520 in some exemplary embodiments; however, in other exemplary embodiments, the first fluid 2521 fills a portion of the first chamber 2520. The first fluid 2521 is water. However, other types of fluid having similar properties can be used as the first fluid 2521 in other exemplary embodiments. In some exemplary embodiments, the first fluid 2521 includes sand particles or other similar particle types.

The second barrier 2540 also is substantially disc-shaped and includes a second seal 2542 around the perimeter of the second barrier 2540. Although the second barrier 2540 is substantially disc-shaped, the shape can be any other geometric shape or non-geometric shape that is substantially similar to at least a portion of the cross-sectional shape of the cavity 2512. The second barrier 2540 is positioned near the top portion of the pressurizable chamber 2510 within the cavity 2512 and is movably coupled to the interior portion of the sidewall 2516 of the pressurizable chamber 2510. The second barrier 2540 forms a portion of the second chamber 2525. The second seal 2542 provides a pressure seal between the second barrier 2540 and the pressurizable chamber's sidewall 2516. The second seal 2542 is a rubber gasket or any other suitable material known to people having ordinary skill in the art. The second barrier 2540 thereby provides a means for varying the second pressure 2527 within the second chamber 2525. An external force 2502 is applied on the second barrier 2540 which moves the second barrier 2540 closer to the first barrier 2530. As the second barrier 2540 moves closer to the first barrier 2520, the second pressure 2527 increases, and as the second barrier 2540 moves further away from the first barrier 2520, the second pressure 2527 decreases. The external pressure 2502 is provided by a piston 2503 in some exemplary embodiments; however, the external force 2502 can be provided by any other known methods and/or devices. The second barrier 2540 is fabricated using a metal, metal alloy, polymer, or any other suitable material capable of withstanding pressures of up to at least the second pressure 2527 and/or the external force 2502, whichever is greater.

Within the second chamber 2525, a second fluid 2526 is placed. The second fluid 2526 fills up the entire second chamber 2525 in some exemplary embodiments; however, in other exemplary embodiments, the second fluid 2526 fills a portion of the second chamber 2525. The second fluid 2526 is water. However, other types of fluid having similar properties can be used as the second fluid 2526 in other exemplary embodiments. In some exemplary embodiments, the second fluid 2526 includes sand particles or other similar particle types. According to some exemplary embodiments, the second fluid 2526 is the same as the first fluid 2521; however, the second fluid 2526 can be different than, but similar in properties to, the first fluid 2521 in other exemplary embodiments. As the second pressure 2527 in the second chamber 2525 increases above the first pressure 2522 in the first chamber 2520, the second fluid 2526 flows from the second chamber 2525 into the rock sample 2580 and out into the first chamber 2520. As the second pressure 2527 increases, acoustic events, or cracks, form in the rock sample 2580. In the exemplary embodiments where sand particles are included in the second fluid 2526, the sand particles can enter into the cracks formed within the rock sample 2580 and become lodged therein as to prevent the cracks from closing when the second pressure 2527 is decreased.

As the second pressure 2527 increases and the second fluid 2526 flows into the first chamber 2520 through the rock sample 2580, the first pressure 2522 increases. To maintain the first pressure 2522 constant or substantially constant, a drain pipe 2595 is coupled to the interior of the first chamber 2520 and through the base 2514 to allow the first fluid 2521 and/or the second fluid 2526 that is present within the first chamber 2520 to exit the first chamber 2520. The drain pipe 2595 is fabricated from a metal, metal alloy, polymer, or other suitable material capable of withstanding the first pressure 2522. In certain exemplary embodiments, the drain pipe pressure control valve 2597 is installed at a location along the drain pipe 2595 and is configured to be opened and closed, either automatically or manually, to maintain the first pressure 2522 at a substantially constant pressure during the testing process. In alternative exemplary embodiments, the drain pipe 2595 is coupled to the interior of the first chamber 2520 through the sidewall 2516.

The operation of the acoustic emission testing system 2500 is described while referring to FIGS. 25. Once the acoustic emission testing system 2500 is configured according to the description provided above, the drain pipe control valve 2597 is set to maintain the pressure in the first chamber 2520 at the first pressure 2522. The first pressure 2522 is determined to be the rock confining pressure, which is the pressure at which the rock sample 2580 was exposed to while in the wellbore. The external force 2502 exerted onto the second barrier 2540 is increased, thereby pushing the second barrier 2540 closer towards the first barrier 2530. This movement of the second barrier 2540 compresses the second fluid 2526, thereby increasing the second pressure 2527 within the second chamber 2525. The second pressure 2527 increases to a value above the first pressure 2522 and is ramped up so that acoustic events, or cracking, occurs on or within the rock sample 2580. The second pressure 2527 is continuously ramped up until the second pressure 2527 reaches a threshold pressure, which is where extensive acoustic events occur within the rock sample 2580. Once the second pressure 2527 increases above the first pressure 2522, the second fluid 2526 passes through the porous rock sample 2580 and enters into the first chamber 2520. The first pressure 2522 would typically increase due to the second fluid 2526 entering the first chamber 2520; however, the drain pipe control valve 2597 maintains the first pressure 2522 substantially constant and allows the first fluid 2521 and/or the second fluid 2526 that has entered into the first chamber 2520 to exit the first chamber 2520 through the pipe drain 2595. This threshold pressure that is reached is the pressure that is to be generated in the wellbore for fracing the rock at that confining pressure. During the testing procedure, the acoustic events are measured according to the descriptions provided above. Additionally, the location of the acoustic events are determinable by people having ordinary skill in the art having the benefit of the present disclosure. Moreover, the direction in which the acoustic events are propagating also are determinable by people having ordinary skill in the art having the benefit of the present disclosure. The acoustic sensors 2570 obtain data when the second pressure 2627 is increased. Additionally, in some exemplary embodiments, the acoustic sensors 2570 also obtain data when the second pressure 2627 is decreased after reaching the threshold pressure. Although not illustrated, the first pressure 2522 and the second pressure 2527 are monitored. According to some exemplary embodiments, the second pressure 2527 is recorded.

Figure 26:
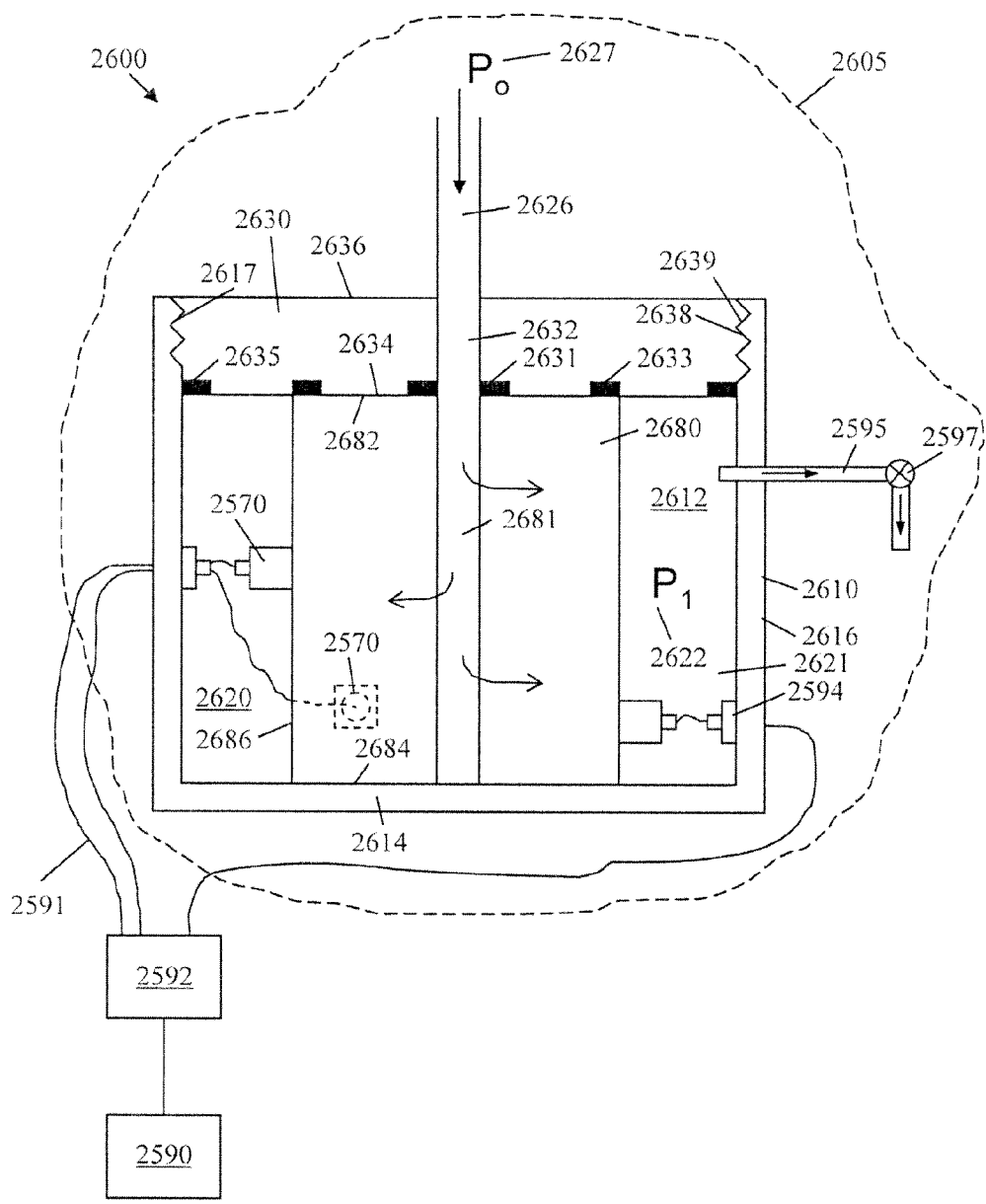
FIG. 26 shows a cross-sectional view of an acoustic emission testing system in accordance with another exemplary embodiment of the present invention.

FIG. 26 shows a cross-sectional view of an acoustic emission testing system 2600 in accordance with another exemplary embodiment of the present invention. Referring to FIG. 26, the acoustic emission testing system 2600 includes an acoustic emission testing device 2605 communicably coupled to an analog-to-digital converter 2592, which is communicably coupled to a data recorder 2590. According to some exemplary embodiments, the analog-to-digital converter 2592 is optional. The acoustic emission testing device 2605 includes a pressurizable chamber 2610, a rock sample 2680, one or more acoustic sensors 2570, a cover 2630, and the drain pipe 2595. In some exemplary embodiments, the acoustic emission testing device 2605 also includes one or more couplings 2594 and the drain pipe pressure control valve 2597. Although the rock sample 2680 is depicted in the exemplary embodiment, other types of porous samples can be used in lieu of the rock sample 2680 according to other alternative exemplary embodiments. Since the analog-to-digital converter 2592, the data recorder 2590, the acoustic sensors 2570, the drain pipe 2595, the couplings 2594, and the drain pipe pressure control valve 2597 have been previously described in detail with respect to FIG. 25, these components are not described in detail again with respect to FIG. 26.

The pressurizable chamber 2610 is cylindrically shaped and forms a cavity 2612 therein. However, according to other exemplary embodiments, the pressurizable chamber 2610 is shaped in some other geometric shape, such as a cube-shape, or non-geometric shape. The pressure within the pressurizable chamber 2610 is variable in a controllable and measurable manner. The pressure within the pressurizable chamber 2610 is variable from zero psi to about 40000 psi in some exemplary embodiments; however, the range of pressures can be higher or lower in other exemplary embodiments. The pressurizable chamber 2610 includes a base 2614 and a sidewall 2616 extending substantially perpendicular around the perimeter of the base 2614. In some alternative exemplary embodiments, the sidewall 2616 extends substantially perpendicular from the base 2614 at a position that is within the perimeter of the base 2614. According to some exemplary embodiments, the top portion of the sidewall 2616 includes threads 2617 for receiving and coupling with the cover 2630. However, in other exemplary embodiments, the cover 2630 is sealably coupled to the top portion of the sidewall 2616 using other methods known to people having ordinary skill in the art, such as using fasteners and using welds. The pressurizable chamber 2610 is fabricated from steel; however, according to other exemplary embodiments, the pressurizable chamber 2610 is fabricated from any metal, metal alloy, polymer, wood, or other suitable material known to people having ordinary skill in the art that is capable of withstanding at least a second pressure ($P_O$) 2627, which is described in further detail below. In certain exemplary embodiments, the suitable material is capable of being machined or molded and is capable of propagating sound. In certain exemplary embodiments, the suitable material is capable of propagating sound at a speed of about 1 kilometers per second or higher.

The cavity 2612 is formed within the pressurizable chamber 2610 and is sized to receive the entire rock sample 2680, or some other hard or superhard material. The cavity 2612 is sized larger in diameter than the diameter of the rock sample 2680, thereby allowing the rock sample 2680 to easily and freely fit within the cavity 2612. The cavity 2612 is circular in shape, but is any other geometric or non-geometric shape in other exemplary embodiments. The cavity 2612 is formed by machining the pressurizable chamber 2610 or molding the pressurizable chamber 2610 to have the cavity 2612 formed therein. Alternatively, the cavity 2612 is formed using other methods known to people having ordinary skill in the art. In certain exemplary embodiments, the cavity 2612 is formed in a manner to ensure that the rock sample 2680 is properly aligned in the same manner each time the rock sample 2680 is inserted within the cavity 2612. For example, the base 2614 can be keyed to receive the rock sample 2680 in a desired position. For example, the base 2614 includes one or more protrusions and/or one or more indentations in certain exemplary embodiments.

The rock sample 2680 is a porous material. According to some exemplary embodiments, the rock sample 2680 is formed from a sample of rock obtained from within a drill hole, or wellbore, located at some depth within the wellbore and at a confining pressure. Some examples of rock samples 2680 include, but are not limited to, coal, chalk, shale, limestone, sandstone, all geological formations that include gas or oil, and other known porous rocks. The rock sample 2680 is substantially cylindrical in shape, but can be shaped into other geometric shapes, such as substantially cube-shaped, or non-geometric shapes. The rock sample 2680 includes a top surface 2682, a bottom surface 2684, and a sidewall 2686 extending from the top surface 2682 to the bottom surface 2684. The top surface 2682 and the bottom surface 2684 are substantially parallel to one another; however, according to other exemplary embodiments, the top surface 2682 and the bottom surface 2684 are not parallel to one another. The sidewall 2686 extends substantially perpendicular to both the top surface 2682 and the bottom surface 2684; however, in certain exemplary embodiments, the sidewall 2686 is not perpendicular to at least one of the top surface 2682 and the bottom surface 2684. According to some exemplary embodiments, the sidewall 2686 is arcuate; however, according to some other exemplary embodiments, at least some portions of the sidewall 2686 includes one or more planar surfaces (not shown). In these exemplary embodiments, these planar surfaces facilitate acoustic sensors 2570 being coupled to the rock sample 2680.

The rock sample 2680 also includes an opening 2681 extending from the top surface 2682 to the bottom surface 2684. The opening 2681 is positioned centrally through the rock sample 2680; however, in other exemplary embodiments, the opening 2681 can be positioned off-centered through the rock sample 2680. In alternative exemplary embodiments, the opening 2681 extends toward the bottom surface 2684 but does not extend through the bottom surface 2684. The rock sample 2680 is inserted within the cavity 2612 so that the bottom surface 2684 is adjacent to the base 2614. According to some exemplary embodiments, the rock sample 2680 is positioned substantially in the center of the cavity 2612; however, the rock sample 2680 can be positioned off-center of the cavity 2612 in other exemplary embodiments.

The acoustic sensor 2570 has been previously described and will not be described in detail for the sake of brevity. One or more acoustic sensors are positioned along the sidewall 2686 of the rock sample 2680. According to some exemplary embodiments, the one or more acoustic sensors 2570 are positioned along the exterior portion of the sidewall 2616 of the pressurizable chamber 2610. The acoustic sensor 2570 detects elastic wave signals formed in the rock sample 2680, which then converts the elastic waves signal to a voltage signal so that the data can be recorded and subsequently analyzed.

The acoustic sensor 2570 is communicably coupled to the data recorder 2590, via the analog-to-digital converter 2592 in certain exemplary embodiments, so that the voltage signal derived from the elastic waves occurring within the rock sample 2680 can be stored and subsequently analyzed. The data recorder 2590 and the analog-to-digital converter 2592, along with their respective set-ups, have been previously described and will not be described in detail for the sake of brevity. In the example where the acoustic sensor 2570 is placed on the rock sample 2680, the first cable 2591 is routed from within the pressurizable chamber 2610 to an area outside the pressurizable chamber 2610 through the coupling 2594, which also has been previously described above and therefore will not be repeated for the sake of brevity.

According to the exemplary embodiment illustrated in FIG. 26, there are three acoustic sensors 2570 shown to be coupled to the rock sample 2680. However, the number of acoustic sensors 2570 ranges from one acoustic sensor 2570 to any number of acoustic sensors 2570. The acoustic sensors 2570 is able to detect the intensity of acoustic events occurring on or within the rock sample 2680 with respect to time and space. Thus, the location of the acoustic events and the direction in which the cracks are propagating within the rock sample 2680 are determinable. According to some examples, at least one or more acoustic sensors 2570 are positioned at different elevational heights along the sidewall 2686. In one example, three acoustic sensors 2570 are coupled to the rock sample 2680 at different elevational heights along the sidewall 2586. A first acoustic sensor 2570 detects the intensity of the acoustic event occurring within the rock sample 2680 at a first time period and determines the location of the acoustic event occurring within the rock sample 2680 along a first axis, or x-axis. A second acoustic sensor 2570 detects the intensity of the acoustic event occurring within the rock sample 2680 at the first time period and determines the location of the acoustic event occurring within the rock sample 2680 along a second axis, or y-axis. A third acoustic sensor 2570 detects the intensity of the acoustic event occurring within the rock sample 2680 at the first time period and determines the location of the acoustic event occurring within the rock sample 2680 along a third axis, or z-axis. The acoustic sensors 2570 perform the same analysis at a second time period, a third time period, and so forth. Using the speed of sound known within the rock sample 2680, data from the three acoustic sensors 2570 provide information for determining the intensity of the acoustic event occurring within the rock sample 2680, the location of the acoustic event occurring within the rock sample 2680, and the direction in which the acoustic event is propagating within the rock sample 2680. In the embodiments where the acoustic sensors 2570 are positioned along the pressurizable chamber's sidewall 2616, the speed of sound through a first fluid 2621 and the distance between the respective acoustic sensor 2570 and the rock sample's sidewall 2686 also are used in the determinations. If fewer acoustic sensors 2570 are used, one or more axes are lost for determining where the acoustic event is occurring within the rock sample 2680 along those axes. Each acoustic sensor 2570 represents an axis. When greater than three acoustic sensors 2570 are used, the measurements provide more precise determinations for locating the acoustic events occurring within the rock sample 2680. The data from the three acoustic sensors 2570 are used to triangulate the location of the acoustic events.

The cover 2630 is substantially disc-shaped and includes a bottom surface 2634, a top surface 2636, and a sidewall 2638 extending from the perimeter of the base 2634 to the top surface 2636. According to some exemplary embodiments, the sidewall 2638 is planar, while in other exemplary embodiments, the sidewall 2638 is non-planar. The bottom surface 2634 is configured to be inserted within the top portion of the pressurizable chamber's sidewall 2616 and form a seal therewith. The top surface 2636 is dimensioned the same as the bottom surface 2634 according to some exemplary embodiments, while in other exemplary embodiments, the top surface 2636 is dimensioned larger or smaller than the bottom surface 2634. According to some exemplary embodiments, at least the bottom portion of the sidewall 2638 includes mating threads 2639 for mating with the threads 2617. In other exemplary embodiments, the entire sidewall 2638 includes mating threads 2639. Although mating threads 2639 are used in some exemplary embodiments to sealably couple the top portion of the sidewall 2616 to the cover 2630, other methods known to people having ordinary skill in the art can be used, such as using fasteners and using welds. The cover 2630 is fabricated from steel; however, according to other exemplary embodiments, the cover 2630 is fabricated from any metal, metal alloy, polymer, wood, or other suitable material known to people having ordinary skill in the art that is capable of withstanding at least the second pressure ($P_O$) 2627, which is described in further detail below.

The cover 2630 also includes an opening 2632 extending therethough. The opening 2632 is substantially positioned centrally within the cover 2630 and is sized to be the same diameter or shape as the opening 2681. However, opening 2632 can be sized and/or shaped differently than opening 2681 according to other exemplary embodiments. According to the exemplary embodiment, at least a portion of the opening 2632 is vertically aligned with at least a portion of the opening 2681.

A first seal 2631 is positioned about the perimeter of the opening 2632 and provides a pressure seal between the cover 2630 and the rock sample 2680 about the opening 2632 and the opening 2681, thereby preventing or minimizing any second fluid 2626 leakage from the interface between the opening 2681 and the opening 2632. The first seal 2631 is shaped similar to the shape of the opening 2632. A second seal 2633 is positioned at a location on the bottom surface 2634 which contacts the top surface 2682 of the rock sample 2680. In some exemplary embodiments, the second seal 2633 is positioned at a location on the bottom surface 2634 which contacts the perimeter of the top surface 2682 of the rock sample 2680. The second seal 2633 provides a pressure seal between the cover 2630 and the rock sample 2680 substantially about the perimeter of the top surface 2682 of the rock sample 2680, thereby preventing or minimizing any first fluid 2621 leakage from the interface between the cover 2630 and the perimeter of the top surface 2682 of the rock sample 2680. A third seal 2635 is positioned at the perimeter of the bottom surface 2634 of the cover 2630. The third seal 2635 provides a pressure seal between the cover 2630 and the sidewall 2616 of the pressurizable chamber 2610, thereby preventing or minimizing any first fluid 2621 leakage from the interface between the cover 2630 and the sidewall 2616 of the pressurizable chamber 2610. The seals 2631, 2633, and 2635 are a rubber gasket or any other suitable material known to people having ordinary skill in the art. Once the bottom portion of the cover 2630 is properly inserted into the pressurizable chamber 2610, the first seal 2631 and the second seal 2633 are in contact with the top surface 2682 of the rock sample 2680. The pressure within the cavity 2612 surrounding the rock sample 2680 is a first pressure ($P_1$) 2622 which can be different than the second pressure 2627 within the openings 2632 and 2681 during testing which is described in further detail below. Each of the first pressure 2622 and the second pressure 2627 is variable. Thus, a portion of the rock sample 2680 is exposed to the first pressure 2622 while another portion of the rock sample 2680 is exposed to the second pressure 2627 during testing.

Within the cavity 2612 surrounding the rock sample 2680, a first fluid 2621 is placed. This portion of the cavity 2612 can be referred to as a first chamber 2620. The first fluid 2621 fills up the first chamber 2620 in some exemplary embodiments; however, in other exemplary embodiments, the first fluid 2621 fills a portion of the first chamber 2620. The first fluid 2621 is water. However, other types of fluid having similar properties can be used as the first fluid 2621 in other exemplary embodiments. In some exemplary embodiments, the first fluid 2621 includes sand particles or other similar particle types.

A second fluid 2626 flows into and fills up the opening 2681. According to some exemplary embodiments, the second fluid 2626 is pumped into opening 2632 and opening 2681. However, in other exemplary embodiments, the pressure of the second fluid is provided using other known methods, such as having a reservoir of second fluid fluidly coupled to the openings 2632 and 2681 and having a piston (not shown) provide a force to a movable plate (not shown) within the reservoir, similar to the second barrier 2540 described above. The opening 2681 can be referred to as a second chamber. The second fluid 2626 is water. However, other types of fluid having similar properties can be used as the second fluid 2626 in other exemplary embodiments. In some exemplary embodiments, the second fluid 2626 includes sand particles or other similar particle types. According to some exemplary embodiments, the second fluid 2626 is the same as the first fluid 2621; however, the second fluid 2626 can be different than, but similar in properties to, the first fluid 2621 in other exemplary embodiments. As the second pressure 2627 in the second chamber 2681 increases above the first pressure 2622 in the first chamber 2620, the second fluid 2626 flows from the second chamber 2681 into the rock sample 2680 and out into the first chamber 2620. As the second pressure 2627 increases, acoustic events, or cracks, form in the rock sample 2680. In the exemplary embodiments where sand particles are included in the second fluid 2626, the sand particles can enter into the cracks formed within the rock sample 2680 and become lodged therein as to prevent the cracks from closing when the second pressure 2627 is decreased.

As the second pressure 2627 increases and the second fluid 2626 flows into the first chamber 2620 through the rock sample 2680, the first pressure 2622 increases. To maintain the first pressure 2622 constant or substantially constant, a drain pipe 2595 is coupled to the interior of the first chamber 2620 and through the sidewall 2616 to allow the first fluid 2621 and/or the second fluid 2626 that is present within the first chamber 2620 to exit the first chamber 2620. The drain pipe 2595 is fabricated from a metal, metal alloy, polymer, or other suitable material capable of withstanding the first pressure 2622. In certain exemplary embodiments, the drain pipe pressure control valve 2597 is installed at a location along the drain pipe 2595 and is configured to be opened and closed, either automatically or manually, to maintain the first pressure 2622 at a substantially constant pressure during the testing process. In alternative exemplary embodiments, the drain pipe 2595 is coupled to the interior of the first chamber 2620 through the base 2614.

The operation of the acoustic emission testing system 2600 is described while referring to FIG. 26. Once the acoustic emission testing system 2600 is configured according to the description provided above, the drain pipe control valve 2597 is set to maintain the pressure in the first chamber 2620 at the first pressure 2622. The first pressure 2622 is determined to be the rock confining pressure, which is the pressure at which the rock sample 2680 was exposed to while in the wellbore. The second fluid 2626 is pushed into the second chamber 2681 at the second pressure 2627 which applies a force on the rock sample 2680 from within. The second pressure 2627 increases to a value above the first pressure 2622 and is ramped up so that acoustic events, or cracking, occurs on or within the rock sample 2680. The second pressure 2627 is continuously ramped up until the second pressure 2627 reaches a threshold pressure, where extensive acoustic events occur within the rock sample 2680. Once the second pressure 2627 increases above the first pressure 2622, the second fluid 2626 passes through the porous rock sample 2680 and enters into the first chamber 2620. The first pressure 2622 would typically increase due to the second fluid 2626 entering the first chamber 2620; however, the drain pipe control valve 2597 maintains the first pressure 2622 substantially constant and allows the first fluid 2621 and/or the second fluid 2626 that has entered into the first chamber 2620 to exit the first chamber 2620 through the pipe drain 2595. This threshold pressure that is reached is the pressure that is to be generated in the wellbore for fracing the rock at that confining pressure. During the testing procedure, the acoustic events are measured according to the descriptions provided above. Additionally, the location of the acoustic events are determinable by people having ordinary skill in the art having the benefit of the present disclosure. Moreover, the direction in which the acoustic events are propagating also are determinable by people having ordinary skill in the art having the benefit of the present disclosure. The acoustic sensors 2570 obtain data when the second pressure 2627 is increased. Additionally, in some exemplary embodiments, the acoustic sensors 2570 also obtain data when the second pressure 2627 is decreased after reaching the threshold pressure. Although not illustrated, the first pressure 2622 and the second pressure 2627 are monitored. According to some exemplary embodiments, the second pressure 2627 is recorded.

Figure 27:
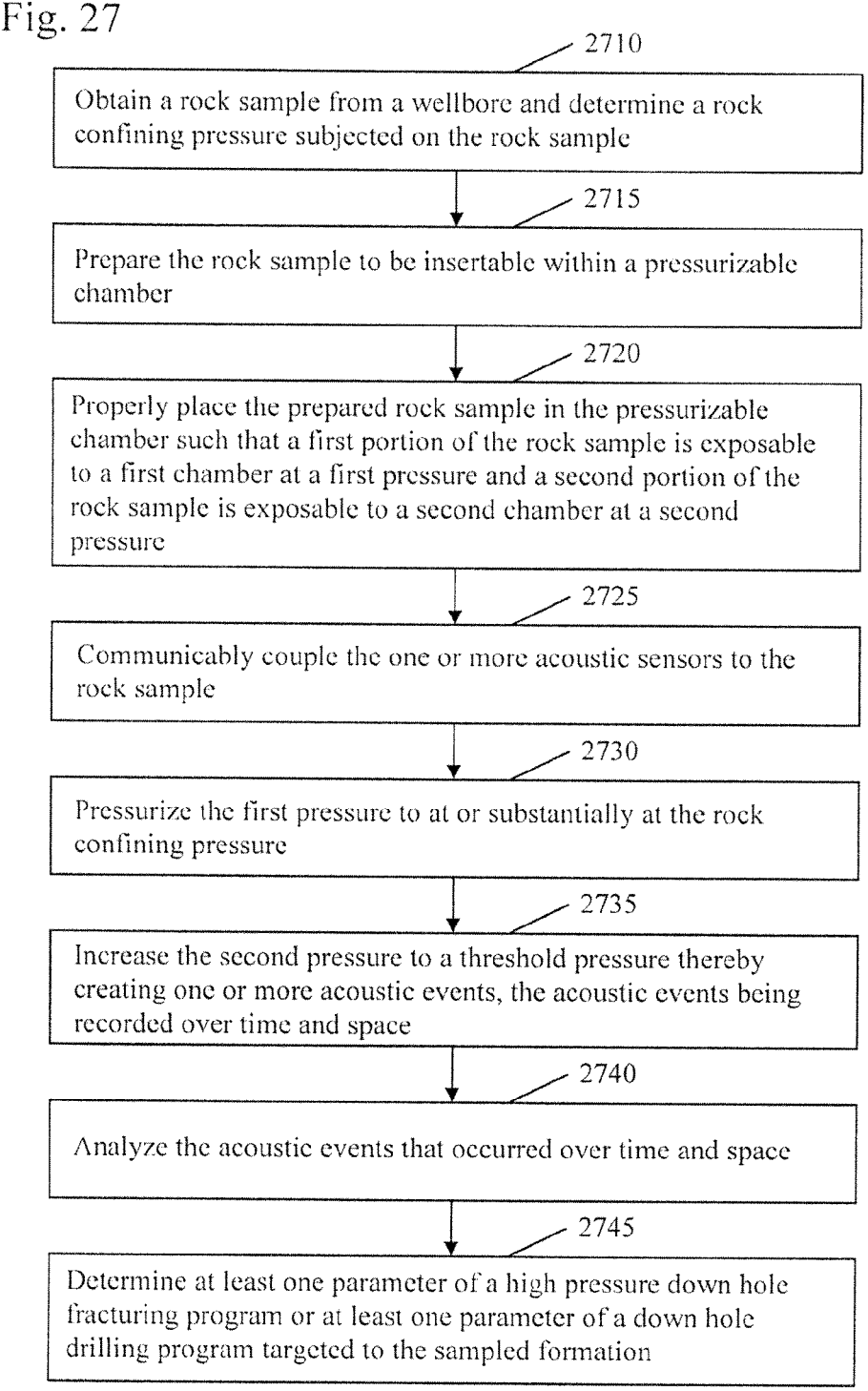
FIG. 27 shows an acoustic testing method in accordance with an exemplary embodiment of the present invention.

FIG. 27 shows an acoustic testing method 2700 in accordance with an exemplary embodiment. Although the acoustic testing method 2700 illustrates one or more steps occurring in a certain order, one or more of the steps occur in a different order according to other exemplary embodiments. Additionally, one or more steps are combined into fewer steps according to some exemplary embodiments, while one or more steps are expanded into more steps according to some exemplary embodiments. Thus, the illustrated order of steps and the number of steps are not to be construed as being limiting.

The acoustic testing method 2700 includes a step 2710. At step 2710, a rock sample is obtained from a wellbore at a certain depth and a rock confining pressure exposed on the rock sample within the wellbore is observed. According to some exemplary embodiments, the rock sample is obtained from the wellbore that is currently being drilled. In other exemplary embodiments, the rock sample is obtained from a wellbore that is nearby a site that is intended to be drilled. The method 2700 also includes step 2715 where the rock sample is prepared so that the rock sample is insertable within a pressurizable chamber. The rock sample is fabricated into a desired shape so that it is insertable within the pressurizable chamber. Once the rock sample is prepared, the method proceeds to step 2720 where the prepared rock sample is properly placed in the pressurizable chamber such that a first portion of the rock sample is exposable to a first chamber at a first pressure and a second portion of the rock sample is exposable to a second chamber at a second pressure. According to some exemplary embodiments, the first portion includes at least a portion of the sidewall of the rock sample and the second portion includes the top surface of the rock sample. According to some other exemplary embodiments, the first portion includes the top surface of the rock sample and the second portion includes at least a portion of the sidewall of the rock sample. Yet, according to some other exemplary embodiments, the first portion includes an exterior portion of the rock sample, such as the outer surface of the sidewall, and the second portion includes an interior portion of the rock sample. In an alternative exemplary embodiment, the first portion includes an interior portion of the rock sample and the second portion includes an exterior portion of the rock sample, such as the outer surface of the sidewall.

The method 2700 also includes step 2725, where one or more acoustic sensors are communicably coupled to the rock sample. According to some exemplary embodiments, three acoustic sensors are coupled to the surface of the rock sample in a manner where each acoustic sensor is positioned at a different elevation from one another. Although three acoustic sensors are coupled to the rock sample, greater or fewer acoustic sensors are usable in other exemplary embodiments. Also, although each acoustic sensor is positioned at a different elevation from one another, at least one acoustic sensor is positionable substantially at the same elevation as another acoustic sensor in other exemplary embodiments. Further, although the acoustic sensors are coupled to the surface of the rock sample, one or more of the acoustic sensors are coupled to the pressurizable chamber in other exemplary embodiments.

The method 2700 also includes step 2730, where the first pressure in the first chamber is pressurized to at or substantially at the rock confining pressure, which is the pressure that the rock sample was exposed to while in the wellbore. According to some exemplary embodiments, a first fluid that has been placed in the first chamber exerts the first pressure onto the first portion of the rock sample. The method 2700 also includes step 2735, where the second pressure in the second chamber is increased to a threshold pressure while the acoustic events occurring within the rock sample are recorded over time and space. According to some exemplary embodiments, a second fluid, which is the same or similar to the first fluid, has been placed in the second chamber and exerts the second pressure onto the second portion of the rock sample. The threshold pressure is the pressure at which acoustic events are formed quickly and extensively within and/or on the rock sample.

The method 2700 also includes step 2740. In step 2740, the fracturing events that occurred over time and space are analyzed. This analysis includes the processes described above according to some exemplary embodiments. According to some exemplary embodiments, the intensity of one or more fracturing events, or acoustic events, is determined. According to some exemplary embodiments, the location of one or more fracturing events, or acoustic events, that occurred within the rock sample is determined. According to some exemplary embodiments, the direction in which one or more fracturing events, or acoustic events, are propagating is determined. After step 2740, the method 2700 proceeds to step 2745. In step 2745, at least one parameter of a high pressure down hole fracturing program or at least one parameter of a down hole drilling program targeted to the sampled formation is determine based upon the analysis of the fracturing events. For example, based upon the analysis, the pressure that needs to be exerted by the bit on the rock within the wellbore to create a proper fracing program is the threshold pressure, which is the pressure of the second pressure when substantial fracing of the rock occurs. In another example, the weight-on-bit is calculable from knowing the pressure that the bit is to exert on the rock within the wellbore.

Figure 28:
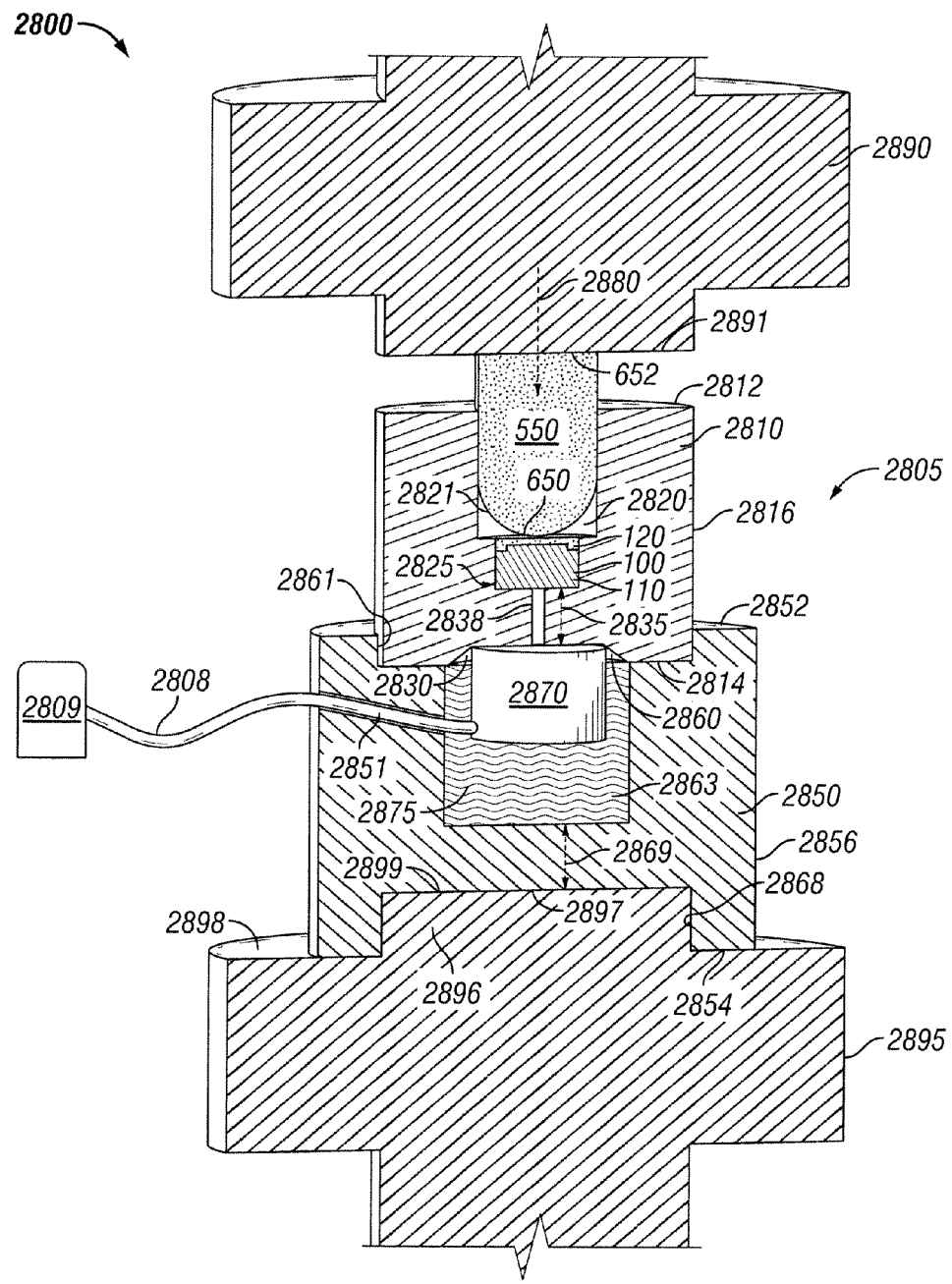
FIG. 28 shows a cross-sectional view of an acoustic emission testing system in accordance with yet another exemplary embodiment of the present invention.

FIG. 28 shows a cross-sectional view of an acoustic emission testing system 2800 in accordance with yet another exemplary embodiment of the present invention. Referring to FIG. 28, the acoustic emission testing system 2800 includes an acoustic emission testing device 2805 communicably coupled to a data recorder 2809. The acoustic emission testing device 2805 includes a cutter holder 2810, the cutter 100, the indenter 550, an acoustic sensor holder 2850, an acoustic sensor 2870, a first rod 2890, and a second rod 2895. Although the cutter 100 is depicted in the exemplary embodiment, the rock sample 2300 (FIG. 23) or other type of hard or superhard component, replaces the cutter 100 in alternative exemplary embodiments.

The cutter holder 2810 includes a first surface 2812, a second surface 2814, and a side surface 2816. The first surface 2812 is disposed in a plane that is substantially parallel to the plane that the second surface 2814 is disposed. The side surface 2816 extends from the perimeter of the first surface 2812 to the perimeter of the second surface 2814. According to some exemplary embodiments, the side surface 2816 is substantially perpendicular to at least one of the first surface 2812 and the second surface 2814. According to alternative exemplary embodiments, the side surface 2816 is not substantially perpendicular to either the first surface 2812 or the second surface 2814. The cutter holder 2810 is shaped in a substantially cylindrical shape, wherein the first surface 2812 is substantially circular shaped, the second surface 2814 is substantially circular shaped, and the side surface 2816 is substantially cylindrically and arcuately shaped. Although one exemplary shape is provided for the cutter holder 2810, the cutter holder 2810 can be shaped into any other geometric or non-geometric shape, such as a square shaped cylinder or a triangular shaped cylinder, without departing from the scope and spirit of the exemplary embodiment. The cutter holder 2810 is fabricated from steel; however, according to other exemplary embodiments, the cutter holder 2810 is fabricated from any metal, wood, or other suitable material known to people having ordinary skill in the art that is capable of withstanding a load 2880, which is described in further detail below. The load 2880 ranges from about zero kilonewtons to about seventy kilonewtons, but is higher in other exemplary embodiments. In certain exemplary embodiments, the suitable material is capable of being machined or molded and is capable of propagating sound therethrough. In certain exemplary embodiments, the suitable material is capable of propagating sound at a speed of about 1 kilometers per second or higher.

The cutter holder 2810 also includes a first cavity 2820 and a second cavity 2830 according to some exemplary embodiments. In certain exemplary embodiments, the cutter holder 2820 also includes a channel 2838 extending from the first cavity 2820 to the second cavity 2830. The first cavity 2820 is formed within the first surface 2812 of the cutter holder 2810 and extends toward the second surface 2814, but does not reach the second surface 2814. The first cavity 2820 includes a first portion 2821 and a second portion 2825 formed adjacent to the first portion 2821 according to certain exemplary embodiments. The first portion 2821 extends from the first surface 2812 of the cutter holder 2810 and extends into the cutter holder 2810 to the second portion 2825. According to some exemplary embodiments, the first portion 2821 is formed having a circular cross-section; however, the shape is different in other exemplary embodiments. The first portion 2821 is sized to receive at least a portion of the indenter 550, which has previously been described. For example, the first portion 2821 is sized slightly larger in diameter than the diameter of the indenter 550, thereby allowing the indenter 550 to easily and freely fit within the first portion 2821.

The second portion 2825 extends from the first portion 2821 towards the second surface 2814. According to some exemplary embodiments, the second portion 2825 is formed having a circular cross-section; however, the shape is different in other exemplary embodiments. The second portion 2825 is sized to receive at least a portion of the cutter 100, which has previously been described, or some other hard or superhard material, such as the rock sample 2300 (FIG. 23), for which properties are to be determined. For example, the diameter of the second portion 2825 is sized slightly larger in diameter than the diameter of the cutter 100, thereby allowing the cutter 100 to easily and freely fit within the second portion 2825. According to some exemplary embodiments, the central axial axis of the first portion 2821 is substantially the same as the central axial axis of the second portion 2825; however, these axes are aligned differently in other exemplary embodiments. In some exemplary embodiments, the second portion 2825 has a smaller diameter than the first portion 2821. In certain exemplary embodiments, the first cavity 2820 includes the second portion 2825, but not the first portion 2821. Thus, in these exemplary embodiments, the second portion 2825 extends from the first surface 2812 towards the second surface 2814.

In certain exemplary embodiments, the second cavity 2830 is formed within the second surface 2814 of the cutter holder 2810 and extends toward the second portion 2825 of the first cavity 2820, but does not reach the second portion 2825. However, this second cavity 2830 is optional. A thickness 2835 is formed between the second portion 2825 and the second cavity 2830. The thickness 2835 is able to withstand the load 2880 without breaking. According to some exemplary embodiments, the second cavity 2830 is formed having a conicle cross-section; however, the shape is different in other exemplary embodiments. The second cavity 2830 is sized to receive at least a portion of the acoustic sensor 2870, which is described in further detail below. In exemplary embodiments that do not include the second cavity 2830, the acoustic sensor 2870 is positioned adjacent to the second surface 2814.

According to some exemplary embodiments, the channel 2838 is formed extending from the second cavity 2830 to the second portion 2825 of the first cavity 2820. The central axial axis of the channel 2838 corresponds to the previously mentioned central axial axes according to certain exemplary embodiments. The channel 2838 provides a direct pathway for the acoustic waves to travel from the cutter 100 to the acoustic sensor 2870.

One or more of the cavities 2820, 2830, and channel 2838 are formed by machining the cutter holder 2810 or molding the cutter holder 2810 to have the cavities 2820, 2830 and the channel 2838 formed therein. Alternatively, one or more of the cavities 2820, 2830 and the channel 2838 are formed using other methods or combination of methods known to people having ordinary skill in the art. In certain exemplary embodiments, the first cavity 2820 is formed in a manner to ensure that the cutter 100 is properly aligned in the same manner each time the cutter 100 is inserted within the first cavity 2820.

The cutter 100 has been previously described and is applicable to the exemplary embodiments. Briefly, the cutter 100 includes the substrate 110 and the cutter table 120, which is formed or coupled to the top of the substrate 110. In the exemplary embodiment, the cutter table 120 is formed from PCD, but alternative exemplary embodiments have the cutter table 120 fabricated from other materials, such as PCBN, without departing from the scope and spirit of the exemplary embodiment. Although cutter 100 has a planar cutter table 120, or is flat-faced, the cutter table 120 can be dome shaped, concave shaped, or any other shape known to people having ordinary skill in the art. As previously mentioned, the cutter 100 includes finished and/or grounded cutters as well as "raw" cutters.

The cutter 100 is inserted within the second portion 2825 of the first cavity 2820. The cutter 100 is oriented within the second portion 2825 so that the cutter table 120 is facing towards the first surface 2812, or away from the second surface 2814. According to some exemplary embodiments, the entire cutter 100 is inserted within the second portion 2825. However, in alternative exemplary embodiments, a portion of the cutter 100, which includes substantially the entire substrate 110, is inserted within the second portion 2825 of the first cavity 2820. Thus, in these alternative exemplary embodiments, at least a portion of the cutter table 120 is not inserted within the second portion 2825. The portion of the cutter 100 inserted within the second portion 2825 is securely positioned therein. However, according to some exemplary embodiments, the portion of the cutter 100 inserted within the second portion 2825 is loosely positioned therein. According to these other exemplary embodiments, a lubricant (not shown) is disposed within the second portion 2825 between the cutter 100 and the surface of the second portion 2825. Although the cutter 100 is described as being used in this exemplary embodiment, other hard or superhard materials that desire a toughness testing can be used in lieu of the cutter 100.

The indenter 550 has been previously described and is not repeated for the sake of brevity. The indenter 550 is sized to fit within at least the first portion 2821 of the first cavity 2820 so that it makes contact with the cutter 100. In certain exemplary embodiments, the perimeter of the indenter 550 is sized substantially similar to the perimeter of the first portion 2821. However, in the exemplary embodiments where at least a portion of the cutter table 120 is not within the first cavity 2820 and is positioned elevationally above the first surface 2812, the indenter 550 can be dimensioned such that the perimeter of the indenter 550 is greater than the perimeter of the first portion 2821 of the first cavity 2820. The indenter 550 is oriented so that the indenter's first end 650 makes contact with the cutter 100. Thus, in this embodiment, indenter 550 makes contact with the PDC layer, or cutter table 120, of the cutter 100. The load 2880 is applied to the indenter's second end 652, which transmits the load 2880 onto the cutter 100.

The acoustic sensor holder 2850 includes a first surface 2852, a second surface 2854, and a side surface 2856. The first surface 2852 is disposed in a plane that is substantially parallel to the plane that the second surface 2854 is disposed. The side surface 2856 extends from the perimeter of the first surface 2852 to the perimeter of the second surface 2854. According to some exemplary embodiments, the side surface 2856 is substantially perpendicular to at least one of the first surface 2852 and the second surface 2854. According to alternative exemplary embodiments, the side surface 2856 is not substantially perpendicular to either the first surface 2852 or the second surface 2854. The acoustic sensor holder 2850 is shaped in a substantially cylindrical shape, wherein the first surface 2852 is substantially circular shaped, the second surface 2854 is substantially circular shaped, and the side surface 2856 is substantially cylindrically and arcuately shaped. Although one exemplary shape is provided for the acoustic sensor holder 2850, the acoustic sensor holder 2850 is shaped differently in other exemplary embodiments. The acoustic sensor holder 2850 is fabricated from cemented carbide, such as cemented tungsten carbide; however, according to other exemplary embodiments, the acoustic sensor holder 2850 is fabricated from any other suitable material, such as lead, that has an acoustic impedance that is higher than the material used to fabricate the second rod 2895 and that is capable of withstanding the load 2880. In certain exemplary embodiments, the suitable material is capable of being machined or molded and is capable of propagating sound. In certain exemplary embodiments, the suitable material is capable of propagating sound at a speed of about 1 kilometers per second or higher. The material that the acoustic sensor holder 2850 is fabricated has a higher acoustic impedance than the material used to fabricate the second rod 2895, which thereby causes the noise sound waves to be reflected into the second rod 2895 and not back into the acoustic sensor 2870. Hence, the signal to noise ratio that is detected by the acoustic sensor 2870 is improved within the system 2800.

The acoustic sensor holder 2850 also includes a first cavity 2860 and a second cavity 2868 according to some exemplary embodiments. The first cavity 2860 is formed within the first surface 2852 of the acoustic sensor holder 2850 and extends toward the second surface 2854, but does not reach the second surface 2854. The first cavity 2860 includes a first portion 2861 and a second portion 2863 formed adjacent to the first portion 2861 according to certain exemplary embodiments. The first portion 2861 extends from the first surface 2852 of the acoustic sensor holder 2850 to the second portion 2863 within the acoustic sensor holder 2850. According to some exemplary embodiments, the first portion 2861 is formed having a circular cross-section; however, the shape is different in other exemplary embodiments. The first portion 2861 is sized to securely receive a lower portion of the cutter holder 2810, which includes the cutter holder's second surface 2814. For example, the first portion 2861 is sized slightly larger in diameter than the diameter of the cutter holder's second surface 2814, thereby allowing the cutter holder's second surface 2814 to easily and securely fit within the first portion 2861.

The second portion 2863 extends from the first portion 2861 towards the second surface 2854. According to some exemplary embodiments, the second portion 2863 is formed having a circular cross-section; however, the shape is different in other exemplary embodiments. The second portion 2863 is sized to receive at least a portion of the acoustic sensor 2870. For example, the diameter of the second portion 2863 is sized larger than the diameter of the acoustic sensor 2870. According to some exemplary embodiments, the central axial axis of the first portion 2861 is substantially the same as the central axial axis of the second portion 2863; however, these axes are aligned differently in some other exemplary embodiments. In some exemplary embodiments, the second portion 2863 has a smaller diameter than the first portion 2861.

In certain exemplary embodiments, the second cavity 2868 is formed within the second surface 2854 of the acoustic sensor holder 2850 and extends toward the second portion 2863 of the first cavity 2860, but does not reach the second portion 2863. However, this second cavity 2868 is optional. A thickness 2869 is formed between the second portion 2863 and the second cavity 2868. The thickness 2869 is able to withstand the load 2880 without breaking. According to some exemplary embodiments, the second cavity 2868 is formed having a circular cross-section; however, the shape is different in other exemplary embodiments. The second cavity 2868 is sized to receive at least a portion of the second rod 2895, which is described in further detail below.

The cavities 2860, 2868 are formed by machining the acoustic sensor holder 2850 or molding the acoustic sensor holder 2850 to have the cavities 2860, 2868 formed therein. Alternatively, the cavities 2860, 2868 are formed using other methods or combination of methods known to people having ordinary skill in the art.

The acoustic sensor 2870 is a piezoelectric sensor in some exemplary embodiments; however, the acoustic sensor 2870 is any other device type known to people having ordinary skill in the art, wherein the device is capable of detecting acoustic transmissions. The acoustic sensor 2870 detects elastic wave signals formed in the cutter 100, which then converts the elastic waves signal to a voltage signal so that the data can be recorded and subsequently analyzed. The acoustic sensor 2870 has a sensitivity range spanning from one to about 1,000 kilohertz, which allows the detection of acoustic emission events too week or too short to be detected based upon previously described system configurations. The acoustic sensor 2870 is positioned within at least the second portion 2863 of the acoustic sensor holder's first cavity 2860. In certain exemplary embodiments, a portion of the acoustic sensor 2870 extends into the first portion 2861 of the acoustic sensor holder's first cavity 2860. The acoustic sensor 2870 is coupled to or is in contact with the cutter holder 2850. In certain exemplary embodiments, a portion of the acoustic sensor 2870 is received within the second cavity 2830 of the cutter holder 2810. In some exemplary embodiments, each of the indenter 550, the cutter 100, and the acoustic sensor 2870 are substantially aligned linearly. In certain exemplary embodiments, a low density material 2875, such as a lubricant, is placed around the acoustic sensor 2870 once positioned within the acoustic sensor holder's first cavity 2860. The low density material 2875 fills in the remaining portion of the first cavity 2860 between at least the surface of the first cavity's second portion 2863 and the acoustic sensor 2870. The low density material 2875 isolates the acoustic sensor 2870 from detecting surrounding environmental noise or at least reduces the detection of this noise. The acoustic sensor 2870 is communicably coupled to the data recorder 2809 so that the voltage signal derived from the elastic waves occurring within the cutter 100 can be stored and subsequently analyzed. The acoustic sensor 2870 is coupled to the data recorder 2809 using a cable 2808; however, according to other exemplary embodiments, the acoustic sensor 2870 is communicably coupled to the data recorder 2809 wirelessly using wireless technology including, but not limited to, infrared and radio frequency. In the embodiments where the cable 2808 couples the acoustic sensor 2870 to the data recorder 2809, a passageway 2851 is formed extending from the acoustic sensor holder's side surface 2856 to the acoustic sensor holder's first cavity 2860. The passageway 2851 allows the cable 2808 to communicate from within the acoustic sensor holder's first cavity 2860 to the data recorder 2809.

The first rod 2890 includes a first end 2891 that is oriented to apply the load 2880 onto the indenter's second end 652. The first rod's first end 2891 is positioned adjacent to the indenter's second end 652 and then pressed on the indenter 550, thereby applying the load 2880 thereon. The first end 2891 is substantially planar according to some exemplary embodiments; however, the first end 2891 is non-planar in other exemplary embodiments. The first rod 2890 is fabricated using a metal, or alternatively, any other suitable material capable of withstanding the load 2880.

The second rod 2895 includes a first end 2896 that is shaped to be securely coupled to the lower portion of the acoustic sensor holder 2850. The first end 2896 includes a raised portion 2897 and a recessed portion 2898 surrounding the raised portion 2897. The raised portion 2897 is shaped similarly to the shape of the acoustic sensor holder's second cavity 2868 so that at least a portion of the raised portion 2897 is insertable into the acoustic sensor holder's second cavity 2868 to securely couple the second rod 2895 to the acoustic sensor holder 2850. The raised portion 2897 includes a substantially planar surface 2899 according to some exemplary embodiments; however, the surface 2899 is non-planar depending upon the shape of the acoustic sensor holder's second cavity 2868 in other exemplary embodiments. The second rod 2895 is fabricated using steel, or alternatively, any other suitable material capable of withstanding the load 2880 and having a lower acoustic impedance than the material used to fabricate the acoustic sensor holder 2850, such as aluminum, brass, plastic, and wood. As previously mentioned, this low acoustic impedance material allows the sound to continue travelling into and through the material, rather than being reflected back into the acoustic sensor 2870. In certain exemplary embodiments, at least one of the cutter holder 2810, the acoustic sensor holder 2850, and the second rod 2895 is fabricated from a material having a much higher density or a much lower density than at least one of the other remaining components. For example, the density of one of the components is at least about 1.5 times greater than at least one of the previously mentioned components.

Although one exemplary configuration of the acoustic emission testing device 2805 has been illustrated and described, other configurations, known to people having ordinary skill in the art having the benefit of the present disclosure, can be used without departing from the scope and spirit of the exemplary embodiments. For example, the coupling and/or interlocking features of adjacent components can be performed in a variety of ways in other exemplary embodiments. For example, the lower portion of the cutter holder 2810 is partially inserted within a first cavity 2860 formed in the upper portion of the acoustic sensor holder 2850. Alternatively, in other exemplary embodiments, the upper portion of the acoustic sensor holder 2850.is partially inserted within a cavity (not shown) formed in the lower portion of the cutter holder 2810.

The data recorder 2809 is similar to the data recorder 590 (FIG. 5), but is capable of recording up to about 100,000 data points per second. In alternative exemplary embodiments, the data recorder 2809 records even more data points per second. The data recorder 2809 records the data sent from the acoustic sensor 2870 and stores the data therein. In some exemplary embodiments, the data recorder 2890 also is communicably coupled to one or more components, such as the first rod 2890, to obtain data for quantifying the load 2880. The data is processed according to the description provided above.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. An acoustic emission testing device, comprising:
a hard component holder comprising a first end and a second end opposite the first end, the first end defining a first cavity extending towards the second end;
a hard component positioned in the first cavity;
an indenter positioned adjacent to a portion of the hard component;
an acoustic sensor holder comprising an upper portion, a lower portion, and a second cavity therein, the upper portion coupled to the second end of the hard component holder; and
an acoustic sensor positioned within the second cavity,
wherein the acoustic sensor senses one or more acoustic events occurring within the hard component when the indenter applies a load onto the hard component.

2. The acoustic emission testing device of claim 1, wherein the upper portion comprises a top surface defining a portion of the second cavity, the second cavity extending toward the lower portion, and wherein at least a portion of the acoustic sensor is positioned adjacent the second end of the hard component holder.

3. The acoustic emission testing device of claim 2, wherein the second end of the hard component holder defines an aperture, the aperture extending towards the first cavity, and wherein the acoustic sensor is positioned within the aperture and adjacent the second end of the hard component holder.

4. The acoustic emission testing device of claim 1, further comprising a lubrication disposed within the second cavity and surrounding at least portions of the acoustic sensor.

5. The acoustic emission testing device of claim 1, wherein the acoustic sensor holder is interlockingly coupled to the hard component holder.

6. The acoustic emission testing device of claim 1, further comprising a first rod coupled to the lower portion of the acoustic sensor holder, the first rod having a lower acoustic impedance than the acoustic sensor holder.

7. The acoustic emission testing device of claim 6, wherein the first rod is interlockingly coupled to the acoustic sensor holder.

8. The acoustic emission testing device of claim 1, wherein the hard component includes at least one of a polycrystalline diamond cutter, a polycrystalline boron nitride cutter, and a rock sample.

9. The acoustic emission testing device of claim 1, wherein the hard component, the indenter, and the acoustic sensor are substantially aligned linearly.

10. The acoustic emission testing device of claim 1, wherein the hard component holder further comprises a passageway extending from the first cavity to the second end.

11. The acoustic emission testing device of claim 1, further comprising a first rod coupled to the lower portion of the acoustic sensor holder, wherein at least one of the hard component holder, the acoustic sensor holder, and the first rod is fabricated from a denser material than at least one of the remaining components.

12. An acoustic emission testing system, comprising:
an acoustic emission testing device comprising:
a hard component holder comprising a first end and a second end opposite the first end, the first end defining a first cavity extending towards the second end;
a hard component positioned in the first cavity;
an indenter positioned adjacent to a portion of the hard component;
an acoustic sensor holder comprising an upper portion, a lower portion, and a second cavity therein, the upper portion coupled to the second end of the hard component holder; and
an acoustic sensor positioned within the second cavity; and
a data recorder communicably coupled to the acoustic emission testing device, the data recorder receiving data from the acoustic emission testing device, and
wherein the acoustic sensor senses one or more acoustic events occurring within the hard component when the indenter applies a load onto the hard component.

13. The acoustic emission testing system of claim 12, wherein the data recorder is coumminicably coupled to the acoustic emission testing device using a cable.

14. The acoustic emission testing system of claim 12, wherein the upper portion comprises a top surface defining a portion of the second cavity, the second cavity extending toward the lower portion, and wherein at least a portion of the acoustic sensor is positioned adjacent the second end of the hard component holder.

15. The acoustic emission testing system of claim 14, wherein the second end of the hard component holder defines an aperture, the aperture extending towards the first cavity, and wherein the acoustic sensor is positioned within the aperture and adjacent the second end of the hard component holder.

16. The acoustic emission testing system of claim 12, wherein the acoustic emission testing device further comprises a first rod coupled to the lower portion of the acoustic sensor holder, the first rod having a lower acoustic impedance than the acoustic sensor holder.

17. The acoustic emission testing system of claim 12, wherein the hard component, the indenter, and the acoustic sensor are substantially aligned linearly.

18. The acoustic emission testing system of claim 12, wherein the hard component holder further comprises a passageway extending from the first cavity to the second end.

19. A method for testing a hard component, comprising:
providing a hard component holder, the hard component holder comprising a first end and a second end opposite the first end, the first end defining a first cavity extending towards the second end;
positioning a hard component within the first cavity;
positioning an indenter adjacent to a portion of the hard component;
coupling an upper portion of an acoustic sensor holder to the second end of the hard component holder, the acoustic sensor holder comprising the upper portion, a lower portion, and a second cavity therein;
positioning an acoustic sensor within the second cavity;
applying a load onto the indenter thereby supplying the load onto the hard component;
generating one or more acoustic events within the hard component; and
detecting the one or more acoustic events.

20. The method of claim 19, wherein the upper portion comprises a top surface defining a portion of the second cavity, the second cavity extending toward the lower portion, and wherein the acoustic sensor is positioned adjacent the second end of the hard component holder.

21. The method of claim 20, wherein the second end of the hard component holder defines an aperture, the aperture extending towards the first cavity, and wherein at least a portion of the acoustic sensor is positioned within the aperture and adjacent the second end of the hard component holder.

22. The method of claim 19, further comprising disposing a lubrication within the second cavity and surrounding at least portions of the acoustic sensor.

23. The method of claim 19, further comprising coupling a first rod to the lower portion of the acoustic sensor holder, the first rod having a lower acoustic impedance than the acoustic sensor holder.

24. The method of claim 19, wherein the hard component, the indenter, and the acoustic sensor are substantially aligned linearly.

* * * * *